United States Patent
McGonigle

(10) Patent No.: US 9,631,190 B2
(45) Date of Patent: *Apr. 25, 2017

(54) CELL ATTACHMENT COATINGS AND METHODS USING PHOSPHOROUS-CONTAINING PHOTOREAGENT

(71) Applicant: SurModics, Inc., Eden Prairie, MN (US)

(72) Inventor: Joseph S. McGonigle, Minneapolis, MN (US)

(73) Assignee: SURMODICS, INC., Eden Prairie, MN (US)

( * ) Notice: Subject to any disclaimer, the term of this patent is extended or adjusted under 35 U.S.C. 154(b) by 185 days.

This patent is subject to a terminal disclaimer.

(21) Appl. No.: 13/930,512

(22) Filed: Jun. 28, 2013

(65) Prior Publication Data

US 2014/0004158 A1 Jan. 2, 2014

Related U.S. Application Data

(60) Provisional application No. 61/666,516, filed on Jun. 29, 2012.

(51) Int. Cl.
*C12N 11/06* (2006.01)
*A61K 38/08* (2006.01)
*A61L 31/10* (2006.01)
*A61L 31/16* (2006.01)

(52) U.S. Cl.
CPC ............. *C12N 11/06* (2013.01); *A61L 31/10* (2013.01); *A61L 31/16* (2013.01); *A61L 2300/25* (2013.01); *A61L 2300/252* (2013.01); *A61L 2300/64* (2013.01); *A61L 2420/08* (2013.01); *C12N 2303/00* (2013.01)

(58) Field of Classification Search
CPC .... A61L 31/16; A61L 27/56; A61L 2300/414; A61L 27/46; A61L 2300/252; A61L 2300/606; A61L 31/14; A61L 2300/412; A61L 27/3633; A61L 2300/604; A61L 27/32; A61L 29/16; A61K 38/17; A61K 33/42; C12N 5/0018; C12N 5/0671; C12N 2535/10
See application file for complete search history.

(56) References Cited

U.S. PATENT DOCUMENTS

| | | | |
|---|---|---|---|
| 4,979,959 A | 12/1990 | Guire | |
| 5,414,075 A | 5/1995 | Swan et al. | |
| 5,563,056 A | 10/1996 | Swan et al. | |
| 5,637,460 A | 6/1997 | Swan et al. | |
| 5,714,360 A | 2/1998 | Swan et al. | |
| 5,744,515 A | 4/1998 | Clapper | |
| 5,858,653 A | 1/1999 | Duran et al. | |
| 6,007,833 A | 12/1999 | Chudzik et al. | |
| 6,121,027 A | 9/2000 | Clapper et al. | |
| 6,156,345 A | 12/2000 | Chudzik et al. | |
| 6,278,018 B1 | 8/2001 | Swan | |
| 6,514,734 B1 | 2/2003 | Clapper et al. | |
| 7,220,276 B1 | 5/2007 | Williams et al. | |
| 7,772,393 B2 | 8/2010 | Guire et al. | |
| 8,668,667 B2* | 3/2014 | Chappa | A61L 29/085 604/101.02 |
| 8,889,760 B2* | 11/2014 | Kurdyumov | A61L 17/145 523/105 |
| 2002/0004140 A1 | 1/2002 | Swan et al. | |
| 2002/0068804 A1 | 6/2002 | Hill et al. | |
| 2005/0244453 A1 | 11/2005 | Stucke et al. | |
| 2005/0287111 A1 | 12/2005 | Schlenoff et al. | |
| 2006/0105012 A1 | 5/2006 | Chinn et al. | |
| 2007/0003588 A1 | 1/2007 | Chinn et al. | |
| 2007/0292529 A1* | 12/2007 | Tabbiner | 424/601 |
| 2008/0063627 A1 | 3/2008 | Stucke et al. | |
| 2010/0096320 A1 | 4/2010 | Opperman | |
| 2010/0198168 A1 | 8/2010 | Rooijmans | |
| 2010/0226960 A1 | 9/2010 | Chudzik et al. | |
| 2010/0274012 A1 | 10/2010 | Guire et al. | |
| 2011/0046255 A1 | 2/2011 | Rooijmans | |
| 2011/0059874 A1 | 3/2011 | Rooijmans et al. | |
| 2011/0144373 A1 | 6/2011 | Swan et al. | |

(Continued)

FOREIGN PATENT DOCUMENTS

| | | | | | |
|---|---|---|---|---|---|
| DE | WO2008/003601 A1 * | 1/2008 | | ............... | C08K 5/00 |
| WO | WO2009097421 A1 * | 8/2009 | | ............... | C08J 3/02 |

OTHER PUBLICATIONS

Sumitomo Bakelite, LTD. Cell culture petri dishes product catalog-2010. https://www.sumibe.co.jp/english/product/s-bio/cell-culture/cell-culture-dish/spec/index.html.*
Chekmacheva et al. Phosphorylated Derivatives of Hydroxybenzophenones. Zhurnal Obshchei Khimii, vol. 53, No. 2, pp. 281-285, Feb. 1983.*
Taubenberger et al. The effect of unlocking RGD-motifs in collagen I on pre-osteoblast adhesion and differentiation. Biomaterials. Apr. 2010;31(10):2827-35.*
Cornwell et al. Extracellular matrix biomaterials for soft tissue repair. Clin Podiatr Med Surg. Oct. 2009;26(4):507-23.*
PCT Search Report for International Application No. PCT/US2013/048525 mailed on Oct. 16, 2013.
Johnson, G., et al., (2000) *Peptoid-containing collagen mimetics with cell binding activity*, Journal of Biomed Materials Research 51: 612-624.

(Continued)

*Primary Examiner* — Satyanarayana R Gudibande
*Assistant Examiner* — Jia-Hai Lee
(74) *Attorney, Agent, or Firm* — Kagan Binder, PLLC

(57) ABSTRACT

Cell attachment coatings for articles such as implantable medical devices and cell culture vessels are disclosed. The coatings include an intermediate coater layer which includes a phosphorous-containing component that is bonded in the coating by reacted photoreactive functional groups. The coating also include a second coated layer including an immobilized ECM protein or peptide that includes an active portion of an ECM protein that is able to serve as an outer layer to contact cells during use. The coatings promoted enhanced cell binding and growth.

20 Claims, 2 Drawing Sheets

(56) References Cited

U.S. PATENT DOCUMENTS

| | | | |
|---|---|---|---|
| 2011/0245367 A1* | 10/2011 | Kurdyumov | A61L 17/145 523/113 |
| 2012/0046384 A2 | 2/2012 | Kurdyumov et al. | |
| 2012/0149934 A1 | 6/2012 | Kurdyumov | |
| 2013/0143056 A1 | 6/2013 | Swan et al. | |

OTHER PUBLICATIONS

Kato, R., et al., (2006) *Peptide Array-Based Interaction Assay of Solid-Bound Peptides and Anchorage-Dependant Cells and Its Effectiveness in Cell-Adhesive Peptide Design*, Journal of Bioscience and Bioengineering 101: 485-95.

Keely, P.J. & Parise, L.V. (1996) *The $\alpha_2\beta_1$ Integrin Is a Necessary Co-receptor for Collagen-induced Activation of Syk and the Subsequent Phosphorylation of Phospholipase C$\gamma$2 in Platelets*, The Journal of Biological Chemistry 271: 26668-26676.

Koivunen, et al., (1994) *Isolation of a Highly Specific Ligand for the $\alpha_5\beta_1$ Integrin from a Phage Display Library*, The Journal of Cell Biology 124: 373-380.

Kotite, N. J. & Cunningham, L.W. (1986) *Specific Adsorption of a Platelet Membrane Glycoprotein by Human Insoluble Collagen*, The Journal of Biological Chemistry 261: 8342-8347.

Malinda, K.M., et al., (1999)*Identification of laminin $\alpha 1$ and $\beta 1$ chain peptides active for endothelial cell adhesion, tube formation, and aortic sprouting*, The FASEB Journal 13: 53-62.

Nomizu, et al., (1995) *Identification of Cell Binding Sites in the Laminin $\alpha 1$ Chain Carboxyl-terminal Globular Domain by Systematic Screening of Synthetic Peptides*, The Journal of Biological Chemistry 270: 20583-20590.

Pogany, G., et al., (1994) *The in vitro interaction of proteoglycans with type I collagen is modulated by phosphate*, Arch. Biochem. Biophys. 313: 102-111.—Abstract.

Reinholt, F.P., et al., (1990) *Osteopontin-apossible anchor of osteoclast to bone*, Proc. Natl. Acad. Sci. USA 87: 4473-4475.

Staatz, W.D., et at., (1991) *Identification of a Tetrapeptide Recognition Sequence for the $\alpha_2\beta_1$ Integrin in Collagen*, The Journal of Biological Chemistry 266: 7363-7367.

Yokosaki, Y., et al., (1999) *The Integrin $\alpha_9\beta_1$ Binds to a Novel Recognition Sequence (STIVYGLR) in the Thrombin-cleaved Amino-terminal Fragment of Osteopontin*, The Journal of Biological Chemistry 274: 36328-36334.

\* cited by examiner

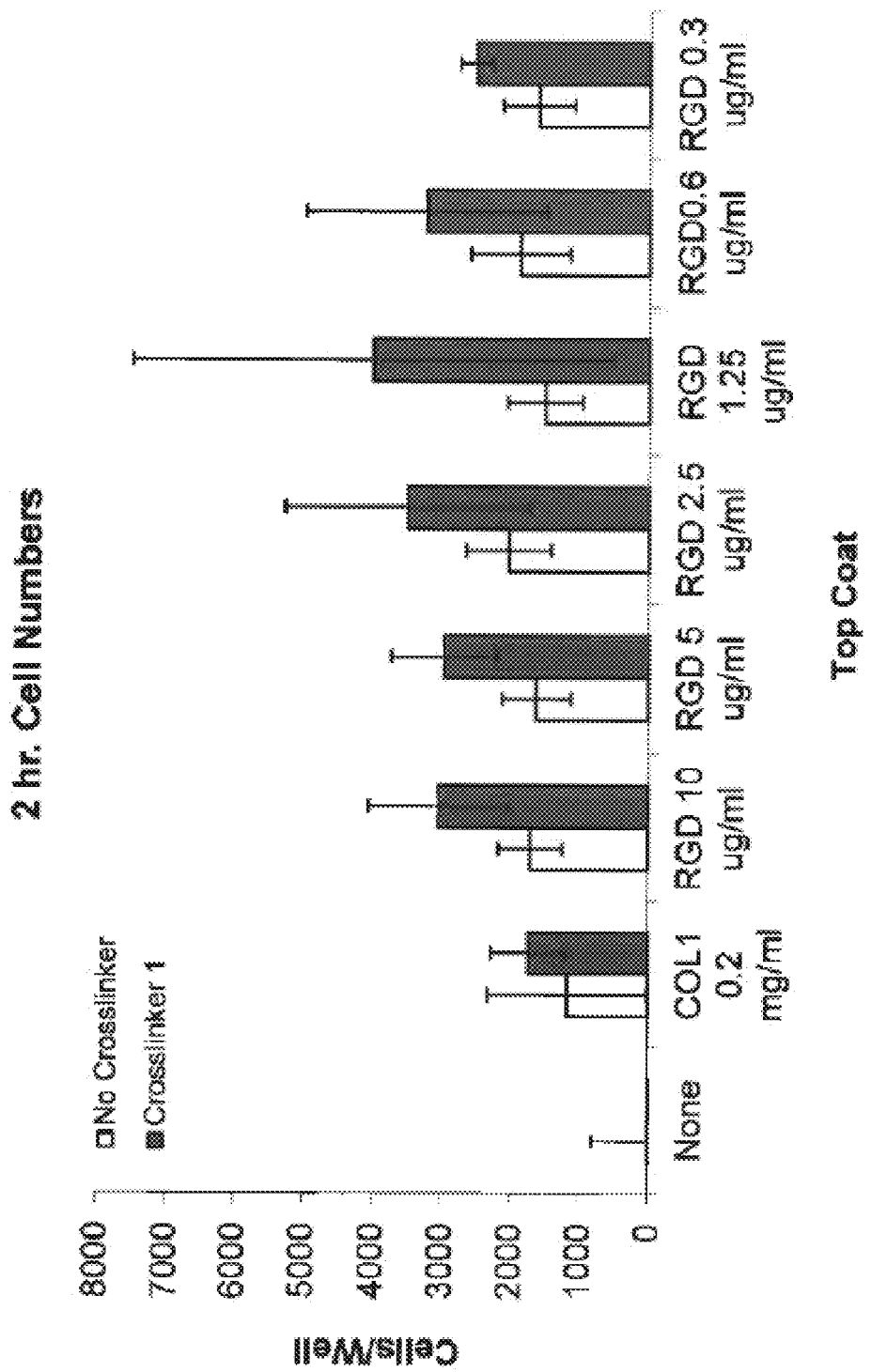

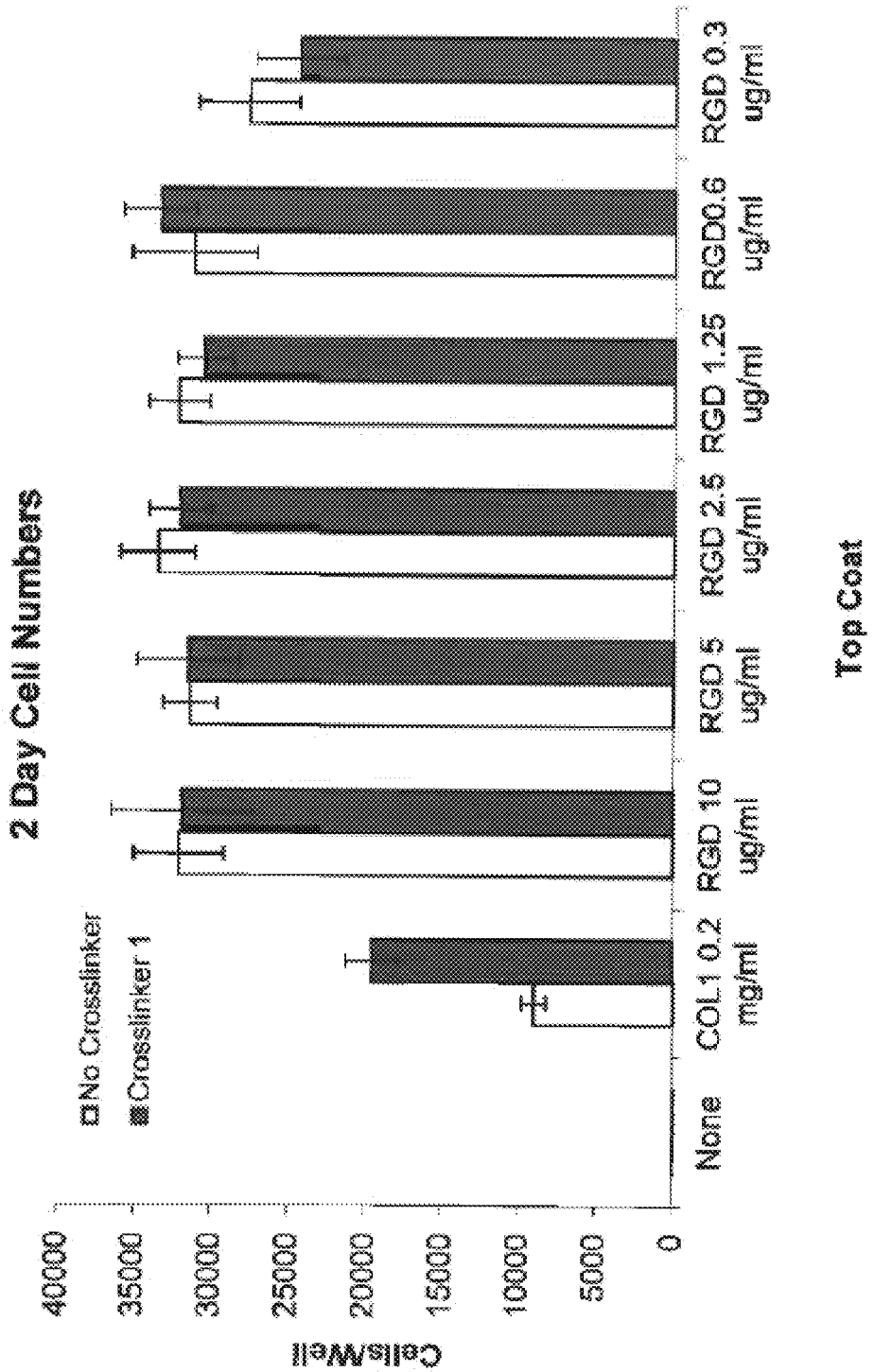

US 9,631,190 B2

CELL ATTACHMENT COATINGS AND METHODS USING PHOSPHOROUS-CONTAINING PHOTOREAGENT

CROSS-REFERENCE TO RELATED APPLICATION

The present non-provisional Application claims the benefit of commonly owned provisional Application having Ser. No. 61/666,516, filed on Jun. 29, 2012, entitled CELL ATTACHMENT COATINGS AND METHODS USING PHOSPHOROUS-CONTAINING CROSSLINKER, which Application is incorporated herein by reference in its entirety. Also, the entire contents of the ASCII text file entitled "SRM0141_Sequence_Listing_2_ST25.txt" created on May 5, 2014, having a size of 178 kilobytes is incorporated herein by reference.

FIELD OF THE INVENTION

The invention relates to cell attachment coatings for articles and methods for enhancing cell attachment to an article surface.

BACKGROUND OF THE INVENTION

Thin surface coatings on implantable medical articles have proved to be valuable in cases where it is desired to provide the article surface with a property that is not present on the uncoated surface. Polymeric coatings have been used to improve the wettability and lubricity of surfaces, and have also been used to present or elute drugs. For example, drugs presented on, or delivered from, the article surface can locally or systemically affect blood and vascular components thereby affecting bodily processes such as hemostasis and angiogenesis.

It has become appreciated that function of the implanted device at the site of implantation can be greatly enhanced by improving its compatibility in the context of the tissue response that occurs as a result of the implantation. Ideally, improved compatibility would allow surfaces of the implanted device to mimic natural tissue exposed by an injury and provide an environment for the formation of normal tissue as a result of the healing process. Polymeric coatings have been applied to surfaces of implantable devices in attempts to promote such tissue formation following implantation. Such surfaces would ideally attract components such as cells to the surface of the device and also promote proliferation of the cells for the formation of tissue.

Some polymeric coatings have been prepared using extracellular matrix proteins such as collagen as a coating material in attempts to attract cells to promote tissue growth on the coated surface. In the body, collagens have been shown to interact with various proteins including von Willebrand factor (VWF), integrins, and bone growth proteins. The direct or indirect result of these interactions can affect cell attachment and tissue formation. However, the process of mimicking the natural function of collagen on a synthetic surface is technically challenging. Preparation of collagen-containing coatings can often result in surfaces that do not provide the intended function following implantation. In coatings wherein collagen is not properly immobilized, collagen can leach out or be released from the surface, rendering the surface ineffective. Also, some chemistries for covalent immobilization of collagen may reduce or destroy collagen activity, such as by altering peptide motifs that are important for the interaction of collagen with other biological components. Certain chemistries may also alter the macromolecular configuration of collagen so that it does not resemble natural collagen. Further, even if collagen is successfully immobilized in a coating, the coating may have the ability to attract cells to a certain extent, but not in a manner that provides for subsequent proliferation of the cells, which is important for tissue formation.

The investigators have discovered that there is a need to prepare coatings that promote enhanced cell attachment and proliferation of cells on the coated surface, particularly of endothelial cells and fibroblasts and have discovered novel and inventive coatings that achieve these results. These cell types are useful for enhancing tissue growth around an implant.

SUMMARY

The present invention is directed to articles having biocompatible cell attachment coatings, and methods for forming these coatings. The coatings have an arrangement of coating components including a phosphorous-containing component with photoreactive groups, and a cell attachment component that is a cell attachment molecule comprising amino acids. The cell attachment molecule comprises an extracellular matrix (ECM) protein, or a peptide that includes an active portion of an ECM protein. The phosphorous-containing component is bonded in the coating using the photoreactive groups, resulting in the presentation of chemical groups which provide a distinct and improved cell attachment surface. Generally, the coatings promote enhanced attachment of cells on the coated surface of the article. In turn, this increases the number of proliferating cells on the device surface. In the body, these improved functional surfaces can enhance generation of tissue in association with the coated surface.

In some aspects, the coatings are formed on implantable medical articles, and these articles can be used in methods for the treatment of a medical condition. In the body this can promote the formation of tissue in association with the article. The enhanced cell attachment and proliferation improves integration of the implant in the body, and makes the implant more effective for medical use. The invention also contemplates the use of these coatings on cell culture articles and in vitro methods for enhancing cell attachment.

In one aspect, the invention provides an article comprising a biocompatible cell attachment coating. The coating includes an intermediate coated layer comprising a first component comprising a phosphorous-containing group and a bonding group comprising a photoreactive group, and the first component is immobilized in the coating via the bonding group. The coating also includes a second coated layer comprising a cell attachment molecule comprising an ECM protein, or a peptide that includes an active portion of an ECM protein, which is also immobilized in the coating. The intermediate coated layer is positioned between the second coated layer and a surface of the article. In use, the second coated layer is or becomes the outermost layer in the coating.

The coating can be formed by a method in which a first composition including the first component comprising the phosphorous-containing group and the bonding group is applied to a device surface. A second composition including the cell attachment molecule comprising amino acids, which is an ECM protein, or a peptide that includes an active portion of an ECM protein, is applied after the first composition is applied. The method also includes a step of irradiating the coating which can be performed after the first composition is applied, after the second composition is applied, or both. Irradiation of the bonding group causes its activation and covalent bonding to a target moiety and immobilization in the coating. The target moiety that reacts with the bonding group can be a component of the device surface, another first component, or the component selected from the ECM protein or peptide that includes an active portion of an ECM protein. The presentation of components in the coating achieved by irradiation and bonding using the bonding groups provides a particularly favorable presentation of coating components shown herein to enhance attachment of cells to the device surface.

Cell attachment studies associated with the invention revealed that the inventive coatings promoted a greater level of cell attachment to the coated surfaces over coatings using collagen alone, or the phosphorous-containing reagent alone. The enhanced cell attachment results were rather surprising considering that, in theory, the coating process should result in the phosphorous-containing reagent being buried under the collagen layer.

The coatings of the present invention can be formed on implantable medical articles such as, but not limited to, hernia meshes, aneurysm devices, and prosthetic devices such as coronary stents. Following implantation of the coated article in the body, the coating promotes an increased level of attachment of cells, such as endothelial cells and/or fibroblasts. Over time, tissue is formed on or around the coated implantable article. The natural tissue response can enhance integration, function, and lifetime of the implanted article.

The coatings of the present invention can be also formed on a cell culture article. Cells cultured on the coated cell culture article can be used for various purposes including in vitro testing or diagnosis, drug discovery, or for culturing cells that are introduced into the body.

BRIEF DESCRIPTION OF THE DRAWINGS

FIG. 1 is a graph of an in vitro endothelial cell attachment assay after two hours on plastic surfaces with (i) photoderivitized collagen or photoderivatized peptide (RGD) with no phosphorous-containing photoreagent, (ii) coated with photoderivatized collagen and phosphorous-containing photoreagent and (iii) coated with photoderivatized peptide (RGD) and phosphorous-containing photoreagent.

FIG. 2 is a graph of an in vitro endothelial cell attachment assay after two days on plastic surfaces with (i) photoderivitized collagen or photoderivatized peptide (RGD) with no phosphorous-containing photoreagent, (ii) coated with photoderivatized collagen and phosphorous-containing photoreagent and (iii) coated with photoderivatized peptide (RGD) and phosphorous-containing photoreagent.

DETAILED DESCRIPTION

The embodiments of the present invention described below are not intended to be exhaustive or to limit the invention to the precise forms disclosed in the following detailed description. Rather, the embodiments are chosen and described so that others skilled in the art can appreciate and understand the principles and practices of the present invention.

All publications and patents mentioned herein are hereby incorporated by reference. The publications and patents disclosed herein are provided solely for their disclosure. Nothing herein is to be construed as an admission that the inventors are not entitled to antedate any publication and/or patent, including any publication and/or patent cited herein.

Generally, the coatings of the present invention include at least an intermediate coated layer and a second coated layer. If there is no other coated layer between the second coated layer and the structural material of the article on which the coating is formed, the intermediate coated layer may also be referred to as the "first coated layer." The intermediate coated layer has a first component that includes a phosphorous-containing group as well as a bonding group. The bonding group includes a photoreactive group, such as an aryl ketone functional group, which is reacted to immobilize the first component in the coating by covalent reaction with the device surface or a coating material. The coating also includes a second coated layer comprising a cell attachment molecule comprising amino acids, which comprises an extracellular matrix (ECM) protein, or a peptide that includes an active portion of an ECM protein, which is also immobilized in the coating. The intermediate coated layer is positioned between the second coated layer and a surface of the article. The second coated layer is, or can become, the outer coated layer that contacts cells during use of the article.

The coatings were able to promote enhanced endothelial cell attachment and growth on culture plates and biomaterials. The endothelial cell and fibroblast attachment was improved over coatings made from either constituent component alone. The coatings also promoted a significant increase in cell proliferation after a few days of culturing.

The coatings and methods of the invention can be used to promote the formation of tissue in association with the coated surface of the article. In some aspects the process of tissue formation includes endothelialization. Endothelialization refers to the attachment and formation of a persistent layer of endothelial cells on the surface of an implanted medical device. The coatings can enhance the adherence of endothelial cells and the subsequent proliferation of these cells, which in turn leads to a well-formed and persistent endothelial cell layer. In the body, the endothelial cell coverage may also correlate with reduced proliferation of smooth muscle cells and extracellular matrix synthesis as promoted by binding of endothelial mitogens such as FGF-2, a reduced SMC IL-1 response, and/or anti-thrombotic effects. The cell responses promoted by the coating of the invention are beneficial, as they can reduce the rate of undesirable tissue responses that would otherwise lead to problems with integration of the device in the body. An implantable medical article with the coating of the invention can be introduced into a mammal for the prophylaxis or treatment of a medical condition. The coatings promote the formation of a mature endothelium in association with the article surface following a period of implantation. Mature endothelial cells can modulate other cellular responses, such as the proliferation of SMCs.

Endothelial cells are very flat, have a central nucleus, are about 1-2 μm thick and about 10-20 μm in diameter. Blood vessels and lymphatics are lined by endothelial cells; the layer being called the endothelium. Endothelial cells form flat, pavement-like patterns on the inside of the vessels and at the junctions between cells there are overlapping regions which help to seal the vessel. Endothelial cells are selective filters which regulate the passage of gases, fluid and various molecules across their cell membranes. Endothelial cells play a key role in angiogenesis, the development of new blood vessels from pre-existing vessels. Therefore, the coatings of the invention can promote the formation of new endothelial cell-derived tissue, including the formation of new blood vessels in the area of the implanted device.

Fibroblasts synthesize the extracellular matrix proteins, which are the structural framework for animal tissues, and play a key role in wound healing. Fibroblasts secrete the precursors of all the components of the extracellular matrix, primarily the ground substance and a variety of fibers, and are the most common cells of connective tissue in animals. Fibroblasts are morphologically heterogeneous with diverse appearances depending on their location and activity. Fibroblasts are derived from the mesenchyme, and express the intermediate filament protein vimentin, a feature used as a marker to distinguish their mesodermal origin. Therefore, the coatings of the invention can promote the formation of new tissue derived from fibroblasts, including the formation of new extracellular matrix in the area of the implanted device.

Various types of implantable medical articles can include a coating of the invention, and can be implanted at a target location in the body to provide a therapeutic effect to a subject.

One class of implantable articles is designed for wound and tissue defect treatments. Exemplary articles include hemostatic barriers; mesh and hernia plugs; patches, including uterine bleeding patches. Hernia meshes typically include a woven material made from a synthetic plastic-like material, such as polypropylene. Hernia meshes can be in the form of a patch which is placed in approximation to the tissue weakness, or in a hole in the tissue to effectively serve as a plug. In some embodiments, the mesh with coating can be soft and flexible to conform to tissue movement and placement at the target site. A coated mesh of the invention can be in hernia repair methods that involve tension-free or laparoscopic tension-free procedures. The coating on the mesh, in combination with the scaffolding structural feature of the woven material, provides an excellent surface for cell attachment and new tissue, which eventually incorporates the mesh into the area of mesh placement. Exemplary hernia meshes and medical processes for hernia repair are described in U.S. Pat. No. 4,769,038 (C. R. Bard), U.S. Pat. No. 5,569,273 (C. R. Bard), and U.S. Pat. No. 5,769,864 (Surgical Sense).

Mesh or non-mesh support implants including a coating of the invention can also be used in a procedure to correct a condition of the urogenital tract. Mesh implants are well known in the art for the treatment of conditions such as stress urinary incontinence and vaginal prolapse (see, for example, U.S. Pat. Nos. 5,836,315, 6,306,079, 6,689,047, and 7,083,637).

Another class of implantable articles is designed for cardiovascular treatment. Exemplary implantable cardiovascular articles include vascular implants and grafts, grafts, vascular prostheses including stents, endoprosthesis, stent-graft (such as abdominal aortic aneurysms (AAA) stent-grafts), and endovascular-stent combinations; small diameter grafts, abdominal aortic aneurysm grafts; atrial septal defect (ASD) patches, patent foramen ovale (PFO) patches, ventricular septal defect (VSD) patches, pericardial patches, epicardial patches, and other generic cardiac patches; pericardial sacks; ASD, PFO, and VSD closure devices; mitral valve repair devices; heart valves, venous valves, aortic filters; venous filters; left atrial appendage filters; valve annuloplasty devices; implantable electrical leads, including pacemaker and implantable cardioverter defibrillator (ICD) leads; and cardiac sensors.

Other implantable devices include ophthalmic devices, such as intraocular lenses.

Other implantable devices include those for the treatment of aneurysms, such as flow diverters, neuroaneurysm patches; neuroaneurysm coils; and aneurysm exclusion devices.

Other exemplary devices include self-expandable septal occluders, patent ductus arteriosus (PDA) occluders, and patent foramen ovale (PFO) occluders. The occluders can be constructed from nitinol wire mesh and filled or associated with polyester fabric (available from, for example, AGA Medical, Golden Valley, Minn.).

A medical article having a cell attachment coating can also be prepared by assembling an article having two or more "parts" (for example, pieces of a medical article that can be put together to form the article) wherein at least one of the parts has the coating. All or a portion of the part of the medical article can have a coating with the intermediate and second coated layers as described herein. In this regard, the invention also contemplates parts of medical articles (for example, not the fully assembled article) that have a coating of the present invention.

The biocompatible cell attachment coating can also be formed on a surface of a cell culture vessel. A "cell culture vessel" is an example of a cell culture article and, as used herein, means a receptacle that can contain media for culturing a cell or tissue. The cell culture vessel may be glass or plastic. Preferably the plastic is non-cytotoxic. Exemplary cell culture vessels include, but are not limited to, single and multi-well plates, including 6 well and 12 well culture plates, and smaller welled culture plates such as 96, 384, and 1536 well plates, culture jars, culture dishes, petri dishes, culture flasks, culture plates, culture roller bottles, culture slides, including chambered and multi-chambered culture slides, culture tubes, coverslips, cups, spinner bottles, perfusion chambers, bioreactors, and fermenters.

Optionally, an implantable medical article or a cell culture vessel can be associated with a "nanofibrillar structure," which refers to a mesh-like network of nanofibers. A nanofibrillar structure can be a cell culture article and can be included in any sort of cell culture apparatus wherein cell attachment is desired, or where a cell culture process is performed. In many cases an article includes a network of nanofibers in addition to one or more other non-nanofiber materials. For example, a nanofibrillar structure can include a network of nanofibers on a support, wherein the support is fabricated from a material that is different than the nanofibers. The biocompatible cell attachment coating can be formed on a surface of the nanofibers, or on another portion of the article.

The article or device on which the cell attachment coating is formed can be formed from natural polymers, synthetic polymers, metals, ceramics, or combinations thereof. In some cases, combinations of any of these general classes of materials can be used to form the article, such as an implantable medical device. These materials can be described as "structural materials" that form the body member of the article. In other words, structural materials can provide the article with its three-dimensional structure.

In some cases, one or more of the material(s) of the article or device can serve as a target for covalent bonding to the activated photoreactive group. Suitable materials generally are a good source of abstractable hydrogens. Using these materials, the excited state of a photoactivated aryl ketone functional group can insert into a carbon-hydrogen bond by abstraction of a hydrogen atom from the structural material of the article, thus creating a radical pair. Subsequent collapse of the radical pair leads to formation of a new carbon-carbon bond, and covalent bonding of the first component of the coated layer to the structural material of the article.

Many plastic articles, such as those formed from synthetic polymers, can provide a good source of abstractable hydrogens. Exemplary synthetic polymers, such as oligomers, homopolymers, and copolymers resulting from addition, condensation, or ring opening polymerizations can be structural materials of the article. Examples of suitable addition polymers include, but are not limited to, acrylics such as those polymerized from methyl acrylate, methyl methacrylate, hydroxyethyl methacrylate, hydroxyethyl acrylate, acrylic acid, methacrylic acid, glyceryl acrylate, glyceryl methacrylate, methacrylamide, and acrylamide; vinyls such as ethylene, propylene, vinyl chloride, vinyl acetate, vinyl pyrrolidone, and vinylidene difluoride. Examples of condensation or ring-opened polymers include, but are not limited to, nylons such as polycaprolactam, polylauryl lactam, polyhexamethylene adipamide, and polyhexamethylene dodecanediamide, and also polyurethanes, polycarbonates, polyamides, polysulfones, poly(ethylene terephthalate), polydimethylsiloxanes, and polyetherketone.

Other plastic articles, such as those formed from halogenated polymers, for example, chlorinated and/or fluorinated polymers, may have surfaces that are poorly reactive or non-reactive with the photoreactive group, such as an activated aryl ketone functional group. If these surfaces are not modified, or if a reactive base coat is not a part of the coating, activation of the photoreactive groups can result in bonding between materials of the intermediate coated layer, which may provide a better source of abstractable hydrogen atoms as compared to the substrate surface. In this case, for example, covalent bonds may be formed between the activated photoreactive group and material in the intermediate coated layer.

Examples of polymers that provide a poorly reactive, or non-reactive surface include perfluoroalkoxy (PFA) polymers, such as Teflon™ and Neoflon™; polychlorotrifluoroethylene (PCTFE); fluorinated ethylene polymers (FEP), such as polymers of tetrafluoroethylene and hexafluoropropylene; poly(tetrafluoroethylene) (PTFE); and expanded poly(tetrafluoroethylene) (ePTFE).

Implantable articles that are formed from a metal or combination of metals generally have surfaces that are poorly reactive or non-reactive with an activated photoreactive group. In some embodiments, metal surfaces can be chemically modified or provided with a base coat where the photoreactive group is bonded to, or towards, the article surface.

Metals that can be used to form the implantable article include platinum, gold, or tungsten, as well as other metals such as rhenium, palladium, rhodium, ruthenium, titanium, nickel, and alloys of these metals, such as stainless steel, titanium/nickel, nitinol alloys, cobalt chrome alloys, non-ferrous alloys, and platinum/iridium alloys. One exemplary alloy is MP35. Metal can also be used as structural material for forming cell culture vessels, and the coatings of the invention can be formed on the vessels surface.

In some embodiments, if the structural material of the implantable or cell culture article is poorly reactive or non-reactive with the activated photoreactive group, a base coat can optionally be formed on the article surface. The base coat can be positioned between the article surface and the intermediate coated layer. Exemplary base coats include polymeric compounds such as Parylene™, or silane-containing compound, such as hydroxy- or chloro-silane.

Parylene™ (poly(para-xylylene) base layers are typically very thin (0.1 micron to 75 microns), continuous, inert, transparent, and conformal films. Parylene™ is applied to substrates in an evacuated deposition chamber by a process known as vapor deposition polymerization (VDP). This involves the spontaneous resublimation of a vapor that has been formed by heating di-para-xylylene, which is a white crystalline powder, at approximately 150° C., in a first reaction zone. The vapor resulting from this preliminary heating is then cleaved molecularly, or pyrolized, in a second zone at 650° C. to 700° C. to form para-xylylene, a very reactive monomer gas. This monomer gas is introduced to the deposition chamber, where it resublimates and polymerizes on substrates at room temperature and forms a transparent film. In the final stage, para-xylylene polymerizes spontaneously onto the surface of objects being coated. The coating grows as a conformal film (poly-para-xylylene) on all exposed substrate surfaces, edges and in crevices, at a predictable rate. Parylene™ formation is spontaneous, and no catalyst is necessary. A process for forming a Parylene™ base layer on the surface of a metal stent is described in detail in U.S. Publication No. 2005/0244453 (Nov. 3, 2005; Stucke et al.).

In one mode of practice, an optional base coat of Parylene is formed on the article surface, followed by disposing a composition that includes a first component comprising a phosphorous-containing group and a bonding group comprising an photoreactive group. The applied first component is then irradiated, which results in covalent bonding to the Parylene material.

Other base coats can include synthetic polymers formed from acrylamide, vinyl pyrrolidone, or acrylic acid residues (e.g., poly(acrylamide) or poly(vinyl pyrrolidone)). These polymers can optionally include pendent photoreactive groups such as described in U.S. Pat. No. 6,007,833.

In some embodiments the photoreactive group comprises an aryl ketone functional group. Aryl ketone functional groups refer to those groups having the base structure of:

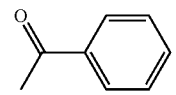

Aryl ketone functional groups include acetophenone, benzophenone, anthraquinone, anthrone, and anthrone-like heterocycles (for example, heterocyclic analogs of anthrone such as those having nitrogen, oxygen, or sulfur in the 10-position), or their substituted (for example, ring substituted) derivatives can be used. Those functional groups containing two aryl groups can be referred to as diaryl ketone functional groups. Examples of aryl ketones include heterocyclic derivatives of anthrone, including acridone, xanthone, and thioxanthone, and their ring substituted derivatives. Some photoreactive groups include thioxanthone, and its derivatives, having excitation energies greater than about 360 nm.

These types of photoreactive groups, such as aryl ketones, are readily capable of undergoing the activation/inactivation/reactivation cycle described herein. In some embodiments benzophenone can be the photoreactive group. Benzophenone can be capable of photochemical excitation with the initial formation of an excited singlet state that undergoes intersystem crossing to the triplet state. The excited triplet state can insert into carbon-hydrogen bonds by abstraction of a hydrogen atom (from a support surface, for example), thus creating a radical pair. Subsequent collapse of the radical pair leads to formation of a new carbon-carbon bond. If a reactive bond (for example, carbon-hydrogen) is not available for bonding, the ultraviolet light-induced excitation of the benzophenone group is reversible and the molecule returns to ground state energy level upon removal of the energy source.

In some aspects, the first component is a non-polymeric compound comprising a phosphorous-containing group and at least one bonding group comprising a photoreactive group. An exemplary photoreactive group comprises an aryl ketone functional group, such as a diaryl ketone functional group. In some cases, the non-polymeric compound has a nonpolymeric core molecule comprising a phosphorous atom, the core phosphorous atom having attached thereto, either directly or indirectly, two or more substituents with an aryl ketone group. Use of some non-polymeric compounds can provide an intermediate coated layer with a very high density of phosphorous-containing groups, and can thereby allow the formation of a very thin intermediate coated layer.

In another embodiment, the phosphorous-containing group includes one or more phosphorous atoms. In one embodiment, the phosphorous-containing group includes one phosphorus atom (which can also be referred to as a mono-phosphorus linking group). In another embodiment, the phosphorous-containing agent includes two phosphorus atoms (which can also be referred to as a bis-phosphorus linking group). In one embodiment, the phosphorous-containing group comprises at least one phosphorus atom with a phosphorus-oxygen double bond (P=O), wherein at least one or two photoreactive groups are bound to the phosphorus atom. In another embodiment, the phosphorous-containing group comprises one phosphorus atom with a phosphorus-oxygen double bond (P=O), wherein two or three photoreactive groups are covalently bound to the phosphorus atom. In another embodiment, the phosphorous-containing group comprises at least two phosphorus atoms, wherein at least one phosphorus atom includes a phosphorus-oxygen double bond (P=O), and at least one or two photoreactive groups are covalently bound to each phosphorus atom.

In a more particular embodiment, the phosphorous-containing agent can be represented by the formula:

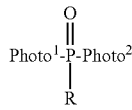

wherein Photo¹ and Photo², independently, represent one or more photoreactive groups, wherein the phosphorous-containing agent comprises a covalent linkage between at least one photoreactive group and the phosphorous-containing group, wherein the covalent linkage between at least one photoreactive group and the linking group is interrupted by at least one heteroatom and R is alkyl or aryl, a photoreactive group, hydroxyl or salt thereof, or a combination thereof. In one embodiment, the hydroxyl salt includes a counterion that is lithium, sodium, potassium, or a combination thereof. In a more particular embodiment, R is cyclic, linear or branched, saturated or unsaturated, aromatic or heteroaromatic, or a combination thereof. In a more particular embodiment, R is phenyl, methyl, ethyl, isopropyl, t-butyl, or a combination thereof.

In another embodiment, the phosphorous-containing group can be represented by formula:

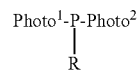

wherein Photo¹ and Photo² independently, represent one or more photoreactive groups, wherein the phosphorous-containing agent comprises a covalent linkage between at least one photoreactive group and the phosphorous-containing group, wherein the covalent linkage between at least one photoreactive group and the phosphorous-containing group is interrupted by at least one heteroatom and R is alkyl or aryl, a photoreactive group (wherein the covalent linkage between the photoreactive group and the phosphorous-containing group may be interrupted by at least one heteroatom), hydroxyl or salt thereof, or a combination thereof. In one embodiment, the hydroxyl salt includes a counterion that is lithium, sodium, potassium, or a combination thereof. In a more particular embodiment, R is cyclic, linear or branched, saturated or unsaturated, aromatic or heteroaromatic, or a combination thereof. In one embodiment, R is phenyl, methyl, ethyl, isopropyl, t-butyl, or a combination thereof.

In another embodiment, the phosphorous-containing agent can be represented by the formula:

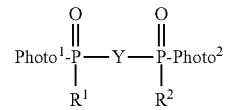

wherein Photo¹ and Photo², independently, represent one or more photoreactive groups, wherein the phosphorous-containing agent comprises a covalent linkage between at least one photoreactive group and the phosphorous-containing group, wherein the covalent linkage between at least one photoreactive group and the phosphorous-containing group is interrupted by at least one heteroatom; Y represents a linker that can be null (i.e., not present, such that the linking group includes a direct P—P bond), N or O, linear or branched $C_1$-$C_{10}$ alkyl, or a combination thereof; and $R^1$ and $R^2$ are independently alkyl, aryl, a photoreactive group (wherein the covalent linkage between the photoreactive group and the phosphorous-containing group can be interrupted by at least one heteroatom), hydroxyl or salt thereof, or a combination thereof. In one embodiment, Y is selected from O, $CH_2$, $OCH_2O$, $OCH_2CH_2O$ and $O(CH_2CH_2O)_n$, wherein n is an integer between 1 and 5, between 1 and 10, between 1 and 15, between 1 and 20, between 1 and 25, or between 1 and 30. In one embodiment, the hydroxyl salt counterion is lithium, sodium, potassium, or a combination thereof. In a more particular embodiment, $R^1$ and $R^2$ are independently, cyclic, linear or branched hydrocarbon, saturated or unsaturated, aromatic or heteroaromatic, or a combination thereof. In one embodiment, $R^1$ and $R^2$ are independently phenyl, methyl, ethyl, isopropyl, t-butyl, or a combination thereof. In general, a longer hydrocarbon chain between the two phosphorus atoms will tend to increase the flexibility of the linking agent and may facilitate crosslinking between a greater number of molecules in the coating, or molecules in the coating and the device surface, than a linking agent with a shorter carbon chain, since the reactive photoreactive groups can react with molecules located farther apart from one another. In one embodiment, Y can be O, $CH_2$, $OCH_2CH_2O$ and $O(CH_2CH_2O)_n$ wherein n is an integer between 1 and 5, between 1 and 10, between 1 and 15, between 1 and 20, between 1 and 25, or between 1 and 30. One embodiment is shown below

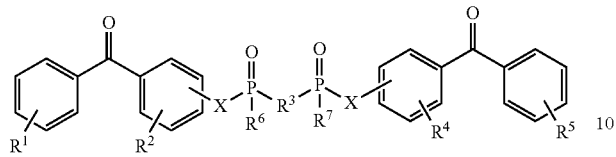

in which $R^1$, $R^2$, $R^4$ and $R^5$ can be any substitution, including but not limited to H, alkyl, halogen, amine, hydroxyl, or a combination thereof; $R^3$ can be any substitution, including but not limited to O, alkyl, or a combination thereof; and each X can independently be O, N, Se, S, alkyl, or a combination thereof. In one embodiment, the phosphorous-containing agent includes one or more phosphorester bonds and one or more phosphoramide bonds, and can be represented by the formula:

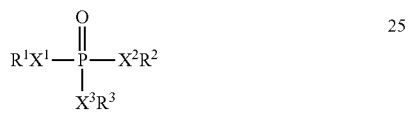

wherein X and $X^2$ are, independently, O, N, Se, S, or alkyl; $R^1$ and $R^2$ are independently, one or more photoreactive groups, and $X^3$ is O, N, Se, S, alkyl or aryl; $R^3$ is alkyl or aryl, including, but not limited to cyclic, linear or branched, saturated or unsaturated, aromatic or heteroaromatic, or a combination thereof. In a more particular embodiment, $R^3$ is phenyl, methyl, ethyl, isopropyl, t-butyl, or a combination thereof. $R^3$ can also be a photoreactive group or a hydroxyl or salt thereof. In one embodiment, the hydroxyl salt counterion is lithium, sodium, potassium, or a combination thereof.

In one embodiment, the phosphorous-containing agent comprises a triphosphorester, which can be represented by the formula.

wherein $R^1$ and $R^2$ are independently, one or more photoreactive groups, and $R^3$ is alkyl or aryl, including, but not limited to cyclic, linear or branched, saturated or unsaturated, aromatic or heteroaromatic, or a combination thereof. In a more particular embodiment, $R^3$ is phenyl, methyl, ethyl, isopropyl, t-butyl, or a combination thereof. $R^3$ can also be a photoreactive group or hydrogen, or a hydroxyl salt. In one embodiment, the hydroxyl salt counterion is lithium, sodium, potassium, or a combination thereof.

Some specific embodiments include the following phosphorous-containing agents:

(a) bis(4-benzoylphenyl)hydrogen phosphate:

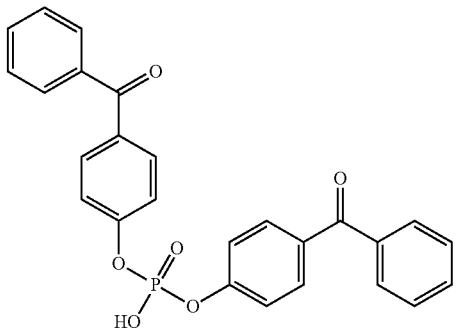 [SMILES: O=C(c1ccccc1)c1ccc(OP(=O)(O)Oc2ccc(C(=O)c3ccccc3)cc2)cc1]

(b) sodium bis(4-benzoylphenyl) phosphate:

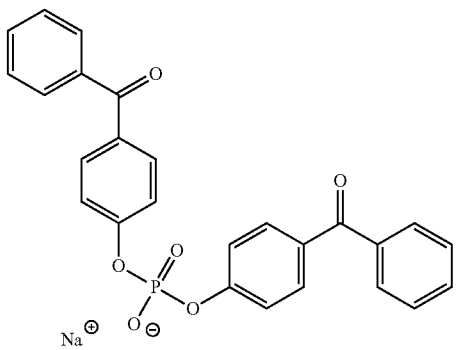 [SMILES: O=C(c1ccccc1)c1ccc(OP(=O)([O-])Oc2ccc(C(=O)c3ccccc3)cc2)cc1 ; [Na+]]

(c) tris(4-benzyolphenyl) phosphate:

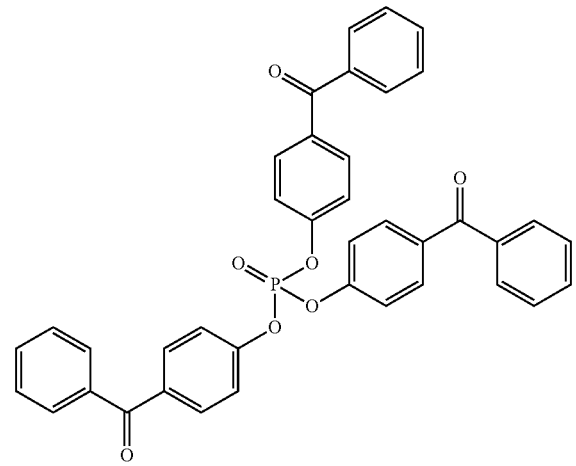 [SMILES: O=C(c1ccccc1)c1ccc(OP(=O)(Oc2ccc(C(=O)c3ccccc3)cc2)Oc2ccc(C(=O)c3ccccc3)cc2)cc1]

(d) tetrakis(4-benzoylphenyl)methylenebis(phosphonate)

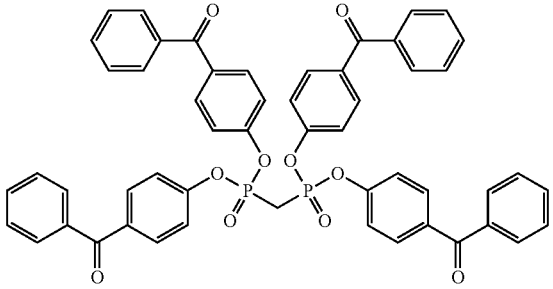 [SMILES: O=C(c1ccccc1)c1ccc(OP(=O)(CP(=O)(Oc2ccc(C(=O)c3ccccc3)cc2)Oc2ccc(C(=O)c3ccccc3)cc2)Oc2ccc(C(=O)c3ccccc3)cc2)cc1]

In another embodiment, the phosphorous-containing agent comprises a triphosphoramide, which can be represented by the formula.

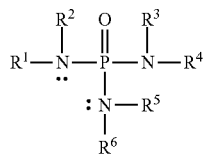

wherein $R^1$-$R^6$ are independently, a photoreactive group, a hydroxyl or salt thereof, alkyl or aryl, or a combination thereof, wherein at least two of $R^1$-$R^6$ are, independently, a photoreactive group. In one embodiment, the hydroxyl salt counterion is lithium, sodium, potassium, or a combination thereof. In a more particular embodiment, $R^1$-$R^6$ are independently cyclic, linear or branched, saturated or unsaturated, aromatic or heteroaromatic, or a combination thereof. In a more particular embodiment, $R^1$-$R^6$ are, independently, phenyl, methyl, ethyl, isopropyl, t-butyl, or a combination thereof.

Non polymeric compounds having at least one phosphorous-containing group and two or more aryl ketone groups can be prepared in methods as described in U.S. Patent Publication 2012/0046384 (Kurdyumov, et al.).

The amount of the phosphorous-containing group can also be expressed in terms of molar quantity phosphorus per gram of first (non-polymeric) compound. Exemplary ranges are from about 1 mmol/g to about 7 mmol/g, about 2.5 mmol/g to about 7 mmol/g, or even about 4 mmol/g to about 6.5 mmol/g.

A coating composition including a first (non-polymeric) compound having phosphorous-containing and photoreactive functional groups, such as aryl ketone groups, can be prepared and applied to a substrate surface to form the intermediate coated layer. Suitable solvents include water, and other aqueous buffers. Exemplary amounts of the non-polymeric compound in the coating composition are in the range of about 0.1 mg/mL to about 5 mg/mL, or about 0.25 mg/mL to about 1 mg/mL.

The coating process to form the intermediate coated layer can be performed using any one of a variety of methods. The coating method chosen can depend on one or more factors, such as the article that is coated, and/or the properties of the coating composition. In some modes of practice, the first component with the phosphorous-containing group and photoreactive functional group can be the primary component in the coating, and there may be no other, or insignificant amounts of other solid materials in the intermediate coated layer.

In some modes of practice, the coating process involves placing the coating materials in contact with the device surface, or device surface that has been pretreated with a base coat. For example, the coating materials can be applied to a surface and dried down, or partially dried down, and then the coating materials are irradiated. The process of applying can be performed using any one of a variety of techniques.

One exemplary method for applying the coating composition is by dip-coating. A typical dip-coating procedure involves immersing the article to be coated in the first coating composition, dwelling the object in the composition for a period of time (a standard time is generally less than about 30 seconds, and can even be less than about 10 seconds in many cases), and then removing the article from the composition. After the article has been dip-coated in the coating solution, it is removed and dried, or partially dried. Drying can be carried out using any suitable method, including air-drying the dip coated article. Times up to 30 minutes can be sufficient to dry the coated article although shorter times may be also sufficient.

Other methods such as brushing, swabbing, or painting the first coating composition on the surface of the article can be performed to provide the intermediate coated layer. Alternatively, the first coating composition can be spray coated onto the surface of the article. An exemplary spray coating process and apparatus that can be used for coating implantable medical articles using the compositions of the present invention is described in U.S. Pat. No. 7,192,484 (Chappa et al.).

In other modes of practice, a liquid coating composition is applied to the article surface and then the article is irradiated while the liquid is in contact with the surface. In this mode of practice, the coating process is performed without drying down the coating solution on the surface of the substrate prior to the step of irradiating. For example, in solution, irradiation of cell culture articles can be performed by filling a well or the cell culture article with the liquid coating solution and then irradiating the well. In-solution coating can be performed to provide the intermediate coated layer to an implantable medical device as well. Such methods can provide a very thin intermediate coated layer of material on the article surface (see, for example, U.S. Pub No. 2010/0096320).

In some modes of practice, a step in the coating process involves irradiating the coating materials used to form the intermediate coating layer prior to applying the composition used to form the second coated layer. The process can involve irradiation of the coating materials with UV light at a wavelength and amount in order to activate at least a portion of the photoreactive groups, such as the aryl ketone functional groups, to an excited state and cause their bonding to a target moiety. "Partial irradiation" involves irradiating the coating materials with a dose of irradiation so that a portion of the photoreactive groups bond to target moieties, such as atoms of the device surface of other portions of components in the intermediate coated layer. Such irradiation can therefore result in "partial bonding" of the photoreactive groups in the intermediate coated layer. One advantage of this approach is that the intermediate coated layer can be irradiated in a subsequent step to affect bonding of the unreacted photoreactive groups to another target moiety. For example, after materials that form the second coated layer are applied on the intermediate coated layer, the coating can again be irradiated to cause bonding of the photoreactive groups in the intermediate layer to the ECM protein or peptide that includes an active portion of an ECM protein, in the second coated layer. In this regard, reactive chemistries in the composition that forms the outer coated layer may not be required, but optional.

In other modes of practice, the materials of the intermediate coated layer are fully irradiated, meaning that all, or substantially all, of the photoreactive groups are reacted and bonded to one or more target moieties.

Generally, aryl ketone functional groups are activated by UV radiation in the range of 330 nm to 340 nm. Light sources that provide output radiation sufficient to activate the photoreactive groups and promote formation of the coating can be used. Suitable light sources can incorporate, for example, metal halide bulbs, or other suitable bulbs that provide an activating source of irradiation. One suitable light source is a Dymax BlueWave™ Spot Cure System, which is commercially available from Dymax Corp. (Torrington, Conn.).

The amount of energy that is applied to the surface can vary depending on a number of factors, including the type and amount of first (non-polymeric) photoreactive group-containing compound used, the substrate material, and the type and amount of coating composition. In some aspects an amount of energy in the range of about 5 mJ/cm$^2$ to about 5000 mJ/cm$^2$ as measured at 335 nm, is applied to the surface; a more preferable range is from about 50 mJ/cm$^2$ to about 500 mJ/cm$^2$. Other ranges can be used in conjunction with the step of forming the coating. Partial bonding of the photoreactive groups in the intermediate coated layer may be accomplished using amounts of energy in the lower ends of these ranges.

In one mode of practice, the coating is illuminated for 60 seconds using an ultraviolet Dymax™ Cure System at a distance of 20 cm. This distance and time can provided a coating with approximately 100 mJ/cm$^2$ in the wavelength range 330-340 nm.

The second coated layer of the article includes a cell attachment molecule comprising amino acids, which is an extracellular matrix (ECM) protein, or a peptide that includes an active portion of an ECM protein. As known in the art, ECM proteins provide structural support to cells and/or attach cells that reside in the ECM. Molecules on the surface of cells, such as integrins, carbohydrates, and other cell adhesion molecules can interact with ECM proteins to promote cell attachment. Exemplary ECM proteins include fibronectin, laminin, collagen, procollagen, elastin, vitronectin, tenascin, entactin, fibrinogen, thrombospondin, osteopontin (bone sialoprotein), osteocalcin, von Willibrand Factor, and active domains thereof.

An "active portion" (or "active domain") of an ECM protein refers to an amino acid sequence found within the ECM protein that, in itself, provides function according to one or more properties of the ECM protein, such as providing structural support to cells and/or for attaching cells. The active portion may also be referred to as a "domain" or "motif." The peptide that includes an active portion of an ECM protein can have a "core sequence" of amino acid residues, and optionally one or more additional amino acid residues that flank (i.e., on the C-terminus, N-terminus, or both) the core sequence. The one or more additional amino acids that flank the core sequence can correspond to the wild type ECM sequence in the relevant region of the protein, or can be an amino acid(s) that diverges from the wild type sequence (e.g., a "variant amino acid or sequence"). The variant amino acid or sequence can be one that enhances properties of the peptide, such as providing enhanced ligand interaction, and/or can facilitate formation of the second coated layer.

Active portions of ECM proteins are known in the art or can be determined using routine experimentation by carrying out assays that are commercially or described in a reference. For example, cell attachment assays which utilize peptides or proteins adhered to plastic or covalently immobilized on a support have been described and can be used to determine the activity of a desired peptide for promoting attachment of cells (see, for example, Malinda, K. M., et al. (1999) FASEB J. 13:53-62; or Kato, R., et al. (2006) J. Biosci. Bioeng. 101:485-95).

As used herein, a "peptide" is a short polymer of 25 or less amino acids linked by peptide bonds. As used herein, a "polypeptide" is a polymer of more than 25 amino acids linked by peptide bonds and which includes full length proteins. A peptide having an active portion of an ECM protein can be synthesized by solid phase peptide synthesis (SPPS) techniques using standard techniques, such as Fmoc synthesis. See, for example, Carpin, et al. (1970), J. Am. Chem. Soc. 92:5748-5749. Peptides described herein are also commercially available.

In one aspect of the invention type I collagen (collagen I) is present in the outer coated layer. Type I collagen is the most common of the collagens in vertebrates and makes up to 90% of the skeletons of the mammals, and also found in scar tissue, tendons, skin, artery walls, fibrocartilage, and bones and teeth. COL1A1 is the human gene that encodes collagen I, alpha 1 (1464 AA), with an accession reference number P02452 (CO1A1_HUMAN; SEQ ID NO:55) in UniProtKB/Swiss-Prot. The human sequence shares at least 90% sequence identity with, at least, chimpanzee (H2QDE6_PANTR; SEQ ID NO:56), dog (Q9XSJ7; CO1A1_CANFA; SEQ ID NO:57), and cow (P02453; SEQ ID NO:58).

Type I procollagen is similar to other fibrillar collagens and has three polypeptide chains (α-chains) which form a unique triple-helical structure. It is a heterotrimer of two α1(I) and one α2(I) chains. Among species, the α1(I) chain is more conserved than the α2(I) chain (Kimura 1983). Type I collagen molecule contains an uninterrupted triple helix of approximately 300 nm in length and 1.5 nm in diameter flanked by short nonhelical telopeptides. The helical region is highly conserved among species (Chu et al. (1984) *Nature* 310:337-340).

Collagen peptides can also be used in the outer coating. Such peptides include RGD, YIGSR (SEQ ID NO:1), and (GPN1) repeats (see, for example, Johnson, G. (2000) J. Biomed. Mat. Res., 51:612-624). Collagen peptides, as well as other peptides that include a portion of an ECM protein, can be in linear or cyclic form (e.g., commercially available from Peptides International, Inc., Louisville, Ky.).

Recombinant collagen, such as recombinant human collagen, can be used to prepare the coatings. Recombinant collagen can be expressed in single cell organisms, such as yeast, in which collagen chains are expressed from a transgenic nucleic acid sequence. Recombinant human collagen I and human collagen III are commercially available (e.g., from FibroGen, Inc. San Francisco, Calif.), and can be prepared from human proalpha1(I), proalpha2(I) and both alpha and beta subunits of prolyl hydroxylase genes co-expressed in *Pichia pastoris*, and converted into mature collagen (from procollagen I) by proteinase digestion. Human proalpha1 (III) can be expressed and digested in the same way to prepare mature collagen (from procollagen III).

Atelocollagen can be used to prepare the coatings. Atelocollagen can be prepared by removing antigenic telopeptides at each end of a collagen I molecule using a proteolytic enzyme, such as pepsin. Removal of the telopeptides generally improve solubility of the collagen, and render it soluble in an acidic solution (e.g., in the range of about 3.0 to 4.5) Atelocollagen can be prepared from collagen from an animal source, such as from porcine tissue. Methods for the preparation of atelocollagen are known in the art (see, for example, U.S. Pat. Nos. 3,949,073 and 4,592,864) and are also commercially available under the tradename Theracol™ (Regenerative Medical Systems, Hertfordshire, UK).

Hydrolyzed collagen (also known as gelatin) can also be used to prepare the coatings. Gelatin is formed from the hydrolysis of collagen using heat, and/or acid or alkali solutions, and results in collagen polypeptides or peptides that have a lower molecular weight than collagen. Recombinant gelatins having sizes of 100 kDa or 8.5 kDa are commercially available (e.g., from FibroGen, Inc. San Francisco, Calif.).

Peptides derived from a collagen sequence can also be used in the outer coating. Exemplary collagen peptides comprise the sequences DGEA (SEQ ID NO:2), KDGEA (SEQ ID NO:3), GER, and GFOGER (SEQ ID NO:4) (see, for example, Keely, P. J., and Parise, L. V. (1996) J Biol. Chem. 271:26668-26676; Kotite, N. J., and Cunningham, L. W. (1986) J Biol. Chem. 261:8342-8347; and Staatz, W. D., et al. (1991) J Biol. Chem. 266:7363-7367).

In some aspects of the invention the coating includes a laminin, or an active portion thereof. The laminin protein family includes multidomain glycoproteins that are naturally found in the basal lamina. Laminins are heterotrimers of three non-identical chains: one α, β, and γ chain that associate at the carboxy-termini into a coiled-coil structure to form a heterotrimeric molecule stabilized by disulfide linkages. Each laminin chain is a multidomain protein encoded by a distinct gene. Several isoforms of each chain have been described. Different alpha, beta, and gamma chain isoforms combine to give rise to different heterotrimeric laminin isoforms. Commonly used laminins are alpha 1, beta 1 and gamma 1 (i.e., Laminin-111) and alpha 5, beta 1 and gamma 1 (i.e., Laminin-511). Laminin sequences are available in UniProtKB/Swiss-Prot, including laminin subunit alpha-1 (P25391; LAMA1_HUMAN; SEQ ID NO:59), laminin subunit alpha-5 (O15230; LAMA5_HUMAN; SEQ ID NO:60), laminin subunit beta-1 (P07942; LAMB1_HUMAN; SEQ ID NO:61), and laminin subunit gamma-1 (P11047; LAMC1_HUMAN; SEQ ID NO:62).

Peptides derived from a laminin sequence can also be used in the second coated layer. Exemplary laminin peptides comprise the sequences LRGDN (SEQ ID NO:5) and IKVAV (SEQ ID NO:6), YFQRYLI (SEQ ID NO:7) (Laminin A), YIGSR (SEQ ID NO:1), CDPGYIGSR (SEQ ID NO:8), and PDSGR (SEQ ID NO:9) (Laminin B1), RNIAEIIKDA (SEQ ID NO:10) (Laminin B2), PPFLMLLKGSTR (SEQ ID NO:45), LAIKNDNLVYVY (SEQ ID NO:46), DVISLYNFKHIY (SEQ ID NO:47), TLFLAHGRLVFM (SEQ ID NO:48), LVFMFNVGHKKL (SEQ ID NO:49), NSFMALYLSKGR (SEQ ID NO:50), and RYVVLPRPVCFEKK (SEQ ID NO:51).

Synthetic peptides based on laminin sequences also include RQVFQVAYIIIKA (SEQ ID NO:11) and RKRLQVQLSIRT (SEQ ID NO:12) from the laminin alpha1 chain (Kikkawa, Y., et al. (2009) *Biomaterials* 30:6888-95; and Nomizu, M., et al. (1995) *J Biol Chem.* 270:20583-90).

In some aspects of the invention, the second coated layer of the article includes a collagen or laminin polypeptide or peptide, or a peptide comprising a RGD motif. Preferred peptides are those containing RGD motifs such as the GRGDSP (SEQ ID NO:13) sequence from fibronectin as well as cell adhesive domains from collagen-I, collagen IV, and laminins I-III.

Fibronectin is a glycoprotein (~440 kDa) that binds to integrins and has roles in cell adhesion, migration, differentiation, and growth. Fibronectin has accession number P02751 (FINC_HUMAN; SEQ ID NO:63) in UniProtKB/Swiss-Prot.

The tripeptide Arg-Gly-Asp (RGD) is found in fibronectin as well as other proteins, and can mediate cell attachment. Certain integrins recognize the RGD motif within their ligands, and binding mediates cell-cell interactions. The RGD peptide and peptides that include the RGD motif can be used in the second coated layer. RGD-containing peptides include those having additional amino acid(s) that flank the core RGD sequence, such as RGDS (SEQ ID NO:14), RGDT (SEQ ID NO:15), GRGD (SEQ ID NO:16), GRGDS (SEQ ID NO:17), GRGDG (SEQ ID NO:18), GRGDSP (SEQ ID NO:13), GRGDSG (SEQ ID NO:19), GRGDNP (SEQ ID NO:20), GRGDSPK (SEQ ID NO:21), GRGDSY (SEQ ID NO:22), YRGDS (SEQ ID NO:23), YRGDG (SEQ ID NO:24), YGRGD (SEQ ID NO:25), CGRGDSY (SEQ ID NO:26), CGRGDSPK (SEQ ID NO:27), YAVTGRGDS (SEQ ID NO:28), RGDSPASSKP (SEQ ID NO:29), GRGDSPASSKG (SEQ ID NO:30), GCGYGRGDSPG (SEQ ID NO:31), GGGPHSRNGGGGGGRGDG (SEQ ID NO:32). In some cases the RGD-containing peptide has one or more lipophilic amino acid residues adjacent to the aspartic acid (D), such as RGDV (SEQ ID NO:33), RGDF (SEQ ID NO:34), GRGDF (SEQ ID NO:35), GRGDY (SEQ ID NO:36), GRGDVY (SEQ ID NO:37), and GRGDYPC (SEQ ID NO:38) (Lin, H. B., et al. (1994) *J. Biomed. Mat. Res.* 28:329-342). Peptides derived from fibronectin and that do not include an RGD motif, can also be used in the second coated layer. Other non-RGD peptides have or include sequences such as NGR, LDV, REDV (SEQ ID NO:39), EILDV (SEQ ID NO:40), or KQAGDV (SEQ ID NO:41), and WQPPRARI (SEQ ID NO:52)

Elastin (also known as tropoelastin) is a component of elastic fibers, and includes a high amount of hydrophobic glycine and proline amino acids. Elastin has accession number P15502 (ELN_HUMAN; SEQ ID NO:64) in UniProtKB/Swiss-Prot. Peptides derived from an elastin sequence can also be used in the second coated layer. Exemplary elastin peptides comprise the sequences VAPG (SEQ ID NO:42), VGVAPG (SEQ ID NO:43), VAVAPG (SEQ ID NO:44).

Osteopontin (OPN, SPP1, BSP-1, or BNSP (bone sialoprotein)) is a highly negatively charged, extracellular matrix protein that is implicated in bone remodeling and thought to anchor osteoclasts to the mineral matrix of bones (Reinholt, F. P., et al. (1990) Proc. Natl. Acad. Sci. U.S.A. 87: 4473-4475). Osteopontin has accession number P10451 (OSTP_HUMAN; SEQ ID NO:65) in UniProtKB/Swiss-Prot. The peptide SVVYGLR (SEQ ID NO:53) is found in osteopontin and has integrin binding function (Yokosaki, Y., et al. (1999) J Biol Chem.; 274:36328-36334).

Another integrin binding peptide, the synthetic peptide CRRETAWAC (SEQ ID NO:54), is specific for alpha 5 beta 1 integrin (Koivunen, E., et al. (1994) J. Cell Biol., 124: 373-380) and can be used in articles and methods of the invention.

The ECM protein or peptide can also be modified with a reactive group which can provide further bonding within the coating. In some cases, the coating can be formed using photogroup-derivatized ECM protein, or a photogroup-derivatized peptide that includes a sequence derived from an ECM protein. The photo-derivation of collagen is used to exemplify the process, which can be used to photoderivatize other ECM proteins and peptides. Collagen, such as type I collagen, can be reacted with an amine reactive photogroup containing compound, such as BBA-EAC-NOS, which has a benzophenone photoactivatible group on one end (benzoyl benzoic acid, BBA), a spacer in the middle (epsilon aminocaproic acid, EAC), and an amine reactive thermochemical coupling group on the other end (N-oxysuccinimide, "NOS"). See U.S. Pat. No. 7,220,276.

In other cases, the ECM protein or peptide is coupled to a synthetic polymeric reagent that includes pendent photoreactive groups, and then this photopolymer-protein/peptide conjugate is used as a coating reagent. The synthetic polymer can be heterobifunctional and include a polymeric backbone with pendent photogroups and pendent thermochemically reactive groups which can react with an ECM protein or peptide to bond it to the polymer backbone (see, for example, U.S. Pat. No. 6,514,734; Clapper et al.). The heterobifunctional polymer can be prepared by the copolymerization of a base monomer, such as acrylamide or N-vinylpyrrolidone, with monomers having pendent photoreactive and/or thermochemically reactive groups. An exemplary thermochemically reactive group is N-oxysuccinimide (NOS) ester, which can react with an amine group on the ECM protein or peptide.

Alternatively, a monomer containing a polymerizable function (such as a vinyl group) and a NOS group is reacted with an ECM protein or peptide, and then this monomer is copolymerized with monomers containing photoreactive groups, and with a base monomer, such as acrylamide or N-vinylpyrrolidone. For example, a peptide monomer can be prepared by reacting a sulfhydryl group of the peptide with the maleimide group of N-[3-(6-maleimidylhexanamido) propyl]methacrylamide (Mal MAm). The peptide monomer is then copolymerized with acrylamide and a photoreactive methacrylamide monomer containing a substituted benzophenone(4-benzoylbenzoic acid, BBA). The photopolymer with pendent peptide molecules can then be used to form the second coated layer, which includes a step of UV irradiating the composition to bond the photogroups, thereby immobilizing the peptide via the polymer backbone.

In some coatings, type I collagen can be coated on the device to provide fibrillar or non-fibrillar collagen coated surfaces. In many aspects, the coating is formed by a method which provides collagen I in non-fibrillar form. For example photo-collagen-I can be prepared in a composition having a low pH (e.g., ~pH 2.0) which is used to coat the surface of the implantable article, forming a coating that is non-fibrillar. Raising the pH of the solution (to, e.g., ~pH 9.0) promotes the self-assembly into fibrils.

A coating composition including an ECM protein or peptide that includes an active portion of an ECM protein can be prepared and applied on the intermediate coated layer to form the second coated layer. In many aspects, the second coated layer is the outermost layer of the coating. Exemplary solvents for the polypeptide or peptide include, but are not limited to, water and other aqueous buffers. Exemplary amounts of the polypeptide or peptide in the coating composition are in the range of about 0.1 mg/mL to about 5 mg/mL, or about 0.25 mg/mL to about 1 mg/mL.

The coating can also be described in terms of the weight ratio of phosphorous-containing groups to the cell attachment molecule (e.g., the ECM protein or peptide). In some aspects, coating comprises a mole to weight ratio of phosphorous-containing groups to the cell attachment molecule in the range of about 0.5 mmol/g to about 100 mmol/g.

Irradiation of components of the second coated layer can be performed using conditions similar to irradiation of components of the intermediate coated layer. In one mode of practice, after the second coating composition is applied, the device is illuminated for 60 seconds using an ultraviolet Dymax™ Cure System at a distance of 20 cm.

In another aspect, the ECM protein or peptide that includes an active portion of an ECM protein, includes a pendent polymerizable group that can be reacted to form a polymerized second coated layer. In some aspects, a collagen macromer is used to form the second coated layer. A collagen macromer suitable for use in forming the present coatings is described in Example 12 of U.S. Pub. No. US-2006/0105012A1. Other macromers, such as laminin macromers, can be prepared using an analogous process.

Formation of the second coated layer including a macromer can be initiated by a polymerization initiator comprising a photogroup. Other agents that facilitate formation of a polymerized layer can be present in the composition. These can include, for example, polymerization accelerants which can improve the efficiency of polymerization. Examples of useful accelerants include N-vinyl compounds, particularly N-vinyl pyrrolidone and N-vinyl caprolactam. Such accelerants can be used, for instance, at a concentration of between about 0.01% and about 5%, and preferably between about 0.05% and about 0.5%, by weight, based on the volume of the coating composition.

As another option, after the second coated layer is formed, a temporary barrier or protective layer can be formed over the second coated layer. The barrier or protective layer can be formed from a degradable material that temporarily protects the second coated layer that includes the ECM protein or peptide that includes an active portion of an ECM protein. For example, the barrier layer can shield the coated article during the insertion process, but then degrades after the coated article is inserted into the body.

The coating can be prepared to have a desired thickness. In some aspects, the second coated layer has a thickness in the range of about 10 nm to about 100 nm. In some aspects, the coating has an overall thickness in the range of about 20 nm to about 1 µm.

Cell attachment and proliferation can be measured in various ways. In vitro, cell attachment to a coated surface can be assessed using fluorometric methods. The indicator dye resazurin can be added to a cell culture vessel which is reduced by viable cells present into the highly fluorescent dye resorufin ($579_{Ex}/584_{Em}$). Resazurin kits are commercially available, from, for example, Promega (CellTiter-Blue™). In vitro, cell proliferation can also be assessed using fluorometric methods. The water soluble dye MTT(3-(4,5-dimethylthiazol-2-yl)-2,5-diphenyltetrazolium bromide can be added to the cell culture vessel which is converted to insoluble formazan. The formazan is then solubilized and the concentration determined by optical density at 570 nm. MTT kits are commercially available, from, for example, Molecular Probes (Vybrant™).

In vivo, one way of observing cell attachment and proliferation for coated implantable articles is to histologically compare the surface of an article having a coating of the present invention with that of an article having an uncoated surface or having a chemically different coating. The histological comparison can be carried out after a time of implantation in a mammal. For example, in a test animal such as a rabbit histological examination can be carried out after a period of about 7 and/or a period of about 14 days. In a human subject, this period of time would correlate to about at least about two weeks, on average about four weeks, and in the range of about two weeks to about eight weeks.

Explanted samples can be examined using reagents that allow for the detection of cells associated with the surface of the coated article. In some methods of assessment, observation of endothelial cells is performed by treating the explanted article with BBI (bisbenzimide; Hoechst 33258). Observation of endothelial cells can also be performed by treating the explanted articles with Evans blue dye (Imai, H., et al. (1982) *Arch Pathol Lab Med.* 106:186-91).

The presence of endothelial cells can also be determined using antibodies to CD31, BS1 lectin, and factor VIII (Krasinski, K., et al. (2001) *Circulation* 104:1754). Antibodies against these proteins or lectins are commercially available, from, for example Calbiochem (San Diego, Calif.). In many cases, endothelial cells can be morphologically distinguished from other cell types such as certain immune cells. Smooth muscle cells can be distinguished from other cell types such as endothelial cells and fibroblasts using antibodies against actin (see, for example, Chamley, J. H., et al. (1977) *Cell Tissue Res.* 177:445-57).

Scanning electron microscopy can also be carried out to provide higher magnification of the surfaces of explanted article.

The surfaces of explanted articles can be scored according to endothelial cell coverage. The density of endothelial cells per unit area of the article can be performed. In some cases a scoring system can be employed to assess the level of endothelialization. For example, at a first level the article surface has essentially no cells; at a second level the article surface has some interspersed cells; at a third level the article surface has localized cell density in certain areas; at a fourth level the article surface has a consistent cell density covering most of the article; and at a fifth level the cell density is the highest and cell coverage masks the article.

The invention will be further described with reference to the following non-limiting Examples.

Example 1

Synthesis of Photocollagen (COL1)

Bovine skin collagen (Semed S Powder) was purchased form Kensey Nash Corporation (Exton, Pa.). This collagen has the proportions of type I collagen (95%) and type III collagen (5%) that are usual for skin-derived collagens. Type 1 collagen was photoderivatized by the addition of (benzoylbenzoic acid)-(epsilon aminocaproic acid)-(N-oxysuccinimide)(BBA-EAC-NOS). BBA-EAC-NOS has a benzophenone photoactivatible group on one end (benzoyl benzoic acid, BBA), a spacer in the middle (epsilon aminocaproic acid, EAC), and an amine reactive thermochemical coupling group on the other end (N-oxysuccinimide, "NOS"). BBA-EAC was synthesized from 4-benzoylbenzoyl chloride and 6-aminocaproic acid. Then the NOS ester of BBA-EAC was synthesized by esterifying the carboxy group of BBA-EAC by carbodiimide activation with N-hydroxysuccimide to yield BBA-EAC-NOS. See U.S. Pat. No. 5,744,515 (columns 13 and 14), and U.S. Pat. No. 7,220,276. Atelocollagen (Biom'Up, Saint-Priest FRANCE) was photoderivitized in a similar manner.

Example 2

Synthesis of Phosphorous-Containing Crosslinker 1

Low molecular weight compounds that include photoreactive groups and phosphorous-containing groups were used to form the coatings of the invention. Such compounds include bis(4-benzoylphenyl)hydrogen phosphate, and alkaline salts thereof and tris(4-benzyolphenyl) phosphate. These phosphorous-containing crosslinkers can be synthesized according to US Patent Publication No. 2012/00463384 (Kurdyumov, at al.).

Example 3

Synthesis of Photopolymer Peptides

Photopolymer peptides are prepared as described in U.S. Pat. No. 6,514,734 (Clapper et al.)

Example 4

Endothelial Cell Attachment with Phosphorous-Containing Photocrosslinker Coatings Photocollagen and phosphorous-containing photocrosslinker sodium bis(4-benzoylphenyl phosphate) were prepared as described in Examples 1 and 2, respectively. Photopolymer peptides were prepared as described in Example 3. 96 well polypropylene plates were coated with a photopolyacrylamide to passivate surfaces. A photopolyacrylamide polymer was used which contained 96.5% acrylamide and 3.5% APMA-BBA. Photopolyacrylamide was dissolved in water at 5 mg/mL and 200 µL was added to wells in 96 well plates. Plates were then exposed to UV light for 2 minutes and rinsed 3 times in water. Photocrosslinker coatings followed by photocollagen or photopolymer peptide coatings were then applied to passivated plates as follows. Phosphorous-containing photocrosslinker was dissolved at 5 mg/mL in sterile water and 100 µL was added to wells. Plates were then exposed to UV light for 2 minutes and rinsed 3 times in water. Collagen was dissolved at 0.2 mg/mL in 12 mM hydrochloric acid (HCl) and 100 µL was added to wells. Photopolymer with RGD peptide was prepared at 6 serial dilutions in water ranging from 10 µg/ml down to 0.3 µg/ml and 100 µL was added to wells. Plates with collagen or RGD solutions were exposed to UV light for 1 minute and then rinsed 3 times in phosphate buffered saline PBS containing 1% Tween-20 followed by rinsing 3 times in PBS alone prior to running cell attachment assays.

Cell attachment assays were run using human coronary endothelial cells (HCAECs, Lonza, Walkersville, Md.) cultured in microvascular endothelial growth medium (EGM-2MV, Lonza). A standard curve was prepared using a known number of cells cultured on tissue culture polystyrene (TCPS) plates. Cells were seeded into coated plates at 20,000 cells per well and then incubated for 2 hours. After 2 hours unattached cells were rinsed from the plate and then the number of attached cells was determined using a Cell Titer Blue® Cell Viability Assay (Promega, Madison, Wis.) with comparison to the standard curve. Cells were then cultured an additional 2 days and the number of attached cells was again determined.

Cell attachment results are shown in FIGS. 1 and 2 for 2 hour and 2 day attachment respectively. Results with and without phosphorous containing crosslinker are shown for photocollagen (COL1) coatings at 0.2 mg/ml and photopolymer peptide (RGD) coatings at 10 µg/ml down to 0.3 µg/ml. Results are shown as mean+/−SEM for n of 6 wells. The phosphorous-containing crosslinker (Crosslinker 1) did not promote cell attachment on its own. However, when the phosphorous-containing photocrosslinker was used prior to coating with photocollagen, enhanced attachment was observed compared to no photocrosslinker coatings both at 2 hours and 2 days. This illustrates the distinct and unexpected benefits of applying the phosphorous-containing containing coating layer prior to deposition of photocollagen which results in enhanced cell attachment. When crosslinker 1 was used prior to coating with the RGD polymer peptide increased cell attachment at 2 hours was seen as compared to the polymer peptide alone. At 2 days the number of cells on RGD polymer peptide coatings was the same with and without crosslinker 1.

What is claimed is:

1. An article comprising a biocompatible cell attachment coating comprising:
   (a) an intermediate coated layer comprising a first component that is a compound of one of Formulas I, II, or III

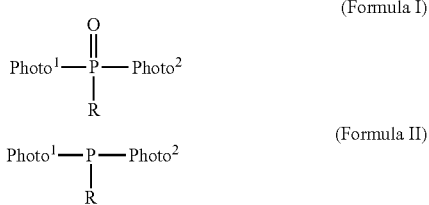
(Formula I)

(Formula II)

wherein, in Formula I and II, Photo¹ and Photo² are, independently, photoreactive groups comprising an aryl ketone group, and at least one covalent linkage between Photo¹ and P, Photo² and P, or both, is interrupted by at least one heteroatom, and R is alkyl, aryl, a photoreactive group, hydroxyl or salt thereof;

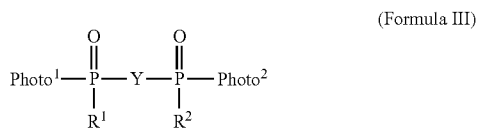
(Formula III)

wherein, in Formula III, Photo¹ and Photo² are, independently, photoreactive groups comprising an aryl ketone functional group, and at least one covalent linkage between Photo¹ and P, Photo² and P, or both, is interrupted by at least one heteroatom; Y represents a covalent bond, N, O, linear or branched $C_1$-$C_{10}$ alkyl; and $R^1$ and $R^2$ are independently is alkyl, aryl, a photoreactive group, hydroxyl or salt thereof;

wherein the first component is immobilized in the coating via the photoreactive group; and (b) a second coated layer comprising a cell attachment molecule comprising an extracellular matrix (ECM) protein, or a peptide that includes an active portion of an ECM protein that is immobilized in the coating;

wherein the intermediate coated layer is positioned between the second coated layer and a surface of the article.

2. The article of claim 1 wherein the extracellular matrix protein is selected from the group consisting of fibronectin, laminin, collagen, procollagen, elastin, vitronectin, tenascin, entactin, fibrinogen, thrombospondin, osteopontin (bone sialoprotein), osteocalcin, von Willebrand Factor, or the peptide includes an active portion of the recited ECM proteins for cell attachment.

3. The article of claim 2 comprising collagen or laminin, or a peptide comprising a RGD motif.

4. The article of claim 3 wherein the peptide comprising a RGD motif is selected from the group consisting of RGD, RGDS (SEQ ID NO:14), RGDT (SEQ ID NO:15), GRGD (SEQ ID NO:16), GRGDS (SEQ ID NO:17), GRGDG (SEQ ID NO:18), GRGDSP (SEQ ID NO:13), GRGDSG (SEQ ID NO:19), GRGDNP (SEQ ID NO:20), GRGDSPK (SEQ ID NO:21), GRGDSY (SEQ ID NO:22), YRGDS (SEQ ID NO:23), YRGDG (SEQ ID NO:24), YGRGD (SEQ ID NO:25), CGRGDSY (SEQ ID NO:26), CGRGDSPK (SEQ ID NO:27), YAVTGRGDS (SEQ ID NO:28), RGDSPASSKP (SEQ ID NO:29), GRGDSPASSKG (SEQ ID NO:30), GCGYGRGDSPG (SEQ ID NO:31), GGGPHSRNGGGGGGRGDG (SEQ ID NO:32), RGDV (SEQ ID NO:33), RGDF (SEQ ID NO:34), GRGDF (SEQ ID NO:35), GRGDY (SEQ ID NO:36), GRGDVY (SEQ ID NO:37), and GRGDYPC (SEQ ID NO:38).

5. The article of claim 2 comprising type I collagen.

6. The article of claim 1 wherein the first component comprises a compound of Formula I.

7. The article of claim 1 wherein the first component is selected from the group consisting of:

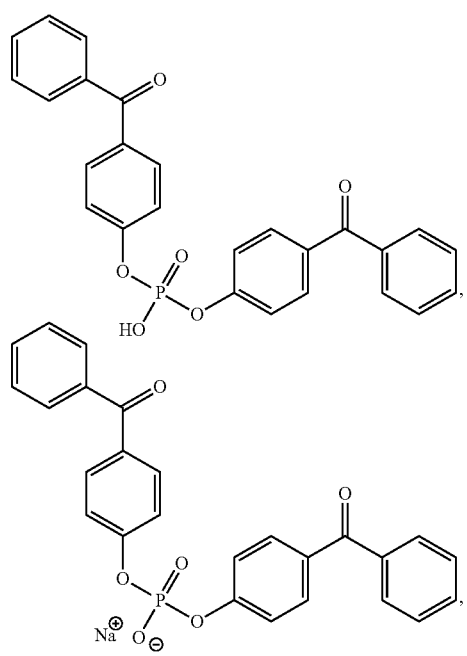

-continued

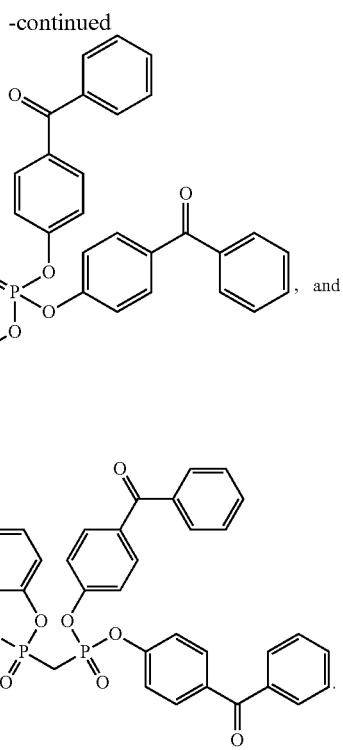, and

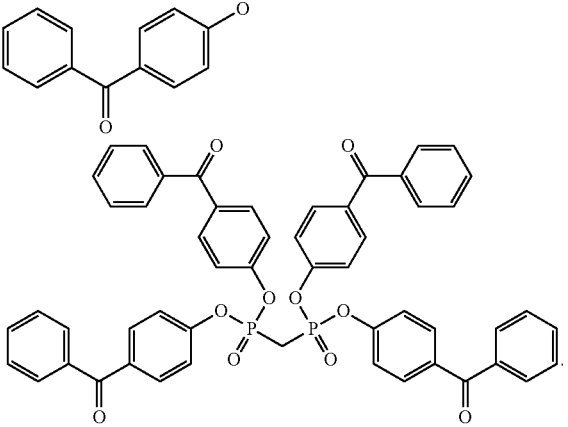

8. The article of claim 7 wherein the first component is:

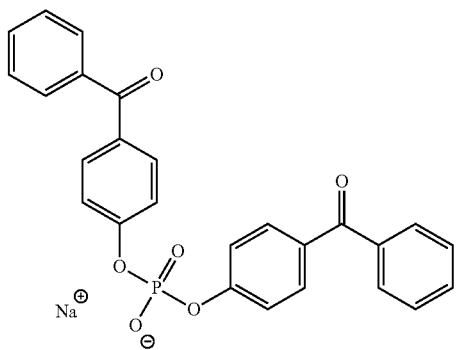

9. The article of claim 1, wherein the article is a medical article and the photoreactive group is bonded to the surface of the medical article, to another first component in the coated layer, or both.

10. The article of claim 1, wherein the intermediate coated layer has a thickness in the range of 10 nm to 100 nm.

11. The article of claim 1, wherein the cell attachment molecule is covalently bonded to a target moiety selected from the first component, another matrix polypeptide, or both the first component and another matrix polypeptide.

12. The article of claim 1, wherein the cell attachment molecule comprises a pendent reacted aryl ketone group allowing the cell attachment molecule to be immobilized in the coating.

13. The article of claim 1, where the second layer further comprises a synthetic polymer, wherein the cell attachment molecule is bonded to the synthetic polymer, the synthetic polymer further comprising a pendent reacted aryl ketone group allowing the cell attachment molecule to be immobilized in the coating.

14. The article of claim 1, wherein the coating comprises a mole to weight ratio of phosphorous-containing groups to the cell attachment molecule in the range of about 0.5 mmol/g to about 100 mmol/g.

15. The article of claim 1, which is a medical article that is insertable or implantable into a portion of the body.

16. The article of claim 1, wherein the article is a cell culture article.

17. A method for forming a coated article comprising steps of:
(a) applying a first composition on an article surface, the first composition comprising first component that is a compound of one of Formulas I, II, or III

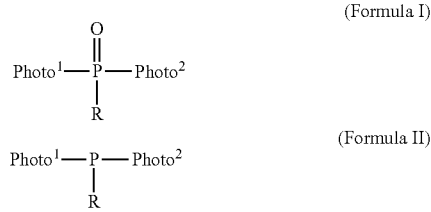

wherein, in Formula I and II, Photo$^1$ and Photo$^2$ are, independently, photoreactive groups comprising an aryl ketone group, and at least one covalent linkage between Photo$^1$ and P, Photo$^2$ and P, or both, is interrupted by at least one heteroatom, and R is alkyl, aryl, a photoreactive group, hydroxyl or salt thereof;

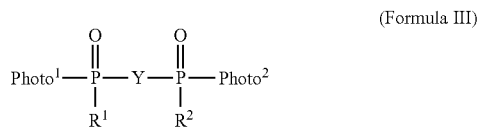

wherein, in-Formula III, Photo$^1$ and Photo$^2$ are, independently, photoreactive groups comprising an aryl ketone group, and at least one covalent linkage between Photo$^1$ and P, Photo$^2$ and P, or both, is interrupted by at least one heteroatom; Y represents a covalent bond, N, O, linear or branched $C_1$-$C_{10}$ alkyl; and R$^1$ and R$^2$ are independently is alkyl, aryl, a photoreactive group, hydroxyl or salt thereof;
(b) providing a second composition on the article surface, the second composition comprising a cell attachment molecule comprising an ECM protein, or a peptide that includes an active portion of an ECM protein for cell attachment;
(c) irradiating the device surface to cause bonding of the aryl functional group to a target moiety, wherein irradiating is performed after step (a), after step (b), or both after steps (a) and (b).

18. A method for promoting attachment and proliferation of cells to an article surface, the method comprising steps of
(a) providing an article of claim 1; and
(b) placing the article in an environment comprising cells, wherein the cells become attached to the coating.

19. The method of claim 18 where the article is an implantable or insertable medical article and the step of placing comprises implanting or inserting the article in the body.

20. The method of claim 18 where the article in a cell culture article and the step of placing comprises placing cells in the article in vitro.

* * * * *

SEQUENCE LISTING

<160> NUMBER OF SEQ ID NOS: 65

<210> SEQ ID NO 1
<211> LENGTH: 5
<212> TYPE: PRT
<213> ORGANISM: Artificial Sequence
<220> FEATURE:
<223> OTHER INFORMATION: chemically synthesized peptide

<400> SEQUENCE: 1

Tyr Ile Gly Ser Arg
1               5

<210> SEQ ID NO 2
<211> LENGTH: 4
<212> TYPE: PRT
<213> ORGANISM: Artificial Sequence
<220> FEATURE:
<223> OTHER INFORMATION: chemically synthesized peptide

<400> SEQUENCE: 2

Asp Gly Glu Ala
1

<210> SEQ ID NO 3
<211> LENGTH: 5
<212> TYPE: PRT
<213> ORGANISM: Artificial Sequence
<220> FEATURE:
<223> OTHER INFORMATION: chemically synthesized peptide

<400> SEQUENCE: 3

Lys Asp Gly Glu Ala
1               5

<210> SEQ ID NO 4
<211> LENGTH: 6
<212> TYPE: PRT
<213> ORGANISM: Artificial Sequence
<220> FEATURE:
<223> OTHER INFORMATION: chemically synthesized peptide
<220> FEATURE:
<221> NAME/KEY: misc_feature
<222> LOCATION: (3)..(3)
<223> OTHER INFORMATION: Xaa = hydroxyproline

<400> SEQUENCE: 4

Gly Phe Xaa Gly Glu Arg
1               5

<210> SEQ ID NO 5
<211> LENGTH: 5
<212> TYPE: PRT
<213> ORGANISM: Artificial Sequence
<220> FEATURE:
<223> OTHER INFORMATION: chemically synthesized peptide

<400> SEQUENCE: 5

Leu Arg Gly Asp Asn
1               5

<210> SEQ ID NO 6
<211> LENGTH: 5
<212> TYPE: PRT
<213> ORGANISM: Artificial Sequence
<220> FEATURE:
<223> OTHER INFORMATION: chemically synthesized peptide

```
<400> SEQUENCE: 6

Ile Lys Val Ala Val
1               5

<210> SEQ ID NO 7
<211> LENGTH: 7
<212> TYPE: PRT
<213> ORGANISM: Artificial Sequence
<220> FEATURE:
<223> OTHER INFORMATION: chemically synthesized peptide

<400> SEQUENCE: 7

Tyr Phe Gln Arg Tyr Leu Ile
1               5

<210> SEQ ID NO 8
<211> LENGTH: 9
<212> TYPE: PRT
<213> ORGANISM: Artificial Sequence
<220> FEATURE:
<223> OTHER INFORMATION: chemically synthesized peptide

<400> SEQUENCE: 8

Cys Asp Pro Gly Tyr Ile Gly Ser Arg
1               5

<210> SEQ ID NO 9
<211> LENGTH: 5
<212> TYPE: PRT
<213> ORGANISM: Artificial Sequence
<220> FEATURE:
<223> OTHER INFORMATION: chemically synthesized peptide

<400> SEQUENCE: 9

Pro Asp Ser Gly Arg
1               5

<210> SEQ ID NO 10
<211> LENGTH: 10
<212> TYPE: PRT
<213> ORGANISM: Artificial Sequence
<220> FEATURE:
<223> OTHER INFORMATION: chemically synthesized peptide

<400> SEQUENCE: 10

Arg Asn Ile Ala Glu Ile Ile Lys Asp Ala
1               5                   10

<210> SEQ ID NO 11
<211> LENGTH: 13
<212> TYPE: PRT
<213> ORGANISM: Artificial Sequence
<220> FEATURE:
<223> OTHER INFORMATION: chemically synthesized peptide

<400> SEQUENCE: 11

Arg Gln Val Phe Gln Val Ala Tyr Ile Ile Ile Lys Ala
1               5                   10

<210> SEQ ID NO 12
<211> LENGTH: 12
<212> TYPE: PRT
<213> ORGANISM: Artificial Sequence
<220> FEATURE:
<223> OTHER INFORMATION: chemically synthesized peptide

<400> SEQUENCE: 12
```

```
Arg Lys Arg Leu Gln Val Gln Leu Ser Ile Arg Thr
1               5                   10
```

<210> SEQ ID NO 13
<211> LENGTH: 6
<212> TYPE: PRT
<213> ORGANISM: Artificial Sequence
<220> FEATURE:
<223> OTHER INFORMATION: chemically synthesized peptide

<400> SEQUENCE: 13

```
Gly Arg Gly Asp Ser Pro
1               5
```

<210> SEQ ID NO 14
<211> LENGTH: 4
<212> TYPE: PRT
<213> ORGANISM: Artificial Sequence
<220> FEATURE:
<223> OTHER INFORMATION: chemically synthesized peptide

<400> SEQUENCE: 14

```
Arg Gly Asp Ser
1
```

<210> SEQ ID NO 15
<211> LENGTH: 4
<212> TYPE: PRT
<213> ORGANISM: Artificial Sequence
<220> FEATURE:
<223> OTHER INFORMATION: chemically synthesized peptide

<400> SEQUENCE: 15

```
Arg Gly Asp Thr
1
```

<210> SEQ ID NO 16
<211> LENGTH: 4
<212> TYPE: PRT
<213> ORGANISM: Artificial Sequence
<220> FEATURE:
<223> OTHER INFORMATION: chemically synthesized peptide

<400> SEQUENCE: 16

```
Gly Arg Gly Asp
1
```

<210> SEQ ID NO 17
<211> LENGTH: 5
<212> TYPE: PRT
<213> ORGANISM: Artificial Sequence
<220> FEATURE:
<223> OTHER INFORMATION: chemically synthesized peptide

<400> SEQUENCE: 17

```
Gly Arg Gly Asp Ser
1               5
```

<210> SEQ ID NO 18
<211> LENGTH: 5
<212> TYPE: PRT
<213> ORGANISM: Artificial Sequence
<220> FEATURE:
<223> OTHER INFORMATION: chemically synthesized peptide

<400> SEQUENCE: 18

```
Gly Arg Gly Asp Gly
1               5

<210> SEQ ID NO 19
<211> LENGTH: 6
<212> TYPE: PRT
<213> ORGANISM: Artificial Sequence
<220> FEATURE:
<223> OTHER INFORMATION: chemically synthesized peptide

<400> SEQUENCE: 19

Gly Arg Gly Asp Ser Gly
1               5

<210> SEQ ID NO 20
<211> LENGTH: 6
<212> TYPE: PRT
<213> ORGANISM: Artificial Sequence
<220> FEATURE:
<223> OTHER INFORMATION: chemically synthesized peptide

<400> SEQUENCE: 20

Gly Arg Gly Asp Asn Pro
1               5

<210> SEQ ID NO 21
<211> LENGTH: 7
<212> TYPE: PRT
<213> ORGANISM: Artificial Sequence
<220> FEATURE:
<223> OTHER INFORMATION: chemically synthesized peptide

<400> SEQUENCE: 21

Gly Arg Gly Asp Ser Pro Lys
1               5

<210> SEQ ID NO 22
<211> LENGTH: 6
<212> TYPE: PRT
<213> ORGANISM: Artificial Sequence
<220> FEATURE:
<223> OTHER INFORMATION: chemically synthesized peptide

<400> SEQUENCE: 22

Gly Arg Gly Asp Ser Tyr
1               5

<210> SEQ ID NO 23
<211> LENGTH: 5
<212> TYPE: PRT
<213> ORGANISM: Artificial Sequence
<220> FEATURE:
<223> OTHER INFORMATION: chemically synthesized peptide

<400> SEQUENCE: 23

Tyr Arg Gly Asp Ser
1               5

<210> SEQ ID NO 24
<211> LENGTH: 5
<212> TYPE: PRT
<213> ORGANISM: Artificial Sequence
<220> FEATURE:
<223> OTHER INFORMATION: chemically synthesized peptide

<400> SEQUENCE: 24

Tyr Arg Gly Asp Gly
```

```
1               5

<210> SEQ ID NO 25
<211> LENGTH: 5
<212> TYPE: PRT
<213> ORGANISM: Artificial Sequence
<220> FEATURE:
<223> OTHER INFORMATION: chemically synthesized peptide

<400> SEQUENCE: 25

Tyr Gly Arg Gly Asp
1               5

<210> SEQ ID NO 26
<211> LENGTH: 7
<212> TYPE: PRT
<213> ORGANISM: Artificial Sequence
<220> FEATURE:
<223> OTHER INFORMATION: chemically synthesized peptide

<400> SEQUENCE: 26

Cys Gly Arg Gly Asp Ser Tyr
1               5

<210> SEQ ID NO 27
<211> LENGTH: 8
<212> TYPE: PRT
<213> ORGANISM: Artificial Sequence
<220> FEATURE:
<223> OTHER INFORMATION: chemically synthesized peptide

<400> SEQUENCE: 27

Cys Gly Arg Gly Asp Ser Pro Lys
1               5

<210> SEQ ID NO 28
<211> LENGTH: 9
<212> TYPE: PRT
<213> ORGANISM: Artificial Sequence
<220> FEATURE:
<223> OTHER INFORMATION: chemically synthesized peptide

<400> SEQUENCE: 28

Tyr Ala Val Thr Gly Arg Gly Asp Ser
1               5

<210> SEQ ID NO 29
<211> LENGTH: 10
<212> TYPE: PRT
<213> ORGANISM: Artificial Sequence
<220> FEATURE:
<223> OTHER INFORMATION: chemically synthesized peptide

<400> SEQUENCE: 29

Arg Gly Asp Ser Pro Ala Ser Ser Lys Pro
1               5                   10

<210> SEQ ID NO 30
<211> LENGTH: 11
<212> TYPE: PRT
<213> ORGANISM: Artificial Sequence
```

```
<220> FEATURE:
<223> OTHER INFORMATION: chemically synthesized peptide

<400> SEQUENCE: 30

Gly Arg Gly Asp Ser Pro Ala Ser Ser Lys Gly
1               5                   10

<210> SEQ ID NO 31
<211> LENGTH: 11
<212> TYPE: PRT
<213> ORGANISM: Artificial Sequence
<220> FEATURE:
<223> OTHER INFORMATION: chemically synthesized peptide

<400> SEQUENCE: 31

Gly Cys Gly Tyr Gly Arg Gly Asp Ser Pro Gly
1               5                   10

<210> SEQ ID NO 32
<211> LENGTH: 18
<212> TYPE: PRT
<213> ORGANISM: Artificial Sequence
<220> FEATURE:
<223> OTHER INFORMATION: chemically synthesized peptide

<400> SEQUENCE: 32

Gly Gly Gly Pro His Ser Arg Asn Gly Gly Gly Gly Gly Arg Gly
1               5                   10                  15

Asp Gly

<210> SEQ ID NO 33
<211> LENGTH: 4
<212> TYPE: PRT
<213> ORGANISM: Artificial Sequence
<220> FEATURE:
<223> OTHER INFORMATION: chemically synthesized peptide

<400> SEQUENCE: 33

Arg Gly Asp Val
1

<210> SEQ ID NO 34
<211> LENGTH: 4
<212> TYPE: PRT
<213> ORGANISM: Artificial Sequence
<220> FEATURE:
<223> OTHER INFORMATION: chemically synthesized peptide

<400> SEQUENCE: 34

Arg Gly Asp Phe
1

<210> SEQ ID NO 35
<211> LENGTH: 5
<212> TYPE: PRT
<213> ORGANISM: Artificial Sequence
<220> FEATURE:
<223> OTHER INFORMATION: chemically synthesized peptide

<400> SEQUENCE: 35

Gly Arg Gly Asp Phe
1               5

<210> SEQ ID NO 36
<211> LENGTH: 5
<212> TYPE: PRT
```

```
<213> ORGANISM: Artificial Sequence
<220> FEATURE:
<223> OTHER INFORMATION: chemically synthesized peptide

<400> SEQUENCE: 36

Gly Arg Gly Asp Tyr
1               5

<210> SEQ ID NO 37
<211> LENGTH: 6
<212> TYPE: PRT
<213> ORGANISM: Artificial Sequence
<220> FEATURE:
<223> OTHER INFORMATION: chemically synthesized peptide

<400> SEQUENCE: 37

Gly Arg Gly Asp Val Tyr
1               5

<210> SEQ ID NO 38
<211> LENGTH: 7
<212> TYPE: PRT
<213> ORGANISM: Artificial Sequence
<220> FEATURE:
<223> OTHER INFORMATION: chemically synthesized peptide

<400> SEQUENCE: 38

Gly Arg Gly Asp Tyr Pro Cys
1               5

<210> SEQ ID NO 39
<211> LENGTH: 4
<212> TYPE: PRT
<213> ORGANISM: Artificial Sequence
<220> FEATURE:
<223> OTHER INFORMATION: chemically synthesized peptide

<400> SEQUENCE: 39

Arg Glu Asp Val
1

<210> SEQ ID NO 40
<211> LENGTH: 5
<212> TYPE: PRT
<213> ORGANISM: Artificial Sequence
<220> FEATURE:
<223> OTHER INFORMATION: chemically synthesized peptide

<400> SEQUENCE: 40

Glu Ile Leu Asp Val
1               5

<210> SEQ ID NO 41
<211> LENGTH: 6
<212> TYPE: PRT
<213> ORGANISM: Artificial Sequence
<220> FEATURE:
<223> OTHER INFORMATION: chemically synthesized peptide

<400> SEQUENCE: 41

Lys Gln Ala Gly Asp Val
1               5

<210> SEQ ID NO 42
<211> LENGTH: 4
<212> TYPE: PRT
<213> ORGANISM: Artificial Sequence
```

```
<220> FEATURE:
<223> OTHER INFORMATION: chemically synthesized peptide

<400> SEQUENCE: 42

Val Ala Pro Gly
1

<210> SEQ ID NO 43
<211> LENGTH: 6
<212> TYPE: PRT
<213> ORGANISM: Artificial Sequence
<220> FEATURE:
<223> OTHER INFORMATION: chemically synthesized peptide

<400> SEQUENCE: 43

Val Gly Val Ala Pro Gly
1               5

<210> SEQ ID NO 44
<211> LENGTH: 6
<212> TYPE: PRT
<213> ORGANISM: Artificial Sequence
<220> FEATURE:
<223> OTHER INFORMATION: chemically synthesized peptide

<400> SEQUENCE: 44

Val Ala Val Ala Pro Gly
1               5

<210> SEQ ID NO 45
<211> LENGTH: 12
<212> TYPE: PRT
<213> ORGANISM: Artificial Sequence
<220> FEATURE:
<223> OTHER INFORMATION: chemically synthesized peptide

<400> SEQUENCE: 45

Pro Pro Phe Leu Met Leu Leu Lys Gly Ser Thr Arg
1               5                   10

<210> SEQ ID NO 46
<211> LENGTH: 12
<212> TYPE: PRT
<213> ORGANISM: Artificial Sequence
<220> FEATURE:
<223> OTHER INFORMATION: chemically synthesized peptide

<400> SEQUENCE: 46

Leu Ala Ile Lys Asn Asp Asn Leu Val Tyr Val Tyr
1               5                   10

<210> SEQ ID NO 47
<211> LENGTH: 12
<212> TYPE: PRT
<213> ORGANISM: Artificial Sequence
<220> FEATURE:
<223> OTHER INFORMATION: chemically synthesized peptide

<400> SEQUENCE: 47

Asp Val Ile Ser Leu Tyr Asn Phe Lys His Ile Tyr
1               5                   10

<210> SEQ ID NO 48
<211> LENGTH: 12
<212> TYPE: PRT
<213> ORGANISM: Artificial Sequence
<220> FEATURE:
```

<223> OTHER INFORMATION: chemically synthesized peptide

<400> SEQUENCE: 48

Thr Leu Phe Leu Ala His Gly Arg Leu Val Phe Met
1               5                   10

<210> SEQ ID NO 49
<211> LENGTH: 12
<212> TYPE: PRT
<213> ORGANISM: Artificial Sequence
<220> FEATURE:
<223> OTHER INFORMATION: chemically synthesized peptide

<400> SEQUENCE: 49

Leu Val Phe Met Phe Asn Val Gly His Lys Lys Leu
1               5                   10

<210> SEQ ID NO 50
<211> LENGTH: 12
<212> TYPE: PRT
<213> ORGANISM: Artificial Sequence
<220> FEATURE:
<223> OTHER INFORMATION: chemically synthesized peptide

<400> SEQUENCE: 50

Asn Ser Phe Met Ala Leu Tyr Leu Ser Lys Gly Arg
1               5                   10

<210> SEQ ID NO 51
<211> LENGTH: 14
<212> TYPE: PRT
<213> ORGANISM: Artificial Sequence
<220> FEATURE:
<223> OTHER INFORMATION: chemically synthesized peptide

<400> SEQUENCE: 51

Arg Tyr Val Val Leu Pro Arg Pro Val Cys Phe Glu Lys Lys
1               5                   10

<210> SEQ ID NO 52
<211> LENGTH: 8
<212> TYPE: PRT
<213> ORGANISM: Artificial Sequence
<220> FEATURE:
<223> OTHER INFORMATION: chemically synthesized peptide

<400> SEQUENCE: 52

Trp Gln Pro Pro Arg Ala Arg Ile
1               5

<210> SEQ ID NO 53
<211> LENGTH: 7
<212> TYPE: PRT
<213> ORGANISM: Artificial Sequence
<220> FEATURE:
<223> OTHER INFORMATION: chemically synthesized peptide

<400> SEQUENCE: 53

Ser Val Val Tyr Gly Leu Arg
1               5

<210> SEQ ID NO 54
<211> LENGTH: 9
<212> TYPE: PRT
<213> ORGANISM: Artificial Sequence
<220> FEATURE:
<223> OTHER INFORMATION: chemically synthesized peptide

<400> SEQUENCE: 54

Cys Arg Arg Glu Thr Ala Trp Ala Cys
1               5

<210> SEQ ID NO 55
<211> LENGTH: 1464
<212> TYPE: PRT
<213> ORGANISM: Homo sapiens

<400> SEQUENCE: 55

Met Phe Ser Phe Val Asp Leu Arg Leu Leu Leu Leu Leu Ala Ala Thr
1               5                   10                  15

Ala Leu Leu Thr His Gly Gln Glu Glu Gly Gln Val Glu Gly Gln Asp
            20                  25                  30

Glu Asp Ile Pro Pro Ile Thr Cys Val Gln Asn Gly Leu Arg Tyr His
        35                  40                  45

Asp Arg Asp Val Trp Lys Pro Glu Pro Cys Arg Ile Cys Val Cys Asp
    50                  55                  60

Asn Gly Lys Val Leu Cys Asp Asp Val Ile Cys Asp Glu Thr Lys Asn
65                  70                  75                  80

Cys Pro Gly Ala Glu Val Pro Glu Gly Glu Cys Cys Pro Val Cys Pro
                85                  90                  95

Asp Gly Ser Glu Ser Pro Thr Asp Gln Glu Thr Thr Gly Val Glu Gly
            100                 105                 110

Pro Lys Gly Asp Thr Gly Pro Arg Gly Pro Arg Gly Pro Ala Gly Pro
        115                 120                 125

Pro Gly Arg Asp Gly Ile Pro Gly Gln Pro Gly Leu Pro Gly Pro Pro
    130                 135                 140

Gly Pro Pro Gly Pro Pro Gly Pro Pro Gly Leu Gly Gly Asn Phe Ala
145                 150                 155                 160

Pro Gln Leu Ser Tyr Gly Tyr Asp Glu Lys Ser Thr Gly Gly Ile Ser
                165                 170                 175

Val Pro Gly Pro Met Gly Pro Ser Gly Pro Arg Gly Leu Pro Gly Pro
            180                 185                 190

Pro Gly Ala Pro Gly Pro Gln Gly Phe Gln Gly Pro Pro Gly Glu Pro
        195                 200                 205

Gly Glu Pro Gly Ala Ser Gly Pro Met Gly Pro Arg Gly Pro Pro Gly
    210                 215                 220

Pro Pro Gly Lys Asn Gly Asp Asp Gly Glu Ala Gly Lys Pro Gly Arg
225                 230                 235                 240

Pro Gly Glu Arg Gly Pro Pro Gly Pro Gln Gly Ala Arg Gly Leu Pro
                245                 250                 255

Gly Thr Ala Gly Leu Pro Gly Met Lys Gly His Arg Gly Phe Ser Gly
            260                 265                 270

Leu Asp Gly Ala Lys Gly Asp Ala Gly Pro Ala Gly Pro Lys Gly Glu
        275                 280                 285

Pro Gly Ser Pro Gly Glu Asn Gly Ala Pro Gly Gln Met Gly Pro Arg
    290                 295                 300

Gly Leu Pro Gly Glu Arg Gly Arg Pro Gly Ala Pro Gly Pro Ala Gly
305                 310                 315                 320

Ala Arg Gly Asn Asp Gly Ala Thr Gly Ala Ala Gly Pro Pro Gly Pro
                325                 330                 335

Thr Gly Pro Ala Gly Pro Pro Gly Phe Pro Gly Ala Val Gly Ala Lys
            340                 345                 350

```
Gly Glu Ala Gly Pro Gln Gly Pro Arg Gly Ser Gly Pro Gln Gly
            355                 360                 365
Val Arg Gly Glu Pro Gly Pro Pro Gly Pro Ala Gly Ala Ala Gly Pro
    370                 375                 380
Ala Gly Asn Pro Gly Ala Asp Gly Gln Pro Gly Ala Lys Gly Ala Asn
385                 390                 395                 400
Gly Ala Pro Gly Ile Ala Gly Ala Pro Gly Phe Pro Gly Ala Arg Gly
                405                 410                 415
Pro Ser Gly Pro Gln Gly Pro Gly Gly Pro Pro Gly Pro Lys Gly Asn
                420                 425                 430
Ser Gly Glu Pro Gly Ala Pro Gly Ser Lys Gly Asp Thr Gly Ala Lys
            435                 440                 445
Gly Glu Pro Gly Pro Val Gly Val Gln Gly Pro Pro Gly Pro Ala Gly
            450                 455                 460
Glu Glu Gly Lys Arg Gly Ala Arg Gly Glu Pro Gly Pro Thr Gly Leu
465                 470                 475                 480
Pro Gly Pro Pro Gly Glu Arg Gly Gly Pro Gly Ser Arg Gly Phe Pro
                485                 490                 495
Gly Ala Asp Gly Val Ala Gly Pro Lys Gly Pro Ala Gly Glu Arg Gly
                500                 505                 510
Ser Pro Gly Pro Ala Gly Pro Lys Gly Ser Pro Gly Glu Ala Gly Arg
                515                 520                 525
Pro Gly Glu Ala Gly Leu Pro Gly Ala Lys Gly Leu Thr Gly Ser Pro
            530                 535                 540
Gly Ser Pro Gly Pro Asp Gly Lys Thr Gly Pro Pro Gly Pro Ala Gly
545                 550                 555                 560
Gln Asp Gly Arg Pro Gly Pro Pro Gly Pro Pro Gly Ala Arg Gly Gln
                565                 570                 575
Ala Gly Val Met Gly Phe Pro Gly Pro Lys Gly Ala Ala Gly Glu Pro
                580                 585                 590
Gly Lys Ala Gly Glu Arg Gly Val Pro Gly Pro Pro Gly Ala Val Gly
            595                 600                 605
Pro Ala Gly Lys Asp Gly Glu Ala Gly Ala Gln Gly Pro Pro Gly Pro
            610                 615                 620
Ala Gly Pro Ala Gly Glu Arg Gly Glu Gln Gly Pro Ala Gly Ser Pro
625                 630                 635                 640
Gly Phe Gln Gly Leu Pro Gly Pro Ala Gly Pro Pro Gly Glu Ala Gly
                645                 650                 655
Lys Pro Gly Glu Gln Gly Val Pro Gly Asp Leu Gly Ala Pro Gly Pro
                660                 665                 670
Ser Gly Ala Arg Gly Glu Arg Gly Phe Pro Gly Glu Arg Gly Val Gln
                675                 680                 685
Gly Pro Pro Gly Pro Ala Gly Pro Arg Gly Ala Asn Gly Ala Pro Gly
            690                 695                 700
Asn Asp Gly Ala Lys Gly Asp Ala Gly Ala Pro Gly Ala Pro Gly Ser
705                 710                 715                 720
Gln Gly Ala Pro Gly Leu Gln Gly Met Pro Gly Glu Arg Gly Ala Ala
                725                 730                 735
Gly Leu Pro Gly Pro Lys Gly Asp Arg Gly Asp Ala Gly Pro Lys Gly
                740                 745                 750
Ala Asp Gly Ser Pro Gly Lys Asp Gly Val Arg Gly Leu Thr Gly Pro
                755                 760                 765
```

```
Ile Gly Pro Pro Gly Pro Ala Gly Ala Pro Gly Asp Lys Gly Glu Ser
    770             775                 780

Gly Pro Ser Gly Pro Ala Gly Pro Thr Gly Ala Arg Gly Ala Pro Gly
785                 790                 795                 800

Asp Arg Gly Glu Pro Gly Pro Gly Pro Ala Gly Phe Ala Gly Pro
                805             810                 815

Pro Gly Ala Asp Gly Gln Pro Gly Ala Lys Gly Glu Pro Gly Asp Ala
            820             825                 830

Gly Ala Lys Gly Asp Ala Gly Pro Gly Pro Ala Gly Pro Ala Gly
                835             840                 845

Pro Pro Gly Pro Ile Gly Asn Val Gly Ala Pro Gly Ala Lys Gly Ala
    850             855                 860

Arg Gly Ser Ala Gly Pro Pro Gly Ala Thr Gly Phe Pro Gly Ala Ala
865             870                 875                 880

Gly Arg Val Gly Pro Pro Gly Ser Gly Asn Ala Gly Pro Pro Gly
                885             890                 895

Pro Pro Gly Pro Ala Gly Lys Glu Gly Gly Lys Gly Pro Arg Gly Glu
    900             905                 910

Thr Gly Pro Ala Gly Arg Pro Gly Glu Val Gly Pro Pro Gly Pro Pro
                915             920                 925

Gly Pro Ala Gly Glu Lys Gly Ser Pro Gly Ala Asp Gly Pro Ala Gly
    930             935                 940

Ala Pro Gly Thr Pro Gly Pro Gln Gly Ile Ala Gly Gln Arg Gly Val
945             950                 955                 960

Val Gly Leu Pro Gly Gln Arg Gly Glu Arg Gly Phe Pro Gly Leu Pro
                965             970                 975

Gly Pro Ser Gly Glu Pro Gly Lys Gln Gly Pro Ser Gly Ala Ser Gly
            980             985                 990

Glu Arg Gly Pro Pro Gly Pro Met  Gly Pro Pro Gly Leu Ala Gly Pro
            995             1000                 1005

Pro Gly Glu Ser Gly Arg Glu  Gly Ala Pro Gly Ala  Glu Gly Ser
    1010            1015                1020

Pro Gly Arg Asp Gly Ser Pro  Gly Ala Lys Gly Asp  Arg Gly Glu
    1025            1030                1035

Thr Gly Pro Ala Gly Pro Pro  Gly Ala Pro Gly Ala  Pro Gly Ala
    1040            1045                1050

Pro Gly Pro Val Gly Pro Ala  Gly Lys Ser Gly Asp  Arg Gly Glu
    1055            1060                1065

Thr Gly Pro Ala Gly Pro Thr  Gly Pro Val Gly Pro  Val Gly Ala
    1070            1075                1080

Arg Gly Pro Ala Gly Pro Gln  Gly Pro Arg Gly Asp  Lys Gly Glu
    1085            1090                1095

Thr Gly Glu Gln Gly Asp Arg  Gly Ile Lys Gly His  Arg Gly Phe
    1100            1105                1110

Ser Gly Leu Gln Gly Pro Pro  Gly Pro Pro Gly Ser  Pro Gly Glu
    1115            1120                1125

Gln Gly Pro Ser Gly Ala Ser  Gly Pro Ala Gly Pro  Arg Gly Pro
    1130            1135                1140

Pro Gly Ser Ala Gly Ala Pro  Gly Lys Asp Gly Leu  Asn Gly Leu
    1145            1150                1155

Pro Gly Pro Ile Gly Pro Pro  Gly Pro Arg Gly Arg  Thr Gly Asp
    1160            1165                1170

Ala Gly Pro Val Gly Pro Pro  Gly Pro Pro Gly Pro  Pro Gly Pro
```

```
            1175                1180                1185

Pro Gly Pro Pro Ser Ala Gly Phe Asp Phe Ser Phe Leu Pro Gln
        1190                1195                1200

Pro Pro Gln Glu Lys Ala His Asp Gly Gly Arg Tyr Tyr Arg Ala
    1205                1210                1215

Asp Asp Ala Asn Val Val Arg Asp Arg Asp Leu Glu Val Asp Thr
1220                1225                1230

Thr Leu Lys Ser Leu Ser Gln Gln Ile Glu Asn Ile Arg Ser Pro
    1235                1240                1245

Glu Gly Ser Arg Lys Asn Pro Ala Arg Thr Cys Arg Asp Leu Lys
1250                1255                1260

Met Cys His Ser Asp Trp Lys Ser Gly Glu Tyr Trp Ile Asp Pro
    1265                1270                1275

Asn Gln Gly Cys Asn Leu Asp Ala Ile Lys Val Phe Cys Asn Met
1280                1285                1290

Glu Thr Gly Glu Thr Cys Val Tyr Pro Thr Gln Pro Ser Val Ala
    1295                1300                1305

Gln Lys Asn Trp Tyr Ile Ser Lys Asn Pro Lys Asp Lys Arg His
1310                1315                1320

Val Trp Phe Gly Glu Ser Met Thr Asp Gly Phe Gln Phe Glu Tyr
    1325                1330                1335

Gly Gly Gln Gly Ser Asp Pro Ala Asp Val Ala Ile Gln Leu Thr
1340                1345                1350

Phe Leu Arg Leu Met Ser Thr Glu Ala Ser Gln Asn Ile Thr Tyr
    1355                1360                1365

His Cys Lys Asn Ser Val Ala Tyr Met Asp Gln Gln Thr Gly Asn
1370                1375                1380

Leu Lys Lys Ala Leu Leu Leu Gln Gly Ser Asn Glu Ile Glu Ile
    1385                1390                1395

Arg Ala Glu Gly Asn Ser Arg Phe Thr Tyr Ser Val Thr Val Asp
1400                1405                1410

Gly Cys Thr Ser His Thr Gly Ala Trp Gly Lys Thr Val Ile Glu
    1415                1420                1425

Tyr Lys Thr Thr Lys Thr Ser Arg Leu Pro Ile Ile Asp Val Ala
1430                1435                1440

Pro Leu Asp Val Gly Ala Pro Asp Gln Glu Phe Gly Phe Asp Val
    1445                1450                1455

Gly Pro Val Cys Phe Leu
    1460

<210> SEQ ID NO 56
<211> LENGTH: 1464
<212> TYPE: PRT
<213> ORGANISM: Pan troglodytes

<400> SEQUENCE: 56

Met Phe Ser Phe Val Asp Leu Arg Leu Leu Leu Leu Ala Ala Thr
1               5                   10                  15

Ala Leu Leu Thr His Gly Gln Glu Glu Gly Gln Val Glu Gly Gln Asp
                20                  25                  30

Glu Asp Ile Pro Pro Ile Thr Cys Val Gln Asn Gly Leu Arg Tyr His
                35                  40                  45

Asp Arg Asp Val Trp Lys Pro Glu Pro Cys Arg Ile Cys Val Cys Asp
        50                  55                  60
```

```
Asn Gly Lys Val Leu Cys Asp Asp Val Ile Cys Asp Glu Thr Lys Asn
 65                  70                  75                  80

Cys Pro Gly Ala Glu Val Pro Glu Gly Glu Cys Cys Pro Val Cys Pro
                 85                  90                  95

Asp Gly Ser Glu Ser Pro Thr Asp Gln Glu Thr Thr Gly Val Glu Gly
            100                 105                 110

Pro Lys Gly Asp Thr Gly Pro Arg Gly Pro Arg Gly Pro Ala Gly Pro
        115                 120                 125

Pro Gly Arg Asp Gly Ile Pro Gly Gln Pro Gly Leu Pro Gly Pro Pro
    130                 135                 140

Gly Pro Pro Gly Pro Pro Gly Pro Pro Gly Leu Gly Gly Asn Phe Ala
145                 150                 155                 160

Pro Gln Leu Ser Tyr Gly Tyr Asp Glu Lys Ser Thr Gly Gly Ile Ser
                165                 170                 175

Val Pro Gly Pro Met Gly Pro Ser Gly Pro Arg Gly Leu Pro Gly Pro
            180                 185                 190

Pro Gly Ala Pro Gly Pro Gln Gly Phe Gln Gly Pro Pro Gly Glu Pro
            195                 200                 205

Gly Glu Pro Gly Ala Ser Gly Pro Met Gly Pro Arg Gly Pro Pro Gly
210                 215                 220

Pro Pro Gly Lys Asn Gly Asp Asp Gly Glu Ala Gly Lys Pro Gly Arg
225                 230                 235                 240

Pro Gly Glu Arg Gly Pro Pro Gly Pro Gln Gly Ala Arg Gly Leu Pro
                245                 250                 255

Gly Thr Ala Gly Leu Pro Gly Met Lys Gly His Arg Gly Phe Ser Gly
            260                 265                 270

Leu Asp Gly Ala Lys Gly Asp Ala Gly Pro Ala Gly Pro Lys Gly Glu
            275                 280                 285

Pro Gly Ser Pro Gly Glu Asn Gly Ala Pro Gly Gln Met Gly Pro Arg
            290                 295                 300

Gly Leu Pro Gly Glu Arg Gly Arg Pro Gly Ala Pro Gly Pro Ala Gly
305                 310                 315                 320

Ala Arg Gly Asn Asp Gly Ala Thr Gly Ala Ala Gly Pro Pro Gly Pro
                325                 330                 335

Thr Gly Pro Ala Gly Pro Pro Gly Phe Pro Gly Ala Val Gly Ala Lys
            340                 345                 350

Gly Glu Ala Gly Pro Gln Gly Pro Arg Gly Ser Glu Gly Pro Gln Gly
            355                 360                 365

Val Arg Gly Glu Pro Gly Pro Pro Gly Pro Ala Gly Ala Ala Gly Pro
    370                 375                 380

Ala Gly Asn Pro Gly Ala Asp Gly Gln Pro Gly Ala Lys Gly Ala Asn
385                 390                 395                 400

Gly Ala Pro Gly Ile Ala Gly Ala Pro Gly Phe Pro Gly Ala Arg Gly
                405                 410                 415

Pro Ser Gly Pro Gln Gly Pro Gly Pro Pro Gly Pro Lys Gly Asn
            420                 425                 430

Ser Gly Glu Pro Gly Ala Pro Gly Ser Lys Gly Asp Thr Gly Ala Lys
        435                 440                 445

Gly Glu Pro Gly Pro Val Gly Val Gln Gly Pro Pro Gly Pro Ala Gly
        450                 455                 460

Glu Glu Gly Lys Arg Gly Ala Arg Gly Glu Pro Gly Pro Thr Gly Leu
465                 470                 475                 480

Pro Gly Pro Pro Gly Glu Arg Gly Gly Pro Gly Ser Arg Gly Phe Pro
```

```
                485                 490                 495
Gly Ala Asp Gly Val Ala Gly Pro Lys Gly Pro Ala Gly Glu Arg Gly
            500                 505                 510

Ser Pro Gly Pro Ala Gly Pro Lys Gly Ser Pro Gly Glu Ala Gly Arg
        515                 520                 525

Pro Gly Glu Ala Gly Leu Pro Gly Ala Lys Gly Leu Thr Gly Ser Pro
        530                 535                 540

Gly Ser Pro Gly Pro Asp Gly Lys Thr Gly Pro Pro Gly Pro Ala Gly
545                 550                 555                 560

Gln Asp Gly Arg Pro Gly Pro Pro Gly Pro Pro Gly Ala Arg Gly Gln
                565                 570                 575

Ala Gly Val Met Gly Phe Pro Gly Pro Lys Gly Ala Ala Gly Glu Pro
            580                 585                 590

Gly Lys Ala Gly Glu Arg Gly Val Pro Gly Pro Pro Gly Ala Val Gly
        595                 600                 605

Pro Ala Gly Lys Asp Gly Glu Ala Gly Ala Gln Gly Pro Pro Gly Pro
        610                 615                 620

Ala Gly Pro Ala Gly Glu Arg Gly Glu Gln Gly Pro Ala Gly Ser Pro
625                 630                 635                 640

Gly Phe Gln Gly Leu Pro Gly Pro Ala Gly Pro Pro Gly Glu Ala Gly
                645                 650                 655

Lys Pro Gly Glu Gln Gly Val Pro Gly Asp Leu Gly Ala Pro Gly Pro
            660                 665                 670

Ser Gly Ala Arg Gly Glu Arg Gly Phe Pro Gly Glu Arg Gly Val Gln
        675                 680                 685

Gly Pro Pro Gly Pro Ala Gly Pro Arg Gly Ala Asn Gly Ala Pro Gly
        690                 695                 700

Asn Asp Gly Ala Lys Gly Asp Ala Gly Ala Pro Gly Ala Pro Gly Ser
705                 710                 715                 720

Gln Gly Ala Pro Gly Leu Gln Gly Met Pro Gly Glu Arg Gly Ala Ala
                725                 730                 735

Gly Leu Pro Gly Pro Lys Gly Asp Arg Gly Asp Ala Gly Pro Lys Gly
            740                 745                 750

Ala Asp Gly Ser Pro Gly Lys Asp Gly Val Arg Gly Leu Thr Gly Pro
        755                 760                 765

Ile Gly Pro Pro Gly Pro Ala Gly Ala Pro Gly Asp Lys Gly Glu Ser
        770                 775                 780

Gly Pro Ser Gly Pro Ala Gly Pro Thr Gly Ala Arg Gly Ala Pro Gly
785                 790                 795                 800

Asp Arg Gly Glu Pro Gly Pro Pro Gly Pro Ala Gly Phe Ala Gly Pro
                805                 810                 815

Pro Gly Ala Asp Gly Gln Pro Gly Ala Lys Gly Glu Pro Gly Asp Ala
            820                 825                 830

Gly Ala Lys Gly Asp Ala Gly Pro Pro Gly Pro Ala Gly Pro Ala Gly
        835                 840                 845

Pro Pro Gly Pro Ile Gly Asn Val Gly Ala Pro Gly Ala Lys Gly Ala
        850                 855                 860

Arg Gly Ser Ala Gly Pro Pro Gly Ala Thr Gly Phe Pro Gly Ala Ala
865                 870                 875                 880

Gly Arg Val Gly Pro Pro Gly Pro Ser Gly Asn Ala Gly Pro Pro Gly
                885                 890                 895

Pro Pro Gly Pro Ala Gly Lys Glu Gly Gly Lys Gly Pro Arg Gly Glu
            900                 905                 910
```

```
Thr Gly Pro Ala Gly Arg Pro Gly Glu Val Gly Pro Pro Gly Pro Pro
        915                 920                 925
Gly Pro Ala Gly Glu Lys Gly Ser Pro Gly Ala Asp Gly Pro Ala Gly
    930                 935                 940
Ala Pro Gly Thr Pro Gly Pro Gln Gly Ile Ala Gly Gln Arg Gly Val
945                 950                 955                 960
Val Gly Leu Pro Gly Gln Arg Gly Glu Arg Gly Phe Pro Gly Leu Pro
                965                 970                 975
Gly Pro Ser Gly Glu Pro Gly Lys Gln Gly Pro Ser Gly Ala Ser Gly
            980                 985                 990
Glu Arg Gly Pro Pro Gly Pro Met Gly Pro Pro Gly Leu Ala Gly Pro
        995                 1000                1005
Pro Gly Glu Ser Gly Arg Glu Gly Ala Pro Gly Ala Glu Gly Ser
    1010                1015                1020
Pro Gly Arg Asp Gly Ser Pro Gly Ala Lys Gly Asp Arg Gly Glu
    1025                1030                1035
Thr Gly Pro Ala Gly Pro Pro Gly Ala Pro Gly Ala Pro Gly Ala
    1040                1045                1050
Pro Gly Pro Val Gly Pro Ala Gly Lys Ser Gly Asp Arg Gly Glu
    1055                1060                1065
Thr Gly Pro Ala Gly Pro Ala Gly Pro Val Gly Pro Val Gly Ala
    1070                1075                1080
Arg Gly Pro Ala Gly Pro Gln Gly Pro Arg Gly Asp Lys Gly Glu
    1085                1090                1095
Thr Gly Glu Gln Gly Asp Arg Gly Ile Lys Gly His Arg Gly Phe
    1100                1105                1110
Ser Gly Leu Gln Gly Pro Pro Gly Pro Pro Gly Ser Pro Gly Glu
    1115                1120                1125
Gln Gly Pro Ser Gly Ala Ser Gly Pro Ala Gly Pro Arg Gly Pro
    1130                1135                1140
Pro Gly Ser Ala Gly Ala Pro Gly Lys Asp Gly Leu Asn Gly Leu
    1145                1150                1155
Pro Gly Pro Ile Gly Pro Pro Gly Pro Arg Gly Arg Thr Gly Asp
    1160                1165                1170
Ala Gly Pro Val Gly Pro Pro Gly Pro Pro Gly Pro Pro Gly Pro
    1175                1180                1185
Pro Gly Pro Pro Ser Ala Gly Phe Asp Phe Ser Phe Leu Pro Gln
    1190                1195                1200
Pro Pro Gln Glu Lys Ala His Asp Gly Gly Arg Tyr Tyr Arg Ala
    1205                1210                1215
Asp Asp Ala Asn Val Val Arg Asp Arg Asp Leu Glu Val Asp Thr
    1220                1225                1230
Thr Leu Lys Ser Leu Ser Gln Gln Ile Glu Asn Ile Arg Ser Pro
    1235                1240                1245
Glu Gly Ser Arg Lys Asn Pro Ala Arg Thr Cys Arg Asp Leu Lys
    1250                1255                1260
Met Cys His Ser Asp Trp Lys Ser Gly Glu Tyr Trp Ile Asp Pro
    1265                1270                1275
Asn Gln Gly Cys Asn Leu Asp Ala Ile Lys Val Phe Cys Asn Met
    1280                1285                1290
Glu Thr Gly Glu Thr Cys Val Tyr Pro Thr Gln Pro Ser Val Ala
    1295                1300                1305
```

-continued

```
Gln Lys Asn Trp Tyr Ile Ser Lys Asn Pro Lys Asp Lys Arg His
    1310                1315                1320

Val Trp Phe Gly Glu Ser Met Thr Asp Gly Phe Gln Phe Glu Tyr
    1325                1330                1335

Gly Gly Gln Gly Ser Asp Pro Ala Asp Val Ala Ile Gln Leu Thr
    1340                1345                1350

Phe Leu Arg Leu Met Ser Thr Glu Ala Ser Gln Asn Ile Thr Tyr
    1355                1360                1365

His Cys Lys Asn Ser Val Ala Tyr Met Asp Gln Gln Thr Gly Asn
    1370                1375                1380

Leu Lys Lys Ala Leu Leu Leu Gln Gly Ser Asn Glu Ile Glu Ile
    1385                1390                1395

Arg Ala Glu Gly Asn Ser Arg Phe Thr Tyr Ser Val Thr Val Asp
    1400                1405                1410

Gly Cys Thr Ser His Thr Gly Ala Trp Gly Lys Thr Val Ile Glu
    1415                1420                1425

Tyr Lys Thr Thr Lys Thr Ser Arg Leu Pro Ile Ile Asp Val Ala
    1430                1435                1440

Pro Leu Asp Val Gly Ala Pro Asp Gln Glu Phe Gly Phe Asp Val
    1445                1450                1455

Gly Pro Val Cys Phe Leu
    1460

<210> SEQ ID NO 57
<211> LENGTH: 1460
<212> TYPE: PRT
<213> ORGANISM: Canis familiaris

<400> SEQUENCE: 57

Met Phe Ser Phe Val Asp Leu Arg Leu Leu Leu Leu Ala Ala Thr
1               5                   10                  15

Ala Leu Leu Thr His Gly Gln Glu Gly Gln Glu Glu Asp Ile Pro
                20                  25                  30

Pro Val Thr Cys Val Gln Asn Gly Leu Arg Tyr Tyr Asp Arg Asp Val
                35                  40                  45

Trp Lys Pro Glu Ala Cys Arg Ile Cys Val Cys Asp Asn Gly Asn Val
    50                  55                  60

Leu Cys Asp Asp Val Ile Cys Asp Glu Thr Lys Asn Cys Pro Gly Ala
65                  70                  75                  80

Gln Val Pro Pro Gly Glu Cys Cys Pro Val Cys Pro Asp Gly Glu Ala
                85                  90                  95

Ser Pro Thr Asp Gln Glu Thr Thr Gly Val Glu Gly Pro Lys Gly Asp
                100                 105                 110

Thr Gly Pro Arg Gly Pro Arg Gly Pro Ala Gly Pro Pro Gly Arg Asp
                115                 120                 125

Gly Ile Pro Gly Gln Pro Gly Leu Pro Gly Pro Pro Gly Pro Pro Gly
                130                 135                 140

Pro Pro Gly Pro Pro Gly Leu Gly Gly Asn Phe Ala Pro Gln Met Ser
145                 150                 155                 160

Tyr Gly Tyr Asp Glu Lys Ser Thr Gly Gly Ile Ser Val Pro Gly Pro
                165                 170                 175

Met Gly Pro Ser Gly Pro Arg Gly Leu Pro Gly Pro Pro Gly Ala Pro
                180                 185                 190

Gly Pro Gln Gly Phe Gln Gly Pro Pro Gly Glu Pro Gly Glu Pro Gly
                195                 200                 205
```

```
Ala Ser Gly Pro Met Gly Pro Arg Gly Pro Pro Gly Lys
    210                 215                 220

Asn Gly Asp Asp Gly Glu Ala Gly Lys Pro Gly Arg Pro Gly Glu Arg
225                 230                 235                 240

Gly Pro Pro Gly Pro Gln Gly Ala Arg Gly Leu Pro Gly Thr Ala Gly
                245                 250                 255

Leu Pro Gly Met Lys Gly His Arg Gly Phe Ser Gly Leu Asp Gly Ala
                260                 265                 270

Lys Gly Asp Ala Gly Pro Ala Gly Pro Lys Gly Glu Pro Gly Ser Pro
                275                 280                 285

Gly Glu Asn Gly Ala Pro Gly Gln Met Gly Pro Arg Gly Leu Pro Gly
                290                 295                 300

Glu Arg Gly Arg Pro Gly Ala Pro Gly Pro Ala Gly Ala Arg Gly Asn
305                 310                 315                 320

Asp Gly Ala Thr Gly Ala Ala Gly Pro Pro Gly Pro Thr Gly Pro Ala
                325                 330                 335

Gly Pro Pro Gly Phe Pro Gly Ala Val Gly Ala Lys Gly Glu Ala Gly
                340                 345                 350

Pro Gln Gly Ala Arg Gly Ser Glu Gly Pro Gln Gly Val Arg Gly Glu
                355                 360                 365

Pro Gly Pro Pro Gly Pro Ala Gly Ala Ala Gly Pro Ala Gly Asn Pro
                370                 375                 380

Gly Ala Asp Gly Gln Pro Gly Ala Lys Gly Ala Asn Gly Ala Pro Gly
385                 390                 395                 400

Ile Ala Gly Ala Pro Gly Phe Pro Gly Ala Arg Gly Pro Ser Gly Pro
                405                 410                 415

Gln Gly Pro Ser Gly Pro Pro Gly Pro Lys Gly Asn Ser Gly Glu Pro
                420                 425                 430

Gly Ala Pro Gly Asn Lys Gly Asp Thr Gly Ala Lys Gly Glu Pro Gly
                435                 440                 445

Pro Thr Gly Ile Gln Gly Pro Pro Gly Pro Ala Gly Glu Glu Gly Lys
    450                 455                 460

Arg Gly Ala Arg Gly Glu Pro Gly Pro Thr Gly Leu Pro Gly Pro Pro
465                 470                 475                 480

Gly Glu Arg Gly Gly Pro Gly Ser Arg Gly Phe Pro Gly Ala Asp Gly
                485                 490                 495

Val Ala Gly Pro Lys Gly Pro Ala Gly Glu Arg Gly Ser Pro Gly Pro
                500                 505                 510

Ala Gly Pro Lys Gly Ser Pro Gly Glu Ala Gly Arg Pro Gly Glu Ala
                515                 520                 525

Gly Leu Pro Gly Ala Lys Gly Leu Thr Gly Ser Pro Gly Ser Pro Gly
                530                 535                 540

Pro Asp Gly Lys Thr Gly Pro Pro Gly Pro Ala Gly Gln Asp Gly Arg
545                 550                 555                 560

Pro Gly Pro Pro Gly Pro Pro Gly Ala Arg Gly Gln Ala Gly Val Met
                565                 570                 575

Gly Phe Pro Gly Pro Lys Gly Ala Ala Gly Glu Pro Gly Lys Ala Gly
                580                 585                 590

Glu Arg Gly Val Pro Gly Pro Pro Gly Ala Val Gly Pro Ala Gly Lys
                595                 600                 605

Asp Gly Glu Ala Gly Ala Gln Gly Pro Pro Gly Pro Ala Gly Pro Ala
610                 615                 620
```

-continued

```
Gly Glu Arg Gly Glu Gln Gly Pro Ala Gly Ser Pro Gly Phe Gln Gly
625                 630                 635                 640

Leu Pro Gly Pro Ala Gly Pro Pro Gly Glu Ala Gly Lys Pro Gly Glu
            645                 650                 655

Gln Gly Val Pro Gly Asp Leu Gly Ala Pro Gly Pro Ser Gly Ala Arg
            660                 665                 670

Gly Glu Arg Gly Phe Pro Gly Glu Arg Gly Val Gln Gly Pro Pro Gly
        675                 680                 685

Pro Ala Gly Pro Arg Gly Ala Asn Gly Ala Pro Gly Asn Asp Gly Ala
        690                 695                 700

Lys Gly Asp Ala Gly Ala Pro Gly Ala Pro Gly Ser Gln Gly Ala Pro
705                 710                 715                 720

Gly Leu Gln Gly Met Pro Gly Glu Arg Gly Ala Ala Gly Leu Pro Gly
                725                 730                 735

Pro Lys Gly Asp Arg Gly Asp Ala Gly Pro Lys Gly Ala Asp Gly Ser
            740                 745                 750

Pro Gly Lys Asp Gly Val Arg Gly Leu Thr Gly Pro Ile Gly Pro Pro
        755                 760                 765

Gly Pro Ala Gly Ala Pro Gly Asp Lys Gly Glu Ala Gly Pro Ser Gly
        770                 775                 780

Pro Ala Gly Pro Thr Gly Ala Arg Gly Ala Pro Gly Asp Arg Gly Glu
785                 790                 795                 800

Pro Gly Pro Pro Gly Pro Ala Gly Phe Ala Gly Pro Pro Gly Ala Asp
                805                 810                 815

Gly Gln Pro Gly Ala Lys Gly Glu Pro Gly Asp Ala Gly Ala Lys Gly
            820                 825                 830

Asp Ala Gly Pro Pro Gly Pro Ala Gly Pro Thr Gly Pro Pro Gly Pro
        835                 840                 845

Ile Gly Asn Val Gly Ala Pro Gly Pro Lys Gly Ala Arg Gly Ser Ala
        850                 855                 860

Gly Pro Pro Gly Ala Thr Gly Phe Pro Gly Ala Ala Gly Arg Val Gly
865                 870                 875                 880

Pro Pro Gly Pro Ser Gly Asn Ala Gly Pro Pro Gly Pro Pro Gly Pro
                885                 890                 895

Ala Gly Lys Glu Gly Gly Lys Gly Ala Arg Gly Glu Thr Gly Pro Ala
            900                 905                 910

Gly Arg Pro Gly Glu Val Gly Pro Pro Gly Pro Pro Gly Pro Ala Gly
        915                 920                 925

Glu Lys Gly Ser Pro Gly Ala Asp Gly Pro Ala Gly Ala Pro Gly Thr
        930                 935                 940

Pro Gly Pro Gln Gly Ile Ala Gly Gln Arg Gly Val Val Gly Leu Pro
945                 950                 955                 960

Gly Gln Arg Gly Glu Arg Gly Phe Pro Gly Leu Pro Gly Pro Ser Gly
                965                 970                 975

Glu Pro Gly Lys Gln Gly Pro Ser Gly Thr Ser Gly Glu Arg Gly Pro
            980                 985                 990

Pro Gly Pro Met Gly Pro Pro Gly  Leu Ala Gly Pro Pro  Gly Glu Ser
            995                 1000                1005

Gly Arg  Glu Gly Ser Pro Gly  Ala Glu Gly Ser Pro  Gly Arg Asp
     1010                1015                1020

Gly Ser  Pro Gly Pro Lys Gly  Asp Arg Gly Glu Thr  Gly Pro Ala
     1025                1030                1035

Gly Pro  Pro Gly Ala Pro Gly  Ala Pro Gly Ala Pro  Gly Pro Val
```

```
            1040                1045                1050
Gly Pro Ala Gly Lys Asn Gly Asp Arg Gly Glu Thr Gly Pro Ala
            1055                1060                1065
Gly Pro Ala Gly Pro Ile Gly Pro Val Gly Ala Arg Gly Pro Ala
            1070                1075                1080
Gly Pro Gln Gly Pro Arg Gly Asp Lys Gly Glu Thr Gly Glu Gln
            1085                1090                1095
Gly Asp Arg Gly Ile Lys Gly His Arg Gly Phe Ser Gly Leu Gln
            1100                1105                1110
Gly Pro Pro Gly Pro Pro Gly Ser Pro Gly Glu Gln Gly Pro Ser
            1115                1120                1125
Gly Ala Ser Gly Pro Ala Gly Pro Arg Gly Pro Pro Gly Ser Ala
            1130                1135                1140
Gly Ser Pro Gly Lys Asp Gly Leu Asn Gly Leu Pro Gly Pro Ile
            1145                1150                1155
Gly Pro Pro Gly Pro Arg Gly Arg Thr Gly Asp Ala Gly Pro Val
            1160                1165                1170
Gly Pro Pro Gly Pro Pro Gly Pro Pro Gly Pro Pro Gly Pro Pro
            1175                1180                1185
Ser Gly Gly Phe Asp Phe Ser Phe Leu Pro Gln Pro Pro Gln Glu
            1190                1195                1200
Lys Ala His Asp Gly Gly Arg Tyr Tyr Arg Ala Asp Asp Ala Asn
            1205                1210                1215
Val Val Arg Asp Arg Asp Leu Glu Val Asp Thr Thr Leu Lys Ser
            1220                1225                1230
Leu Ser Gln Gln Ile Glu Asn Ile Arg Ser Pro Glu Gly Ser Arg
            1235                1240                1245
Lys Asn Pro Ala Arg Thr Cys Arg Asp Leu Lys Met Cys His Ser
            1250                1255                1260
Asp Trp Lys Ser Gly Glu Tyr Trp Ile Asp Pro Asn Gln Gly Cys
            1265                1270                1275
Asn Leu Asp Ala Ile Lys Val Phe Cys Asn Met Glu Thr Gly Glu
            1280                1285                1290
Thr Cys Val Tyr Pro Thr Gln Pro Gln Val Ala Gln Lys Asn Trp
            1295                1300                1305
Tyr Ile Ser Lys Asn Pro Lys Glu Lys Arg His Val Trp Tyr Gly
            1310                1315                1320
Glu Ser Met Thr Asp Gly Phe Gln Phe Glu Tyr Gly Gly Gln Gly
            1325                1330                1335
Ser Asp Pro Ala Asp Val Ala Ile Gln Leu Thr Phe Leu Arg Leu
            1340                1345                1350
Met Ser Thr Glu Ala Ser Gln Asn Ile Thr Tyr His Cys Lys Asn
            1355                1360                1365
Ser Val Ala Tyr Met Asp Gln Gln Thr Gly Asn Leu Lys Lys Ala
            1370                1375                1380
Leu Leu Leu Gln Gly Ser Asn Glu Ile Glu Ile Arg Ala Glu Gly
            1385                1390                1395
Asn Ser Arg Phe Thr Tyr Ser Val Thr Tyr Asp Gly Cys Thr Ser
            1400                1405                1410
His Thr Gly Ala Trp Gly Lys Thr Val Ile Glu Tyr Lys Thr Thr
            1415                1420                1425
Lys Thr Ser Arg Leu Pro Ile Ile Asp Val Ala Pro Leu Asp Val
            1430                1435                1440
```

Gly Ala Pro Asp Gln Glu Phe Gly Met Asp Ile Gly Pro Val Cys
            1445                1450                1455

Phe Leu
    1460

<210> SEQ ID NO 58
<211> LENGTH: 1463
<212> TYPE: PRT
<213> ORGANISM: Bos taurus

<400> SEQUENCE: 58

Met Phe Ser Phe Val Asp Leu Arg Leu Leu Leu Leu Ala Ala Thr
1                 5                  10                  15

Ala Leu Leu Thr His Gly Gln Glu Gly Gln Glu Glu Gly Gln Glu
                20                  25                  30

Glu Asp Ile Pro Pro Val Thr Cys Val Gln Asn Gly Leu Arg Tyr His
            35                  40                  45

Asp Arg Asp Val Trp Lys Pro Val Pro Cys Gln Ile Cys Val Cys Asp
50                  55                  60

Asn Gly Asn Val Leu Cys Asp Asp Val Ile Cys Asp Glu Leu Lys Asp
65                  70                  75                  80

Cys Pro Asn Ala Lys Val Pro Thr Asp Glu Cys Cys Pro Val Cys Pro
                85                  90                  95

Glu Gly Gln Glu Ser Pro Thr Asp Gln Glu Thr Thr Gly Val Glu Gly
                100                 105                 110

Pro Lys Gly Asp Thr Gly Pro Arg Gly Pro Arg Gly Pro Ala Gly Pro
            115                 120                 125

Pro Gly Arg Asp Gly Ile Pro Gly Gln Pro Gly Leu Pro Gly Pro Pro
        130                 135                 140

Gly Pro Pro Gly Pro Pro Gly Pro Pro Gly Leu Gly Gly Asn Phe Ala
145                 150                 155                 160

Pro Gln Leu Ser Tyr Gly Tyr Asp Glu Lys Ser Thr Gly Ile Ser Val
                165                 170                 175

Pro Gly Pro Met Gly Pro Ser Gly Pro Arg Gly Leu Pro Gly Pro Pro
            180                 185                 190

Gly Ala Pro Gly Pro Gln Gly Phe Gln Gly Pro Pro Gly Glu Pro Gly
        195                 200                 205

Glu Pro Gly Ala Ser Gly Pro Met Gly Pro Arg Gly Pro Pro Gly Pro
    210                 215                 220

Pro Gly Lys Asn Gly Asp Asp Gly Glu Ala Gly Lys Pro Gly Arg Pro
225                 230                 235                 240

Gly Glu Arg Gly Pro Pro Gly Pro Gln Gly Ala Arg Gly Leu Pro Gly
                245                 250                 255

Thr Ala Gly Leu Pro Gly Met Lys Gly His Arg Gly Phe Ser Gly Leu
            260                 265                 270

Asp Gly Ala Lys Gly Asp Ala Gly Pro Ala Gly Pro Lys Gly Glu Pro
        275                 280                 285

Gly Ser Pro Gly Glu Asn Gly Ala Pro Gly Gln Met Gly Pro Arg Gly
    290                 295                 300

Leu Pro Gly Glu Arg Gly Arg Pro Gly Ala Pro Gly Pro Ala Gly Ala
305                 310                 315                 320

Arg Gly Asn Asp Gly Ala Thr Gly Ala Ala Gly Pro Pro Gly Pro Thr
                325                 330                 335

Gly Pro Ala Gly Pro Pro Gly Phe Pro Gly Ala Val Gly Ala Lys Gly

```
                340                 345                 350
Glu Gly Gly Pro Gln Gly Pro Arg Gly Ser Glu Gly Pro Gln Gly Val
            355                 360                 365

Arg Gly Glu Pro Gly Pro Pro Gly Ala Gly Ala Ala Gly Pro Ala
370                 375                 380

Gly Asn Pro Gly Ala Asp Gly Gln Pro Gly Ala Lys Gly Ala Asn Gly
385                 390                 395                 400

Ala Pro Gly Ile Ala Gly Ala Pro Gly Phe Pro Gly Ala Arg Gly Pro
                405                 410                 415

Ser Gly Pro Gln Gly Pro Ser Gly Pro Pro Gly Pro Lys Gly Asn Ser
            420                 425                 430

Gly Glu Pro Gly Ala Pro Gly Ser Lys Gly Asp Thr Gly Ala Lys Gly
            435                 440                 445

Glu Pro Gly Pro Thr Gly Ile Gln Gly Pro Pro Gly Pro Ala Gly Glu
            450                 455                 460

Glu Gly Lys Arg Gly Ala Arg Gly Glu Pro Gly Pro Ala Gly Leu Pro
465                 470                 475                 480

Gly Pro Pro Gly Glu Arg Gly Gly Pro Gly Ser Arg Gly Phe Pro Gly
                485                 490                 495

Ala Asp Gly Val Ala Gly Pro Lys Gly Pro Ala Gly Glu Arg Gly Ala
            500                 505                 510

Pro Gly Pro Ala Gly Pro Lys Gly Ser Pro Gly Glu Ala Gly Arg Pro
            515                 520                 525

Gly Glu Ala Gly Leu Pro Gly Ala Lys Gly Leu Thr Gly Ser Pro Gly
            530                 535                 540

Ser Pro Gly Pro Asp Gly Lys Thr Gly Pro Pro Gly Pro Ala Gly Gln
545                 550                 555                 560

Asp Gly Arg Pro Gly Pro Pro Gly Pro Pro Gly Ala Arg Gly Gln Ala
                565                 570                 575

Gly Val Met Gly Phe Pro Gly Pro Lys Gly Ala Ala Gly Glu Pro Gly
            580                 585                 590

Lys Ala Gly Glu Arg Gly Val Pro Gly Pro Pro Gly Ala Val Gly Pro
            595                 600                 605

Ala Gly Lys Asp Gly Glu Ala Gly Ala Gln Gly Pro Pro Gly Pro Ala
            610                 615                 620

Gly Pro Ala Gly Glu Arg Gly Glu Gln Gly Pro Ala Gly Ser Pro Gly
625                 630                 635                 640

Phe Gln Gly Leu Pro Gly Pro Ala Gly Pro Pro Gly Glu Ala Gly Lys
                645                 650                 655

Pro Gly Glu Gln Gly Val Pro Gly Asp Leu Gly Ala Pro Gly Pro Ser
            660                 665                 670

Gly Ala Arg Gly Glu Arg Gly Phe Pro Gly Glu Arg Gly Val Gln Gly
            675                 680                 685

Pro Pro Gly Pro Ala Gly Pro Arg Gly Ala Asn Gly Ala Pro Gly Asn
            690                 695                 700

Asp Gly Ala Lys Gly Asp Ala Gly Ala Pro Gly Ala Pro Gly Ser Gln
705                 710                 715                 720

Gly Ala Pro Gly Leu Gln Gly Met Pro Gly Glu Arg Gly Ala Ala Gly
                725                 730                 735

Leu Pro Gly Pro Lys Gly Asp Arg Gly Asp Ala Gly Pro Lys Gly Ala
            740                 745                 750

Asp Gly Ala Pro Gly Lys Asp Gly Val Arg Gly Leu Thr Gly Pro Ile
            755                 760                 765
```

Gly Pro Pro Gly Pro Ala Gly Ala Pro Gly Asp Lys Gly Glu Ala Gly
        770                 775                 780

Pro Ser Gly Pro Ala Gly Pro Thr Gly Ala Arg Gly Ala Pro Gly Asp
785                 790                 795                 800

Arg Gly Glu Pro Gly Pro Gly Pro Ala Gly Phe Ala Gly Pro Pro
            805                 810                 815

Gly Ala Asp Gly Gln Pro Gly Ala Lys Gly Glu Pro Gly Asp Ala Gly
                820                 825                 830

Ala Lys Gly Asp Ala Gly Pro Pro Gly Pro Ala Gly Pro Ala Gly Pro
        835                 840                 845

Pro Gly Pro Ile Gly Asn Val Gly Ala Pro Gly Pro Lys Gly Ala Arg
        850                 855                 860

Gly Ser Ala Gly Pro Pro Gly Ala Thr Gly Phe Pro Gly Ala Ala Gly
865                 870                 875                 880

Arg Val Gly Pro Pro Gly Pro Ser Gly Asn Ala Gly Pro Pro Gly Pro
            885                 890                 895

Pro Gly Pro Ala Gly Lys Glu Gly Ser Lys Gly Pro Arg Gly Glu Thr
        900                 905                 910

Gly Pro Ala Gly Arg Pro Gly Glu Val Gly Pro Pro Gly Pro Pro Gly
        915                 920                 925

Pro Ala Gly Glu Lys Gly Ala Pro Gly Ala Asp Gly Pro Ala Gly Ala
930                 935                 940

Pro Gly Thr Pro Gly Pro Gln Gly Ile Ala Gly Gln Arg Gly Val Val
945                 950                 955                 960

Gly Leu Pro Gly Gln Arg Gly Glu Arg Gly Phe Pro Gly Leu Pro Gly
            965                 970                 975

Pro Ser Gly Glu Pro Gly Lys Gln Gly Pro Ser Gly Ala Ser Gly Glu
        980                 985                 990

Arg Gly Pro Pro Gly Pro Met Gly Pro Pro Gly Leu Ala Gly Pro Pro
            995                 1000                1005

Gly Glu Ser Gly Arg Glu Gly Ala Pro Gly Ala Glu Gly Ser Pro
        1010                1015                1020

Gly Arg Asp Gly Ser Pro Gly Ala Lys Gly Asp Arg Gly Glu Thr
        1025                1030                1035

Gly Pro Ala Gly Pro Pro Gly Ala Pro Gly Ala Pro Gly Ala Pro
        1040                1045                1050

Gly Pro Val Gly Pro Ala Gly Lys Ser Gly Asp Arg Gly Glu Thr
        1055                1060                1065

Gly Pro Ala Gly Pro Ala Gly Pro Ile Gly Pro Val Gly Ala Arg
        1070                1075                1080

Gly Pro Ala Gly Pro Gln Gly Pro Arg Gly Asp Lys Gly Glu Thr
        1085                1090                1095

Gly Glu Gln Gly Asp Arg Gly Ile Lys Gly His Arg Gly Phe Ser
        1100                1105                1110

Gly Leu Gln Gly Pro Pro Gly Pro Pro Gly Ser Pro Gly Glu Gln
        1115                1120                1125

Gly Pro Ser Gly Ala Ser Gly Pro Ala Gly Pro Arg Gly Pro Pro
        1130                1135                1140

Gly Ser Ala Gly Ser Pro Gly Lys Asp Gly Leu Asn Gly Leu Pro
        1145                1150                1155

Gly Pro Ile Gly Pro Pro Gly Pro Arg Gly Arg Thr Gly Asp Ala
        1160                1165                1170

-continued

Gly Pro Ala Gly Pro Pro Gly Pro Pro Gly Pro Pro
1175                1180                1185

Gly Pro Pro Ser Gly Gly Tyr Asp Leu Ser Phe Leu Pro Gln Pro
1190                1195                1200

Pro Gln Glu Lys Ala His Asp Gly Gly Arg Tyr Tyr Arg Ala Asp
1205                1210                1215

Asp Ala Asn Val Val Arg Asp Arg Asp Leu Glu Val Asp Thr Thr
1220                1225                1230

Leu Lys Ser Leu Ser Gln Gln Ile Glu Asn Ile Arg Ser Pro Glu
1235                1240                1245

Gly Ser Arg Lys Asn Pro Ala Arg Thr Cys Arg Asp Leu Lys Met
1250                1255                1260

Cys His Ser Asp Trp Lys Ser Gly Glu Tyr Trp Ile Asp Pro Asn
1265                1270                1275

Gln Gly Cys Asn Leu Asp Ala Ile Lys Val Phe Cys Asn Met Glu
1280                1285                1290

Thr Gly Glu Thr Cys Val Tyr Pro Thr Gln Pro Ser Val Ala Gln
1295                1300                1305

Lys Asn Trp Tyr Ile Ser Lys Asn Pro Lys Glu Lys Arg His Val
1310                1315                1320

Trp Tyr Gly Glu Ser Met Thr Gly Gly Phe Gln Phe Glu Tyr Gly
1325                1330                1335

Gly Gln Gly Ser Asp Pro Ala Asp Val Ala Ile Gln Leu Thr Phe
1340                1345                1350

Leu Arg Leu Met Ser Thr Glu Ala Ser Gln Asn Ile Thr Tyr His
1355                1360                1365

Cys Lys Asn Ser Val Ala Tyr Met Asp Gln Gln Thr Gly Asn Leu
1370                1375                1380

Lys Lys Ala Leu Leu Leu Gln Gly Ser Asn Glu Ile Glu Ile Arg
1385                1390                1395

Ala Glu Gly Asn Ser Arg Phe Thr Tyr Ser Val Thr Tyr Asp Gly
1400                1405                1410

Cys Thr Ser His Thr Gly Ala Trp Gly Lys Thr Val Ile Glu Tyr
1415                1420                1425

Lys Thr Thr Lys Thr Ser Arg Leu Pro Ile Ile Asp Val Ala Pro
1430                1435                1440

Leu Asp Val Gly Ala Pro Asp Gln Glu Phe Gly Phe Asp Val Gly
1445                1450                1455

Pro Ala Cys Phe Leu
1460

<210> SEQ ID NO 59
<211> LENGTH: 3075
<212> TYPE: PRT
<213> ORGANISM: Homo sapiens

<400> SEQUENCE: 59

Met Arg Gly Gly Val Leu Leu Val Leu Leu Leu Cys Val Ala Ala Gln
1               5                   10                  15

Cys Arg Gln Arg Gly Leu Phe Pro Ala Ile Leu Asn Leu Ala Ser Asn
                20                  25                  30

Ala His Ile Ser Thr Asn Ala Thr Cys Gly Glu Lys Gly Pro Glu Met
            35                  40                  45

Phe Cys Lys Leu Val Glu His Val Pro Gly Arg Pro Val Arg Asn Pro
        50                  55                  60

```
Gln Cys Arg Ile Cys Asp Gly Asn Ser Ala Asn Pro Arg Glu Arg His
 65                  70                  75                  80

Pro Ile Ser His Ala Ile Asp Gly Thr Asn Asn Trp Trp Gln Ser Pro
                 85                  90                  95

Ser Ile Gln Asn Gly Arg Glu Tyr His Trp Val Thr Ile Thr Leu Asp
            100                 105                 110

Leu Arg Gln Val Phe Gln Val Ala Tyr Val Ile Ile Lys Ala Ala Asn
        115                 120                 125

Ala Pro Arg Pro Gly Asn Trp Ile Leu Glu Arg Ser Leu Asp Gly Thr
    130                 135                 140

Thr Phe Ser Pro Trp Gln Tyr Ala Val Ser Asp Ser Glu Cys Leu
145                 150                 155                 160

Ser Arg Tyr Asn Ile Thr Pro Arg Arg Gly Pro Pro Thr Tyr Arg Ala
                165                 170                 175

Asp Asp Glu Val Ile Cys Thr Ser Tyr Tyr Ser Arg Leu Val Pro Leu
            180                 185                 190

Glu His Gly Glu Ile His Thr Ser Leu Ile Asn Gly Arg Pro Ser Ala
        195                 200                 205

Asp Asp Leu Ser Pro Lys Leu Leu Glu Phe Thr Ser Ala Arg Tyr Ile
210                 215                 220

Arg Leu Arg Leu Gln Arg Ile Arg Thr Leu Asn Ala Asp Leu Met Thr
225                 230                 235                 240

Leu Ser His Arg Glu Pro Lys Glu Leu Asp Pro Ile Val Thr Arg Arg
                245                 250                 255

Tyr Tyr Tyr Ser Ile Lys Asp Ile Ser Val Gly Gly Met Cys Ile Cys
            260                 265                 270

Tyr Gly His Ala Ser Ser Cys Pro Trp Asp Glu Thr Thr Lys Lys Leu
        275                 280                 285

Gln Cys Gln Cys Glu His Asn Thr Cys Gly Glu Ser Cys Asn Arg Cys
    290                 295                 300

Cys Pro Gly Tyr His Gln Gln Pro Trp Arg Pro Gly Thr Val Ser Ser
305                 310                 315                 320

Gly Asn Thr Cys Glu Ala Cys Asn Cys His Asn Lys Ala Lys Asp Cys
                325                 330                 335

Tyr Tyr Asp Glu Ser Val Ala Lys Gln Lys Ser Leu Asn Thr Ala
            340                 345                 350

Gly Gln Phe Arg Gly Gly Val Cys Ile Asn Cys Leu Gln Asn Thr
        355                 360                 365

Met Gly Ile Asn Cys Glu Thr Cys Ile Asp Gly Tyr Tyr Arg Pro His
    370                 375                 380

Lys Val Ser Pro Tyr Glu Asp Glu Pro Cys Arg Pro Cys Asn Cys Asp
385                 390                 395                 400

Pro Val Gly Ser Leu Ser Ser Val Cys Ile Lys Asp Asp Leu His Ser
                405                 410                 415

Asp Leu His Asn Gly Lys Gln Pro Gly Gln Cys Pro Cys Lys Glu Gly
            420                 425                 430

Tyr Thr Gly Glu Lys Cys Asp Arg Cys Gln Leu Gly Tyr Lys Asp Tyr
        435                 440                 445

Pro Thr Cys Val Ser Cys Gly Cys Asn Pro Val Gly Ser Ala Ser Asp
    450                 455                 460

Glu Pro Cys Thr Gly Pro Cys Val Cys Lys Glu Asn Val Glu Gly Lys
465                 470                 475                 480
```

-continued

Ala Cys Asp Arg Cys Lys Pro Gly Phe Tyr Asn Leu Lys Glu Lys Asn
                485                 490                 495
Pro Arg Gly Cys Ser Glu Cys Phe Cys Phe Gly Val Ser Asp Val Cys
            500                 505                 510
Ser Ser Leu Ser Trp Pro Val Gly Gln Val Asn Ser Met Ser Gly Trp
        515                 520                 525
Leu Val Thr Asp Leu Ile Ser Pro Arg Lys Ile Pro Ser Gln Gln Asp
    530                 535                 540
Ala Leu Gly Gly Arg His Gln Val Ser Ile Asn Asn Thr Ala Val Met
545                 550                 555                 560
Gln Arg Leu Ala Pro Lys Tyr Tyr Trp Ala Ala Pro Glu Ala Tyr Leu
                565                 570                 575
Gly Asn Lys Leu Thr Ala Phe Gly Gly Phe Leu Lys Tyr Thr Val Ser
            580                 585                 590
Tyr Asp Ile Pro Val Glu Thr Val Asp Ser Asn Leu Met Ser His Ala
        595                 600                 605
Asp Val Ile Ile Lys Gly Asn Gly Leu Thr Leu Ser Thr Gln Ala Glu
    610                 615                 620
Gly Leu Ser Leu Gln Pro Tyr Glu Glu Tyr Leu Asn Val Val Arg Leu
625                 630                 635                 640
Val Pro Glu Asn Phe Gln Asp Phe His Ser Lys Arg Gln Ile Asp Arg
                645                 650                 655
Asp Gln Leu Met Thr Val Leu Ala Asn Val Thr His Leu Leu Ile Arg
            660                 665                 670
Ala Asn Tyr Asn Ser Ala Lys Met Ala Leu Tyr Arg Leu Glu Ser Val
        675                 680                 685
Ser Leu Asp Ile Ala Ser Ser Asn Ala Ile Asp Leu Val Val Ala Ala
    690                 695                 700
Asp Val Glu His Cys Glu Cys Pro Gln Gly Tyr Thr Gly Thr Ser Cys
705                 710                 715                 720
Glu Ser Cys Leu Ser Gly Tyr Tyr Arg Val Asp Gly Ile Leu Phe Gly
                725                 730                 735
Gly Ile Cys Gln Pro Cys Glu Cys His Gly His Ala Ala Glu Cys Asn
            740                 745                 750
Val His Gly Val Cys Ile Ala Cys Ala His Asn Thr Thr Gly Val His
        755                 760                 765
Cys Glu Gln Cys Leu Pro Gly Phe Tyr Gly Glu Pro Ser Arg Gly Thr
    770                 775                 780
Pro Gly Asp Cys Gln Pro Cys Ala Cys Pro Leu Thr Ile Ala Ser Asn
785                 790                 795                 800
Asn Phe Ser Pro Thr Cys His Leu Asn Asp Gly Asp Glu Val Val Cys
                805                 810                 815
Asp Trp Cys Ala Pro Gly Tyr Ser Gly Ala Trp Cys Glu Arg Cys Ala
            820                 825                 830
Asp Gly Tyr Tyr Gly Asn Pro Thr Val Pro Gly Glu Ser Cys Val Pro
        835                 840                 845
Cys Asp Cys Ser Gly Asn Val Asp Pro Ser Glu Ala Gly His Cys Asp
    850                 855                 860
Ser Val Thr Gly Glu Cys Leu Lys Cys Leu Gly Asn Thr Asp Gly Ala
865                 870                 875                 880
His Cys Glu Arg Cys Ala Asp Gly Phe Tyr Gly Asp Ala Val Thr Ala
                885                 890                 895
Lys Asn Cys Arg Ala Cys Glu Cys His Val Lys Gly Ser His Ser Ala

```
              900             905             910
Val Cys His Leu Glu Thr Gly Leu Cys Asp Cys Lys Pro Asn Val Thr
            915             920             925
Gly Gln Gln Cys Asp Gln Cys Leu His Gly Tyr Tyr Gly Leu Asp Ser
            930             935             940
Gly His Gly Cys Arg Pro Cys Asn Cys Ser Val Ala Gly Ser Val Ser
945             950             955             960
Asp Gly Cys Thr Asp Glu Gly Gln Cys His Cys Val Pro Gly Val Ala
            965             970             975
Gly Lys Arg Cys Asp Arg Cys Ala His Gly Phe Tyr Ala Tyr Gln Asp
            980             985             990
Gly Ser Cys Thr Pro Cys Asp Cys Pro His Thr Gln Asn Thr Cys Asp
            995            1000            1005
Pro Glu Thr Gly Glu Cys Val Cys Pro Pro His Thr Gln Gly Val
           1010            1015            1020
Lys Cys Glu Glu Cys Glu Asp Gly His Trp Gly Tyr Asp Ala Glu
           1025            1030            1035
Val Gly Cys Gln Ala Cys Asn Cys Ser Leu Val Gly Ser Thr His
           1040            1045            1050
His Arg Cys Asp Val Val Thr Gly His Cys Gln Cys Lys Ser Lys
           1055            1060            1065
Phe Gly Gly Arg Ala Cys Asp Gln Cys Ser Leu Gly Tyr Arg Asp
           1070            1075            1080
Phe Pro Asp Cys Val Pro Cys Asp Cys Asp Leu Arg Gly Thr Ser
           1085            1090            1095
Gly Asp Ala Cys Asn Leu Glu Gln Gly Leu Cys Gly Cys Val Glu
           1100            1105            1110
Glu Thr Gly Ala Cys Pro Cys Lys Glu Asn Val Phe Gly Pro Gln
           1115            1120            1125
Cys Asn Glu Cys Arg Glu Gly Thr Phe Ala Leu Arg Ala Asp Asn
           1130            1135            1140
Pro Leu Gly Cys Ser Pro Cys Phe Cys Ser Gly Leu Ser His Leu
           1145            1150            1155
Cys Ser Glu Leu Glu Asp Tyr Val Arg Thr Pro Val Thr Leu Gly
           1160            1165            1170
Ser Asp Gln Pro Leu Leu Arg Val Val Ser Gln Ser Asn Leu Arg
           1175            1180            1185
Gly Thr Thr Glu Gly Val Tyr Tyr Gln Ala Pro Asp Phe Leu Leu
           1190            1195            1200
Asp Ala Ala Thr Val Arg Gln His Ile Arg Ala Glu Pro Phe Tyr
           1205            1210            1215
Trp Arg Leu Pro Gln Gln Phe Gln Gly Asp Gln Leu Met Ala Tyr
           1220            1225            1230
Gly Gly Lys Leu Lys Tyr Ser Val Ala Phe Tyr Ser Leu Asp Gly
           1235            1240            1245
Val Gly Thr Ser Asn Phe Glu Pro Gln Val Leu Ile Lys Gly Gly
           1250            1255            1260
Arg Ile Arg Lys Gln Val Ile Tyr Met Asp Ala Pro Ala Pro Glu
           1265            1270            1275
Asn Gly Val Arg Gln Glu Gln Glu Val Ala Met Arg Glu Asn Phe
           1280            1285            1290
Trp Lys Tyr Phe Asn Ser Val Ser Glu Lys Pro Val Thr Arg Glu
           1295            1300            1305
```

-continued

```
Asp Phe Met Ser Val Leu Ser Asp Ile Glu Tyr Ile Leu Ile Lys
1310                1315                1320

Ala Ser Tyr Gly Gln Gly Leu Gln Gln Ser Arg Ile Ser Asp Ile
1325                1330                1335

Ser Met Glu Val Gly Arg Lys Ala Glu Lys Leu His Pro Glu Glu
1340                1345                1350

Glu Val Ala Ser Leu Leu Glu Asn Cys Val Cys Pro Pro Gly Thr
1355                1360                1365

Val Gly Phe Ser Cys Gln Asp Cys Ala Pro Gly Tyr His Arg Gly
1370                1375                1380

Lys Leu Pro Ala Gly Ser Asp Arg Gly Pro Arg Pro Leu Val Ala
1385                1390                1395

Pro Cys Val Pro Cys Ser Cys Asn Asn His Ser Asp Thr Cys Asp
1400                1405                1410

Pro Asn Thr Gly Lys Cys Leu Asn Cys Gly Asp Asn Thr Ala Gly
1415                1420                1425

Asp His Cys Asp Val Cys Thr Ser Gly Tyr Tyr Gly Lys Val Thr
1430                1435                1440

Gly Ser Ala Ser Asp Cys Ala Leu Cys Ala Cys Pro His Ser Pro
1445                1450                1455

Pro Ala Ser Phe Ser Pro Thr Cys Val Leu Glu Gly Asp His Asp
1460                1465                1470

Phe Arg Cys Asp Ala Cys Leu Leu Gly Tyr Glu Gly Lys His Cys
1475                1480                1485

Glu Arg Cys Ser Ser Ser Tyr Tyr Gly Asn Pro Gln Thr Pro Gly
1490                1495                1500

Gly Ser Cys Gln Lys Cys Asp Cys Asn Pro His Gly Ser Val His
1505                1510                1515

Gly Asp Cys Asp Arg Thr Ser Gly Gln Cys Val Cys Arg Leu Gly
1520                1525                1530

Ala Ser Gly Leu Arg Cys Asp Glu Cys Glu Pro Arg His Ile Leu
1535                1540                1545

Met Glu Thr Asp Cys Val Ser Cys Asp Asp Glu Cys Val Gly Val
1550                1555                1560

Leu Leu Asn Asp Leu Asp Glu Ile Gly Asp Ala Val Leu Ser Leu
1565                1570                1575

Asn Leu Thr Gly Ile Ile Pro Val Pro Tyr Gly Ile Leu Ser Asn
1580                1585                1590

Leu Glu Asn Thr Thr Lys Tyr Leu Gln Glu Ser Leu Leu Lys Glu
1595                1600                1605

Asn Met Gln Lys Asp Leu Gly Lys Ile Lys Leu Glu Gly Val Ala
1610                1615                1620

Glu Glu Thr Asp Asn Leu Gln Lys Lys Leu Thr Arg Met Leu Ala
1625                1630                1635

Ser Thr Gln Lys Val Asn Arg Ala Thr Glu Arg Ile Phe Lys Glu
1640                1645                1650

Ser Gln Asp Leu Ala Ile Ala Ile Glu Arg Leu Gln Met Ser Ile
1655                1660                1665

Thr Glu Ile Met Glu Lys Thr Thr Leu Asn Gln Thr Leu Asp Glu
1670                1675                1680

Asp Phe Leu Leu Pro Asn Ser Thr Leu Gln Asn Met Gln Gln Asn
1685                1690                1695
```

Gly Thr Ser Leu Leu Glu Ile Met Gln Ile Arg Asp Phe Thr Gln
1700                1705                1710

Leu His Gln Asn Ala Thr Leu Glu Leu Lys Ala Ala Glu Asp Leu
1715                1720                1725

Leu Ser Gln Ile Gln Glu Asn Tyr Gln Lys Pro Leu Glu Glu Leu
1730                1735                1740

Glu Val Leu Lys Glu Ala Ala Ser His Val Leu Ser Lys His Asn
1745                1750                1755

Asn Glu Leu Lys Ala Ala Glu Ala Leu Val Arg Glu Ala Glu Ala
1760                1765                1770

Lys Met Gln Glu Ser Asn His Leu Leu Leu Met Val Asn Ala Asn
1775                1780                1785

Leu Arg Glu Phe Ser Asp Lys Lys Leu His Val Gln Glu Glu Gln
1790                1795                1800

Asn Leu Thr Ser Glu Leu Ile Val Gln Gly Arg Gly Leu Ile Asp
1805                1810                1815

Ala Ala Ala Ala Gln Thr Asp Ala Val Gln Asp Ala Leu Glu His
1820                1825                1830

Leu Glu Asp His Gln Asp Lys Leu Leu Leu Trp Ser Ala Lys Ile
1835                1840                1845

Arg His His Ile Asp Asp Leu Val Met His Met Ser Gln Arg Asn
1850                1855                1860

Ala Val Asp Leu Val Tyr Arg Ala Glu Asp His Ala Ala Glu Phe
1865                1870                1875

Gln Arg Leu Ala Asp Val Leu Tyr Ser Gly Leu Glu Asn Ile Arg
1880                1885                1890

Asn Val Ser Leu Asn Ala Thr Ser Ala Ala Tyr Val His Tyr Asn
1895                1900                1905

Ile Gln Ser Leu Ile Glu Glu Ser Glu Glu Leu Ala Arg Asp Ala
1910                1915                1920

His Arg Thr Val Thr Glu Thr Ser Leu Leu Ser Glu Ser Leu Val
1925                1930                1935

Ser Asn Gly Lys Ala Ala Val Gln Arg Ser Ser Arg Phe Leu Lys
1940                1945                1950

Glu Gly Asn Asn Leu Ser Arg Lys Leu Pro Gly Ile Ala Leu Glu
1955                1960                1965

Leu Ser Glu Leu Arg Asn Lys Thr Asn Arg Phe Gln Glu Asn Ala
1970                1975                1980

Val Glu Ile Thr Arg Gln Thr Asn Glu Ser Leu Leu Ile Leu Arg
1985                1990                1995

Ala Ile Pro Lys Gly Ile Arg Asp Lys Gly Ala Lys Thr Lys Glu
2000                2005                2010

Leu Ala Thr Ser Ala Ser Gln Ser Ala Val Ser Thr Leu Arg Asp
2015                2020                2025

Val Ala Gly Leu Ser Gln Glu Leu Leu Asn Thr Ser Ala Ser Leu
2030                2035                2040

Ser Arg Val Asn Thr Thr Leu Arg Glu Thr His Gln Leu Leu Gln
2045                2050                2055

Asp Ser Thr Met Ala Thr Leu Leu Ala Gly Arg Lys Val Lys Asp
2060                2065                2070

Val Glu Ile Gln Ala Asn Leu Leu Phe Asp Arg Leu Lys Pro Leu
2075                2080                2085

Lys Met Leu Glu Glu Asn Leu Ser Arg Asn Leu Ser Glu Ile Lys

```
                2090                2095                2100
Leu Leu Ile Ser Gln Ala Arg Lys Gln Ala Ala Ser Ile Lys Val
    2105                2110                2115
Ala Val Ser Ala Asp Arg Asp Cys Ile Arg Ala Tyr Gln Pro Gln
    2120                2125                2130
Ile Ser Ser Thr Asn Tyr Asn Thr Leu Thr Leu Asn Val Lys Thr
    2135                2140                2145
Gln Glu Pro Asp Asn Leu Leu Phe Tyr Leu Gly Ser Ser Thr Ala
    2150                2155                2160
Ser Asp Phe Leu Ala Val Glu Met Arg Arg Gly Arg Val Ala Phe
    2165                2170                2175
Leu Trp Asp Leu Gly Ser Gly Ser Thr Arg Leu Glu Phe Pro Asp
    2180                2185                2190
Phe Pro Ile Asp Asp Asn Arg Trp His Ser Ile His Val Ala Arg
    2195                2200                2205
Phe Gly Asn Ile Gly Ser Leu Ser Val Lys Glu Met Ser Ser Asn
    2210                2215                2220
Gln Lys Ser Pro Thr Lys Thr Ser Lys Ser Pro Gly Thr Ala Asn
    2225                2230                2235
Val Leu Asp Val Asn Asn Ser Thr Leu Met Phe Val Gly Gly Leu
    2240                2245                2250
Gly Gly Gln Ile Lys Lys Ser Pro Ala Val Lys Val Thr His Phe
    2255                2260                2265
Lys Gly Cys Leu Gly Glu Ala Phe Leu Asn Gly Lys Ser Ile Gly
    2270                2275                2280
Leu Trp Asn Tyr Ile Glu Arg Glu Gly Lys Cys Arg Gly Cys Phe
    2285                2290                2295
Gly Ser Ser Gln Asn Glu Asp Pro Ser Phe His Phe Asp Gly Ser
    2300                2305                2310
Gly Tyr Ser Val Val Glu Lys Ser Leu Pro Ala Thr Val Thr Gln
    2315                2320                2325
Ile Ile Met Leu Phe Asn Thr Phe Ser Pro Asn Gly Leu Leu Leu
    2330                2335                2340
Tyr Leu Gly Ser Tyr Gly Thr Lys Asp Phe Leu Ser Ile Glu Leu
    2345                2350                2355
Phe Arg Gly Arg Val Lys Val Met Thr Asp Leu Gly Ser Gly Pro
    2360                2365                2370
Ile Thr Leu Leu Thr Asp Arg Arg Tyr Asn Asn Gly Thr Trp Tyr
    2375                2380                2385
Lys Ile Ala Phe Gln Arg Asn Arg Lys Gln Gly Val Leu Ala Val
    2390                2395                2400
Ile Asp Ala Tyr Asn Thr Ser Asn Lys Glu Thr Lys Gln Gly Glu
    2405                2410                2415
Thr Pro Gly Ala Ser Ser Asp Leu Asn Arg Leu Asp Lys Asp Pro
    2420                2425                2430
Ile Tyr Val Gly Gly Leu Pro Arg Ser Arg Val Val Arg Arg Gly
    2435                2440                2445
Val Thr Thr Lys Ser Phe Val Gly Cys Ile Lys Asn Leu Glu Ile
    2450                2455                2460
Ser Arg Ser Thr Phe Asp Leu Leu Arg Asn Ser Tyr Gly Val Arg
    2465                2470                2475
Lys Gly Cys Leu Leu Glu Pro Ile Arg Ser Val Ser Phe Leu Lys
    2480                2485                2490
```

```
Gly Gly Tyr Ile Glu Leu Pro Pro Lys Ser Leu Ser Pro Glu Ser
    2495                2500                2505

Glu Trp Leu Val Thr Phe Ala Thr Thr Asn Ser Ser Gly Ile Ile
    2510                2515                2520

Leu Ala Ala Leu Gly Gly Asp Val Glu Lys Arg Gly Asp Arg Glu
    2525                2530                2535

Glu Ala His Val Pro Phe Phe Ser Val Met Leu Ile Gly Gly Asn
    2540                2545                2550

Ile Glu Val His Val Asn Pro Gly Asp Gly Thr Gly Leu Arg Lys
    2555                2560                2565

Ala Leu Leu His Ala Pro Thr Gly Thr Cys Ser Asp Gly Gln Ala
    2570                2575                2580

His Ser Ile Ser Leu Val Arg Asn Arg Arg Ile Ile Thr Val Gln
    2585                2590                2595

Leu Asp Glu Asn Asn Pro Val Glu Met Lys Leu Gly Thr Leu Val
    2600                2605                2610

Glu Ser Arg Thr Ile Asn Val Ser Asn Leu Tyr Val Gly Gly Ile
    2615                2620                2625

Pro Glu Gly Glu Gly Thr Ser Leu Leu Thr Met Arg Arg Ser Phe
    2630                2635                2640

His Gly Cys Ile Lys Asn Leu Ile Phe Asn Leu Glu Leu Leu Asp
    2645                2650                2655

Phe Asn Ser Ala Val Gly His Glu Gln Val Asp Leu Asp Thr Cys
    2660                2665                2670

Trp Leu Ser Glu Arg Pro Lys Leu Ala Pro Asp Ala Glu Asp Ser
    2675                2680                2685

Lys Leu Leu Pro Glu Pro Arg Ala Phe Pro Glu Gln Cys Val Val
    2690                2695                2700

Asp Ala Ala Leu Glu Tyr Val Pro Gly Ala His Gln Phe Gly Leu
    2705                2710                2715

Thr Gln Asn Ser His Phe Ile Leu Pro Phe Asn Gln Ser Ala Val
    2720                2725                2730

Arg Lys Lys Leu Ser Val Glu Leu Ser Ile Arg Thr Phe Ala Ser
    2735                2740                2745

Ser Gly Leu Ile Tyr Tyr Met Ala His Gln Asn Gln Ala Asp Tyr
    2750                2755                2760

Ala Val Leu Gln Leu His Gly Gly Arg Leu His Phe Met Phe Asp
    2765                2770                2775

Leu Gly Lys Gly Arg Thr Lys Val Ser His Pro Ala Leu Leu Ser
    2780                2785                2790

Asp Gly Lys Trp His Thr Val Lys Thr Asp Tyr Val Lys Arg Lys
    2795                2800                2805

Gly Phe Ile Thr Val Asp Gly Arg Glu Ser Pro Met Val Thr Val
    2810                2815                2820

Val Gly Asp Gly Thr Met Leu Asp Val Glu Gly Leu Phe Tyr Leu
    2825                2830                2835

Gly Gly Leu Pro Ser Gln Tyr Gln Ala Arg Lys Ile Gly Asn Ile
    2840                2845                2850

Thr His Ser Ile Pro Ala Cys Ile Gly Asp Val Thr Val Asn Ser
    2855                2860                2865

Lys Gln Leu Asp Lys Asp Ser Pro Val Ser Ala Phe Thr Val Asn
    2870                2875                2880
```

-continued

```
Arg Cys Tyr Ala Val Ala Gln Glu Gly Thr Tyr Phe Asp Gly Ser
    2885                2890                2895

Gly Tyr Ala Ala Leu Val Lys Glu Gly Tyr Lys Val Gln Ser Asp
    2900                2905                2910

Val Asn Ile Thr Leu Glu Phe Arg Thr Ser Ser Gln Asn Gly Val
    2915                2920                2925

Leu Leu Gly Ile Ser Thr Ala Lys Val Asp Ala Ile Gly Leu Glu
    2930                2935                2940

Leu Val Asp Gly Lys Val Leu Phe His Val Asn Asn Gly Ala Gly
    2945                2950                2955

Arg Ile Thr Ala Ala Tyr Glu Pro Lys Thr Ala Thr Val Leu Cys
    2960                2965                2970

Asp Gly Lys Trp His Thr Leu Gln Ala Asn Lys Ser Lys His Arg
    2975                2980                2985

Ile Thr Leu Ile Val Asp Gly Asn Ala Val Gly Ala Glu Ser Pro
    2990                2995                3000

His Thr Gln Ser Thr Ser Val Asp Thr Asn Asn Pro Ile Tyr Val
    3005                3010                3015

Gly Gly Tyr Pro Ala Gly Val Lys Gln Lys Cys Leu Arg Ser Gln
    3020                3025                3030

Thr Ser Phe Arg Gly Cys Leu Arg Lys Leu Ala Leu Ile Lys Ser
    3035                3040                3045

Pro Gln Val Gln Ser Phe Asp Phe Ser Arg Ala Phe Glu Leu His
    3050                3055                3060

Gly Val Phe Leu His Ser Cys Pro Gly Thr Glu Ser
    3065                3070                3075

<210> SEQ ID NO 60
<211> LENGTH: 3695
<212> TYPE: PRT
<213> ORGANISM: Homo sapiens

<400> SEQUENCE: 60

Met Ala Lys Arg Leu Cys Ala Gly Ser Ala Leu Cys Val Arg Gly Pro
1               5                   10                  15

Arg Gly Pro Ala Pro Leu Leu Val Gly Leu Ala Leu Leu Gly Ala
                20                  25                  30

Ala Arg Ala Arg Glu Glu Ala Gly Gly Phe Ser Leu His Pro Pro
            35                  40                  45

Tyr Phe Asn Leu Ala Glu Gly Ala Arg Ile Ala Ala Ser Ala Thr Cys
    50                  55                  60

Gly Glu Glu Ala Pro Ala Arg Gly Ser Pro Arg Pro Thr Glu Asp Leu
65              70                  75                  80

Tyr Cys Lys Leu Val Gly Gly Pro Val Ala Gly Asp Pro Asn Gln
                85                  90                  95

Thr Ile Arg Gly Gln Tyr Cys Asp Ile Cys Thr Ala Ala Asn Ser Asn
            100                 105                 110

Lys Ala His Pro Ala Ser Asn Ala Ile Asp Gly Thr Glu Arg Trp Trp
        115                 120                 125

Gln Ser Pro Pro Leu Ser Arg Gly Leu Glu Tyr Asn Glu Val Asn Val
    130                 135                 140

Thr Leu Asp Leu Gly Gln Val Phe His Val Ala Tyr Val Leu Ile Lys
145                 150                 155                 160

Phe Ala Asn Ser Pro Arg Pro Asp Leu Trp Val Leu Glu Arg Ser Met
                165                 170                 175
```

-continued

```
Asp Phe Gly Arg Thr Tyr Gln Pro Trp Gln Phe Ala Ser Ser Lys
            180                 185                 190

Arg Asp Cys Leu Glu Arg Phe Gly Pro Gln Thr Leu Glu Arg Ile Thr
        195                 200                 205

Arg Asp Asp Ala Ala Ile Cys Thr Thr Glu Tyr Ser Arg Ile Val Pro
    210                 215                 220

Leu Glu Asn Gly Glu Ile Val Val Ser Leu Val Asn Gly Arg Pro Gly
225                 230                 235                 240

Ala Met Asn Phe Ser Tyr Ser Pro Leu Leu Arg Glu Phe Thr Lys Ala
                245                 250                 255

Thr Asn Val Arg Leu Arg Phe Leu Arg Thr Asn Thr Leu Leu Gly His
            260                 265                 270

Leu Met Gly Lys Ala Leu Arg Asp Pro Thr Val Thr Arg Arg Tyr Tyr
        275                 280                 285

Tyr Ser Ile Lys Asp Ile Ser Ile Gly Gly Arg Cys Val Cys His Gly
    290                 295                 300

His Ala Asp Ala Cys Asp Ala Lys Asp Pro Thr Asp Pro Phe Arg Leu
305                 310                 315                 320

Gln Cys Thr Cys Gln His Asn Thr Cys Gly Gly Thr Cys Asp Arg Cys
                325                 330                 335

Cys Pro Gly Phe Asn Gln Gln Pro Trp Lys Pro Ala Thr Ala Asn Ser
            340                 345                 350

Ala Asn Glu Cys Gln Ser Cys Asn Cys Tyr Gly His Ala Thr Asp Cys
        355                 360                 365

Tyr Tyr Asp Pro Glu Val Asp Arg Arg Ala Ser Gln Ser Leu Asp
    370                 375                 380

Gly Thr Tyr Gln Gly Gly Val Cys Ile Asp Cys Gln His His Thr
385                 390                 395                 400

Thr Gly Val Asn Cys Glu Arg Cys Leu Pro Gly Phe Tyr Arg Ser Pro
                405                 410                 415

Asn His Pro Leu Asp Ser Pro His Val Cys Arg Arg Cys Asn Cys Glu
            420                 425                 430

Ser Asp Phe Thr Asp Gly Thr Cys Glu Asp Leu Thr Gly Arg Cys Tyr
        435                 440                 445

Cys Arg Pro Asn Phe Ser Gly Glu Arg Cys Asp Val Cys Ala Glu Gly
    450                 455                 460

Phe Thr Gly Phe Pro Ser Cys Tyr Pro Thr Pro Ser Ser Asn Asp
465                 470                 475                 480

Thr Arg Glu Gln Val Leu Pro Ala Gly Gln Ile Val Asn Cys Asp Cys
                485                 490                 495

Ser Ala Ala Gly Thr Gln Gly Asn Ala Cys Arg Lys Asp Pro Arg Val
            500                 505                 510

Gly Arg Cys Leu Cys Lys Pro Asn Phe Gln Gly Thr His Cys Glu Leu
        515                 520                 525

Cys Ala Pro Gly Phe Tyr Gly Pro Gly Cys Gln Pro Cys Gln Cys Ser
    530                 535                 540

Ser Pro Gly Val Ala Asp Asp Arg Cys Asp Pro Asp Thr Gly Gln Cys
545                 550                 555                 560

Arg Cys Arg Val Gly Phe Glu Gly Ala Thr Cys Asp Arg Cys Ala Pro
                565                 570                 575

Gly Tyr Phe His Phe Pro Leu Cys Gln Leu Cys Gly Cys Ser Pro Ala
            580                 585                 590
```

```
Gly Thr Leu Pro Glu Gly Cys Asp Glu Ala Gly Arg Cys Leu Cys Gln
            595                 600                 605

Pro Glu Phe Ala Gly Pro His Cys Asp Arg Cys Arg Pro Gly Tyr His
        610                 615                 620

Gly Phe Pro Asn Cys Gln Ala Cys Thr Cys Asp Pro Arg Gly Ala Leu
625                 630                 635                 640

Asp Gln Leu Cys Gly Ala Gly Leu Cys Arg Cys Arg Pro Gly Tyr
                645                 650                 655

Thr Gly Thr Ala Cys Gln Glu Cys Ser Pro Gly Phe His Gly Phe Pro
            660                 665                 670

Ser Cys Val Pro Cys His Cys Ser Ala Glu Gly Ser Leu His Ala Ala
        675                 680                 685

Cys Asp Pro Arg Ser Gly Gln Cys Ser Cys Arg Pro Arg Val Thr Gly
        690                 695                 700

Leu Arg Cys Asp Thr Cys Val Pro Gly Ala Tyr Asn Phe Pro Tyr Cys
705                 710                 715                 720

Glu Ala Gly Ser Cys His Pro Ala Gly Leu Ala Pro Val Asp Pro Ala
                725                 730                 735

Leu Pro Glu Ala Gln Val Pro Cys Met Cys Arg Ala His Val Glu Gly
            740                 745                 750

Pro Ser Cys Asp Arg Cys Lys Pro Gly Phe Trp Gly Leu Ser Pro Ser
        755                 760                 765

Asn Pro Glu Gly Cys Thr Arg Cys Ser Cys Asp Leu Arg Gly Thr Leu
        770                 775                 780

Gly Gly Val Ala Glu Cys Gln Pro Gly Thr Gly Gln Cys Phe Cys Lys
785                 790                 795                 800

Pro His Val Cys Gly Gln Ala Cys Ala Ser Cys Lys Asp Gly Phe Phe
                805                 810                 815

Gly Leu Asp Gln Ala Asp Tyr Phe Gly Cys Arg Ser Cys Arg Cys Asp
                820                 825                 830

Ile Gly Gly Ala Leu Gly Gln Ser Cys Glu Pro Arg Thr Gly Val Cys
            835                 840                 845

Arg Cys Arg Pro Asn Thr Gln Gly Pro Thr Cys Ser Glu Pro Ala Arg
850                 855                 860

Asp His Tyr Leu Pro Asp Leu His His Leu Arg Leu Glu Leu Glu Glu
865                 870                 875                 880

Ala Ala Thr Pro Glu Gly His Ala Val Arg Phe Gly Phe Asn Pro Leu
                885                 890                 895

Glu Phe Glu Asn Phe Ser Trp Arg Gly Tyr Ala Gln Met Ala Pro Val
            900                 905                 910

Gln Pro Arg Ile Val Ala Arg Leu Asn Leu Thr Ser Pro Asp Leu Phe
        915                 920                 925

Trp Leu Val Phe Arg Tyr Val Asn Arg Gly Ala Met Ser Val Ser Gly
930                 935                 940

Arg Val Ser Val Arg Glu Glu Gly Arg Ser Ala Thr Cys Ala Asn Cys
945                 950                 955                 960

Thr Ala Gln Ser Gln Pro Val Ala Phe Pro Pro Ser Thr Glu Pro Ala
                965                 970                 975

Phe Ile Thr Val Pro Gln Arg Gly Phe Gly Glu Pro Phe Val Leu Asn
            980                 985                 990

Pro Gly Thr Trp Ala Leu Arg Val Glu Ala Glu Gly Val Leu Leu Asp
        995                 1000                1005

Tyr Val  Val Leu Leu Pro Ser  Ala Tyr Tyr Glu Ala  Ala Leu Leu
```

-continued

```
                1010                1015                1020
Gln Leu Arg Val Thr Glu Ala Cys Thr Tyr Arg Pro Ser Ala Gln
        1025                1030                1035
Gln Ser Gly Asp Asn Cys Leu Leu Tyr Thr His Leu Pro Leu Asp
        1040                1045                1050
Gly Phe Pro Ser Ala Ala Gly Leu Glu Ala Leu Cys Arg Gln Asp
        1055                1060                1065
Asn Ser Leu Pro Arg Pro Cys Pro Thr Glu Gln Leu Ser Pro Ser
        1070                1075                1080
His Pro Pro Leu Ile Thr Cys Thr Gly Ser Asp Val Asp Val Gln
        1085                1090                1095
Leu Gln Val Ala Val Pro Gln Pro Gly Arg Tyr Ala Leu Val Val
        1100                1105                1110
Glu Tyr Ala Asn Glu Asp Ala Arg Gln Glu Val Gly Val Ala Val
        1115                1120                1125
His Thr Pro Gln Arg Ala Pro Gln Gln Gly Leu Leu Ser Leu His
        1130                1135                1140
Pro Cys Leu Tyr Ser Thr Leu Cys Arg Gly Thr Ala Arg Asp Thr
        1145                1150                1155
Gln Asp His Leu Ala Val Phe His Leu Asp Ser Glu Ala Ser Val
        1160                1165                1170
Arg Leu Thr Ala Glu Gln Ala Arg Phe Phe Leu His Gly Val Thr
        1175                1180                1185
Leu Val Pro Ile Glu Glu Phe Ser Pro Glu Phe Val Glu Pro Arg
        1190                1195                1200
Val Ser Cys Ile Ser Ser His Gly Ala Phe Gly Pro Asn Ser Ala
        1205                1210                1215
Ala Cys Leu Pro Ser Arg Phe Pro Lys Pro Pro Gln Pro Ile Ile
        1220                1225                1230
Leu Arg Asp Cys Gln Val Ile Pro Leu Pro Pro Gly Leu Pro Leu
        1235                1240                1245
Thr His Ala Gln Asp Leu Thr Pro Ala Met Ser Pro Ala Gly Pro
        1250                1255                1260
Arg Pro Arg Pro Pro Thr Ala Val Asp Pro Asp Ala Glu Pro Thr
        1265                1270                1275
Leu Leu Arg Glu Pro Gln Ala Thr Val Val Phe Thr Thr His Val
        1280                1285                1290
Pro Thr Leu Gly Arg Tyr Ala Phe Leu Leu His Gly Tyr Gln Pro
        1295                1300                1305
Ala His Pro Thr Phe Pro Val Glu Val Leu Ile Asn Ala Gly Arg
        1310                1315                1320
Val Trp Gln Gly His Ala Asn Ala Ser Phe Cys Pro His Gly Tyr
        1325                1330                1335
Gly Cys Arg Thr Leu Val Val Cys Glu Gly Gln Ala Leu Leu Asp
        1340                1345                1350
Val Thr His Ser Glu Leu Thr Val Thr Val Arg Val Pro Lys Gly
        1355                1360                1365
Arg Trp Leu Trp Leu Asp Tyr Val Leu Val Val Pro Glu Asn Val
        1370                1375                1380
Tyr Ser Phe Gly Tyr Leu Arg Glu Glu Pro Leu Asp Lys Ser Tyr
        1385                1390                1395
Asp Phe Ile Ser His Cys Ala Ala Gln Gly Tyr His Ile Ser Pro
        1400                1405                1410
```

```
Ser Ser Ser Ser Leu Phe Cys Arg Asn Ala Ala Ala Ser Leu Ser
    1415            1420                1425

Leu Phe Tyr Asn Asn Gly Ala Arg Pro Cys Gly Cys His Glu Val
    1430            1435                1440

Gly Ala Thr Gly Pro Thr Cys Glu Pro Phe Gly Gly Gln Cys Pro
    1445            1450                1455

Cys His Ala His Val Ile Gly Arg Asp Cys Ser Arg Cys Ala Thr
    1460            1465                1470

Gly Tyr Trp Gly Phe Pro Asn Cys Arg Pro Cys Asp Cys Gly Ala
    1475            1480                1485

Arg Leu Cys Asp Glu Leu Thr Gly Gln Cys Ile Cys Pro Pro Arg
    1490            1495                1500

Thr Ile Pro Pro Asp Cys Leu Leu Cys Gln Pro Gln Thr Phe Gly
    1505            1510                1515

Cys His Pro Leu Val Gly Cys Glu Glu Cys Asn Cys Ser Gly Pro
    1520            1525                1530

Gly Ile Gln Glu Leu Thr Asp Pro Thr Cys Asp Thr Asp Ser Gly
    1535            1540                1545

Gln Cys Lys Cys Arg Pro Asn Val Thr Gly Arg Arg Cys Asp Thr
    1550            1555                1560

Cys Ser Pro Gly Phe His Gly Tyr Pro Arg Cys Arg Pro Cys Asp
    1565            1570                1575

Cys His Glu Ala Gly Thr Ala Pro Gly Val Cys Asp Pro Leu Thr
    1580            1585                1590

Gly Gln Cys Tyr Cys Lys Glu Asn Val Gln Gly Pro Lys Cys Asp
    1595            1600                1605

Gln Cys Ser Leu Gly Thr Phe Ser Leu Asp Ala Ala Asn Pro Lys
    1610            1615                1620

Gly Cys Thr Arg Cys Phe Cys Phe Gly Ala Thr Glu Arg Cys Arg
    1625            1630                1635

Ser Ser Ser Tyr Thr Arg Gln Glu Phe Val Asp Met Glu Gly Trp
    1640            1645                1650

Val Leu Leu Ser Thr Asp Arg Gln Val Pro His Glu Arg Gln
    1655            1660                1665

Pro Gly Thr Glu Met Leu Arg Ala Asp Leu Arg His Val Pro Glu
    1670            1675                1680

Ala Val Pro Glu Ala Phe Pro Glu Leu Tyr Trp Gln Ala Pro Pro
    1685            1690                1695

Ser Tyr Leu Gly Asp Arg Val Ser Ser Tyr Gly Gly Thr Leu Arg
    1700            1705                1710

Tyr Glu Leu His Ser Glu Thr Gln Arg Gly Asp Val Phe Val Pro
    1715            1720                1725

Met Glu Ser Arg Pro Asp Val Val Leu Gln Gly Asn Gln Met Ser
    1730            1735                1740

Ile Thr Phe Leu Glu Pro Ala Tyr Pro Thr Pro Gly His Val His
    1745            1750                1755

Arg Gly Gln Leu Gln Leu Val Glu Gly Asn Phe Arg His Thr Glu
    1760            1765                1770

Thr Arg Asn Thr Val Ser Arg Glu Glu Leu Met Met Val Leu Ala
    1775            1780                1785

Ser Leu Glu Gln Leu Gln Ile Arg Ala Leu Phe Ser Gln Ile Ser
    1790            1795                1800
```

-continued

Ser Ala Val Phe Leu Arg Arg Val Ala Leu Glu Val Ala Ser Pro
1805                1810                1815

Ala Gly Gln Gly Ala Leu Ala Ser Asn Val Glu Leu Cys Leu Cys
1820                1825                1830

Pro Ala Ser Tyr Arg Gly Asp Ser Cys Gln Glu Cys Ala Pro Gly
1835                1840                1845

Phe Tyr Arg Asp Val Lys Gly Leu Phe Leu Gly Arg Cys Val Pro
1850                1855                1860

Cys Gln Cys His Gly His Ser Asp Arg Cys Leu Pro Gly Ser Gly
1865                1870                1875

Val Cys Val Asp Cys Gln His Asn Thr Glu Gly Ala His Cys Glu
1880                1885                1890

Arg Cys Gln Ala Gly Phe Val Ser Ser Arg Asp Asp Pro Ser Ala
1895                1900                1905

Pro Cys Val Ser Cys Pro Cys Pro Leu Ser Val Pro Ser Asn Asn
1910                1915                1920

Phe Ala Glu Gly Cys Val Leu Arg Gly Gly Arg Thr Gln Cys Leu
1925                1930                1935

Cys Lys Pro Gly Tyr Ala Gly Ala Ser Cys Glu Arg Cys Ala Pro
1940                1945                1950

Gly Phe Phe Gly Asn Pro Leu Val Leu Gly Ser Ser Cys Gln Pro
1955                1960                1965

Cys Asp Cys Ser Gly Asn Gly Asp Pro Asn Leu Leu Phe Ser Asp
1970                1975                1980

Cys Asp Pro Leu Thr Gly Ala Cys Arg Gly Cys Leu Arg His Thr
1985                1990                1995

Thr Gly Pro Arg Cys Glu Ile Cys Ala Pro Gly Phe Tyr Gly Asn
2000                2005                2010

Ala Leu Leu Pro Gly Asn Cys Thr Arg Cys Asp Cys Thr Pro Cys
2015                2020                2025

Gly Thr Glu Ala Cys Asp Pro His Ser Gly His Cys Leu Cys Lys
2030                2035                2040

Ala Gly Val Thr Gly Arg Arg Cys Asp Arg Cys Gln Glu Gly His
2045                2050                2055

Phe Gly Phe Asp Gly Cys Gly Gly Cys Arg Pro Cys Ala Cys Gly
2060                2065                2070

Pro Ala Ala Glu Gly Ser Glu Cys His Pro Gln Ser Gly Gln Cys
2075                2080                2085

His Cys Arg Pro Gly Thr Met Gly Pro Gln Cys Arg Glu Cys Ala
2090                2095                2100

Pro Gly Tyr Trp Gly Leu Pro Glu Gln Gly Cys Arg Arg Cys Gln
2105                2110                2115

Cys Pro Gly Gly Arg Cys Asp Pro His Thr Gly Arg Cys Asn Cys
2120                2125                2130

Pro Pro Gly Leu Ser Gly Glu Arg Cys Asp Thr Cys Ser Gln Gln
2135                2140                2145

His Gln Val Pro Val Pro Gly Gly Pro Val Gly His Ser Ile His
2150                2155                2160

Cys Glu Val Cys Asp His Cys Val Val Leu Leu Leu Asp Asp Leu
2165                2170                2175

Glu Arg Ala Gly Ala Leu Leu Pro Ala Ile His Glu Gln Leu Arg
2180                2185                2190

Gly Ile Asn Ala Ser Ser Met Ala Trp Ala Arg Leu His Arg Leu

```
            2195                2200                2205

Asn Ala Ser Ile Ala Asp Leu Gln Ser Gln Leu Arg Ser Pro Leu
            2210                2215                2220

Gly Pro Arg His Glu Thr Ala Gln Gln Leu Glu Val Leu Glu Gln
            2225                2230                2235

Gln Ser Thr Ser Leu Gly Gln Asp Ala Arg Arg Leu Gly Gly Gln
            2240                2245                2250

Ala Val Gly Thr Arg Asp Gln Ala Ser Gln Leu Leu Ala Gly Thr
            2255                2260                2265

Glu Ala Thr Leu Gly His Ala Lys Thr Leu Leu Ala Ala Ile Arg
            2270                2275                2280

Ala Val Asp Arg Thr Leu Ser Glu Leu Met Ser Gln Thr Gly His
            2285                2290                2295

Leu Gly Leu Ala Asn Ala Ser Ala Pro Ser Gly Glu Gln Leu Leu
            2300                2305                2310

Arg Thr Leu Ala Glu Val Glu Arg Leu Leu Trp Glu Met Arg Ala
            2315                2320                2325

Arg Asp Leu Gly Ala Pro Gln Ala Ala Glu Ala Glu Leu Ala
            2330                2335                2340

Ala Ala Gln Arg Leu Leu Ala Arg Val Gln Glu Gln Leu Ser Ser
            2345                2350                2355

Leu Trp Glu Glu Asn Gln Ala Leu Ala Thr Gln Thr Arg Asp Arg
            2360                2365                2370

Leu Ala Gln His Glu Ala Gly Leu Met Asp Leu Arg Glu Ala Leu
            2375                2380                2385

Asn Arg Ala Val Asp Ala Thr Arg Glu Ala Gln Glu Leu Asn Ser
            2390                2395                2400

Arg Asn Gln Glu Arg Leu Glu Glu Ala Leu Gln Arg Lys Gln Glu
            2405                2410                2415

Leu Ser Arg Asp Asn Ala Thr Leu Gln Ala Thr Leu His Ala Ala
            2420                2425                2430

Arg Asp Thr Leu Ala Ser Val Phe Arg Leu Leu His Ser Leu Asp
            2435                2440                2445

Gln Ala Lys Glu Glu Leu Glu Arg Leu Ala Ala Ser Leu Asp Gly
            2450                2455                2460

Ala Arg Thr Pro Leu Leu Gln Arg Met Gln Thr Phe Ser Pro Ala
            2465                2470                2475

Gly Ser Lys Leu Arg Leu Val Glu Ala Ala Glu Ala His Ala Gln
            2480                2485                2490

Gln Leu Gly Gln Leu Ala Leu Asn Leu Ser Ser Ile Ile Leu Asp
            2495                2500                2505

Val Asn Gln Asp Arg Leu Thr Gln Arg Ala Ile Glu Ala Ser Asn
            2510                2515                2520

Ala Tyr Ser Arg Ile Leu Gln Ala Val Gln Ala Ala Glu Asp Ala
            2525                2530                2535

Ala Gly Gln Ala Leu Gln Gln Ala Asp His Thr Trp Ala Thr Val
            2540                2545                2550

Val Arg Gln Gly Leu Val Asp Arg Ala Gln Gln Leu Leu Ala Asn
            2555                2560                2565

Ser Thr Ala Leu Glu Glu Ala Met Leu Gln Glu Gln Gln Arg Leu
            2570                2575                2580

Gly Leu Val Trp Ala Ala Leu Gln Gly Ala Arg Thr Gln Leu Arg
            2585                2590                2595
```

```
Asp Val Arg Ala Lys Lys Asp Gln Leu Glu Ala His Ile Gln Ala
    2600            2605                2610
Ala Gln Ala Met Leu Ala Met Asp Thr Asp Glu Thr Ser Lys Lys
    2615            2620                2625
Ile Ala His Ala Lys Ala Val Ala Ala Glu Ala Gln Asp Thr Ala
    2630            2635                2640
Thr Arg Val Gln Ser Gln Leu Gln Ala Met Gln Glu Asn Val Glu
    2645            2650                2655
Arg Trp Gln Gly Gln Tyr Glu Gly Leu Arg Gly Gln Asp Leu Gly
    2660            2665                2670
Gln Ala Val Leu Asp Ala Gly His Ser Val Ser Thr Leu Glu Lys
    2675            2680                2685
Thr Leu Pro Gln Leu Leu Ala Lys Leu Ser Ile Leu Glu Asn Arg
    2690            2695                2700
Gly Val His Asn Ala Ser Leu Ala Leu Ser Ala Ser Ile Gly Arg
    2705            2710                2715
Val Arg Glu Leu Ile Ala Gln Ala Arg Gly Ala Ala Ser Lys Val
    2720            2725                2730
Lys Val Pro Met Lys Phe Asn Gly Arg Ser Gly Val Gln Leu Arg
    2735            2740                2745
Thr Pro Arg Asp Leu Ala Asp Leu Ala Ala Tyr Thr Ala Leu Lys
    2750            2755                2760
Phe Tyr Leu Gln Gly Pro Glu Pro Glu Pro Gly Gln Gly Thr Glu
    2765            2770                2775
Asp Arg Phe Val Met Tyr Met Gly Ser Arg Gln Ala Thr Gly Asp
    2780            2785                2790
Tyr Met Gly Val Ser Leu Arg Asp Lys Lys Val His Trp Val Tyr
    2795            2800                2805
Gln Leu Gly Glu Ala Gly Pro Ala Val Leu Ser Ile Asp Glu Asp
    2810            2815                2820
Ile Gly Glu Gln Phe Ala Ala Val Ser Leu Asp Arg Thr Leu Gln
    2825            2830                2835
Phe Gly His Met Ser Val Thr Val Glu Arg Gln Met Ile Gln Glu
    2840            2845                2850
Thr Lys Gly Asp Thr Val Ala Pro Gly Ala Glu Gly Leu Leu Asn
    2855            2860                2865
Leu Arg Pro Asp Asp Phe Val Phe Tyr Val Gly Gly Tyr Pro Ser
    2870            2875                2880
Thr Phe Thr Pro Pro Pro Leu Leu Arg Phe Pro Gly Tyr Arg Gly
    2885            2890                2895
Cys Ile Glu Met Asp Thr Leu Asn Glu Glu Val Val Ser Leu Tyr
    2900            2905                2910
Asn Phe Glu Arg Thr Phe Gln Leu Asp Thr Ala Val Asp Arg Pro
    2915            2920                2925
Cys Ala Arg Ser Lys Ser Thr Gly Asp Pro Trp Leu Thr Asp Gly
    2930            2935                2940
Ser Tyr Leu Asp Gly Thr Gly Phe Ala Arg Ile Ser Phe Asp Ser
    2945            2950                2955
Gln Ile Ser Thr Thr Lys Arg Phe Glu Gln Glu Leu Arg Leu Val
    2960            2965                2970
Ser Tyr Ser Gly Val Leu Phe Phe Leu Lys Gln Gln Ser Gln Phe
    2975            2980                2985
```

```
Leu Cys Leu Ala Val Gln Glu Gly Ser Leu Val Leu Leu Tyr Asp
2990               2995               3000

Phe Gly Ala Gly Leu Lys Lys Ala Val Pro Leu Gln Pro Pro Pro
3005               3010               3015

Pro Leu Thr Ser Ala Ser Lys Ala Ile Gln Val Phe Leu Leu Gly
3020               3025               3030

Gly Ser Arg Lys Arg Val Leu Val Arg Val Glu Arg Ala Thr Val
3035               3040               3045

Tyr Ser Val Glu Gln Asp Asn Asp Leu Glu Leu Ala Asp Ala Tyr
3050               3055               3060

Tyr Leu Gly Gly Val Pro Pro Asp Gln Leu Pro Pro Ser Leu Arg
3065               3070               3075

Arg Leu Phe Pro Thr Gly Gly Ser Val Arg Gly Cys Val Lys Gly
3080               3085               3090

Ile Lys Ala Leu Gly Lys Tyr Val Asp Leu Lys Arg Leu Asn Thr
3095               3100               3105

Thr Gly Val Ser Ala Gly Cys Thr Ala Asp Leu Leu Val Gly Arg
3110               3115               3120

Ala Met Thr Phe His Gly His Gly Phe Leu Arg Leu Ala Leu Ser
3125               3130               3135

Asn Val Ala Pro Leu Thr Gly Asn Val Tyr Ser Gly Phe Gly Phe
3140               3145               3150

His Ser Ala Gln Asp Ser Ala Leu Leu Tyr Tyr Arg Ala Ser Pro
3155               3160               3165

Asp Gly Leu Cys Gln Val Ser Leu Gln Gln Gly Arg Val Ser Leu
3170               3175               3180

Gln Leu Leu Arg Thr Glu Val Lys Thr Gln Ala Gly Phe Ala Asp
3185               3190               3195

Gly Ala Pro His Tyr Val Ala Phe Tyr Ser Asn Ala Thr Gly Val
3200               3205               3210

Trp Leu Tyr Val Asp Asp Gln Leu Gln Gln Met Lys Pro His Arg
3215               3220               3225

Gly Pro Pro Pro Glu Leu Gln Pro Gln Pro Glu Gly Pro Pro Arg
3230               3235               3240

Leu Leu Leu Gly Gly Leu Pro Glu Ser Gly Thr Ile Tyr Asn Phe
3245               3250               3255

Ser Gly Cys Ile Ser Asn Val Phe Val Gln Arg Leu Leu Gly Pro
3260               3265               3270

Gln Arg Val Phe Asp Leu Gln Gln Asn Leu Gly Ser Val Asn Val
3275               3280               3285

Ser Thr Gly Cys Ala Pro Ala Leu Gln Ala Gln Thr Pro Gly Leu
3290               3295               3300

Gly Pro Arg Gly Leu Gln Ala Thr Ala Arg Lys Ala Ser Arg Arg
3305               3310               3315

Ser Arg Gln Pro Ala Arg His Pro Ala Cys Met Leu Pro Pro His
3320               3325               3330

Leu Arg Thr Thr Arg Asp Ser Tyr Gln Phe Gly Gly Ser Leu Ser
3335               3340               3345

Ser His Leu Glu Phe Val Gly Ile Leu Ala Arg His Arg Asn Trp
3350               3355               3360

Pro Ser Leu Ser Met His Val Leu Pro Arg Ser Ser Arg Gly Leu
3365               3370               3375

Leu Leu Phe Thr Ala Arg Leu Arg Pro Gly Ser Pro Ser Leu Ala
```

```
                  3380              3385              3390
Leu Phe Leu Ser Asn Gly His Phe Val Ala Gln Met Glu Gly Leu
    3395              3400              3405

Gly Thr Arg Leu Arg Ala Gln Ser Arg Gln Ser Arg Pro Gly
    3410              3415              3420

Arg Trp His Lys Val Ser Val Arg Trp Glu Lys Asn Arg Ile Leu
    3425              3430              3435

Leu Val Thr Asp Gly Ala Arg Ala Trp Ser Gln Glu Gly Pro His
    3440              3445              3450

Arg Gln His Gln Gly Ala Glu His Pro Gln Pro His Thr Leu Phe
    3455              3460              3465

Val Gly Gly Leu Pro Ala Ser Ser His Ser Ser Lys Leu Pro Val
    3470              3475              3480

Thr Val Gly Phe Ser Gly Cys Val Lys Arg Leu Arg Leu His Gly
    3485              3490              3495

Arg Pro Leu Gly Ala Pro Thr Arg Met Ala Gly Val Thr Pro Cys
    3500              3505              3510

Ile Leu Gly Pro Leu Glu Ala Gly Leu Phe Phe Pro Gly Ser Gly
    3515              3520              3525

Gly Val Ile Thr Leu Asp Leu Pro Gly Ala Thr Leu Pro Asp Val
    3530              3535              3540

Gly Leu Glu Leu Glu Val Arg Pro Leu Ala Val Thr Gly Leu Ile
    3545              3550              3555

Phe His Leu Gly Gln Ala Arg Thr Pro Pro Tyr Leu Gln Leu Gln
    3560              3565              3570

Val Thr Glu Lys Gln Val Leu Leu Arg Ala Asp Asp Gly Ala Gly
    3575              3580              3585

Glu Phe Ser Thr Ser Val Thr Arg Pro Ser Val Leu Cys Asp Gly
    3590              3595              3600

Gln Trp His Arg Leu Ala Val Met Lys Ser Gly Asn Val Leu Arg
    3605              3610              3615

Leu Glu Val Asp Ala Gln Ser Asn His Thr Val Gly Pro Leu Leu
    3620              3625              3630

Ala Ala Ala Ala Gly Ala Pro Ala Pro Leu Tyr Leu Gly Gly Leu
    3635              3640              3645

Pro Glu Pro Met Ala Val Gln Pro Trp Pro Pro Ala Tyr Cys Gly
    3650              3655              3660

Cys Met Arg Arg Leu Ala Val Asn Arg Ser Pro Val Ala Met Thr
    3665              3670              3675

Arg Ser Val Glu Val His Gly Ala Val Gly Ala Ser Gly Cys Pro
    3680              3685              3690

Ala Ala
    3695

<210> SEQ ID NO 61
<211> LENGTH: 1786
<212> TYPE: PRT
<213> ORGANISM: Homo sapiens

<400> SEQUENCE: 61

Met Gly Leu Leu Gln Leu Leu Ala Phe Ser Phe Leu Ala Leu Cys Arg
1               5                   10                  15

Ala Arg Val Arg Ala Gln Glu Pro Glu Phe Ser Tyr Gly Cys Ala Glu
            20                  25                  30
```

-continued

```
Gly Ser Cys Tyr Pro Ala Thr Gly Asp Leu Leu Ile Gly Arg Ala Gln
        35                  40                  45

Lys Leu Ser Val Thr Ser Thr Cys Gly Leu His Lys Pro Glu Pro Tyr
 50                  55                  60

Cys Ile Val Ser His Leu Gln Glu Asp Lys Lys Cys Phe Ile Cys Asn
 65                  70                  75                  80

Ser Gln Asp Pro Tyr His Glu Thr Leu Asn Pro Asp Ser His Leu Ile
                 85                  90                  95

Glu Asn Val Val Thr Thr Phe Ala Pro Asn Arg Leu Lys Ile Trp Trp
                100                 105                 110

Gln Ser Glu Asn Gly Val Glu Asn Val Thr Ile Gln Leu Asp Leu Glu
        115                 120                 125

Ala Glu Phe His Phe Thr His Leu Ile Met Thr Phe Lys Thr Phe Arg
130                 135                 140

Pro Ala Ala Met Leu Ile Glu Arg Ser Ser Asp Phe Gly Lys Thr Trp
145                 150                 155                 160

Gly Val Tyr Arg Tyr Phe Ala Tyr Asp Cys Glu Ala Ser Phe Pro Gly
                165                 170                 175

Ile Ser Thr Gly Pro Met Lys Lys Val Asp Asp Ile Ile Cys Asp Ser
                180                 185                 190

Arg Tyr Ser Asp Ile Glu Pro Ser Thr Glu Gly Glu Val Ile Phe Arg
        195                 200                 205

Ala Leu Asp Pro Ala Phe Lys Ile Glu Asp Pro Tyr Ser Pro Arg Ile
210                 215                 220

Gln Asn Leu Leu Lys Ile Thr Asn Leu Arg Ile Lys Phe Val Lys Leu
225                 230                 235                 240

His Thr Leu Gly Asp Asn Leu Leu Asp Ser Arg Met Glu Ile Arg Glu
                245                 250                 255

Lys Tyr Tyr Tyr Ala Val Tyr Asp Met Val Val Arg Gly Asn Cys Phe
                260                 265                 270

Cys Tyr Gly His Ala Ser Glu Cys Ala Pro Val Asp Gly Phe Asn Glu
        275                 280                 285

Glu Val Glu Gly Met Val His Gly His Cys Met Cys Arg His Asn Thr
290                 295                 300

Lys Gly Leu Asn Cys Glu Leu Cys Met Asp Phe Tyr His Asp Leu Pro
305                 310                 315                 320

Trp Arg Pro Ala Glu Gly Arg Asn Ser Asn Ala Cys Lys Lys Cys Asn
                325                 330                 335

Cys Asn Glu His Ser Ile Ser Cys His Phe Asp Met Ala Val Tyr Leu
                340                 345                 350

Ala Thr Gly Asn Val Ser Gly Val Cys Asp Asp Cys Gln His Asn
        355                 360                 365

Thr Met Gly Arg Asn Cys Glu Gln Cys Lys Pro Phe Tyr Tyr Gln His
370                 375                 380

Pro Glu Arg Asp Ile Arg Asp Pro Asn Phe Cys Glu Arg Cys Thr Cys
385                 390                 395                 400

Asp Pro Ala Gly Ser Gln Asn Glu Gly Ile Cys Asp Ser Tyr Thr Asp
                405                 410                 415

Phe Ser Thr Gly Leu Ile Ala Gly Gln Cys Arg Cys Lys Leu Asn Val
                420                 425                 430

Glu Gly Glu His Cys Asp Val Cys Lys Glu Gly Phe Tyr Asp Leu Ser
        435                 440                 445

Ser Glu Asp Pro Phe Gly Cys Lys Ser Cys Ala Cys Asn Pro Leu Gly
```

```
            450                 455                 460
Thr Ile Pro Gly Gly Asn Pro Cys Asp Ser Glu Thr Gly His Cys Tyr
465                 470                 475                 480

Cys Lys Arg Leu Val Thr Gly Gln His Cys Asp Gln Cys Leu Pro Glu
                485                 490                 495

His Trp Gly Leu Ser Asn Asp Leu Asp Gly Cys Arg Pro Cys Asp Cys
            500                 505                 510

Asp Leu Gly Gly Ala Leu Asn Asn Ser Cys Phe Ala Glu Ser Gly Gln
            515                 520                 525

Cys Ser Cys Arg Pro His Met Ile Gly Arg Gln Cys Asn Glu Val Glu
            530                 535                 540

Pro Gly Tyr Tyr Phe Ala Thr Leu Asp His Tyr Leu Tyr Glu Ala Glu
545                 550                 555                 560

Glu Ala Asn Leu Gly Pro Gly Val Ser Ile Val Glu Arg Gln Tyr Ile
                565                 570                 575

Gln Asp Arg Ile Pro Ser Trp Thr Gly Ala Gly Phe Val Arg Val Pro
            580                 585                 590

Glu Gly Ala Tyr Leu Glu Phe Phe Ile Asp Asn Ile Pro Tyr Ser Met
            595                 600                 605

Glu Tyr Asp Ile Leu Ile Arg Tyr Glu Pro Gln Leu Pro Asp His Trp
            610                 615                 620

Glu Lys Ala Val Ile Thr Val Gln Arg Pro Gly Arg Ile Pro Thr Ser
625                 630                 635                 640

Ser Arg Cys Gly Asn Thr Ile Pro Asp Asp Asn Gln Val Val Ser
                645                 650                 655

Leu Ser Pro Gly Ser Arg Tyr Val Val Leu Pro Arg Pro Val Cys Phe
            660                 665                 670

Glu Lys Gly Thr Asn Tyr Thr Val Arg Leu Glu Leu Pro Gln Tyr Thr
            675                 680                 685

Ser Ser Asp Ser Asp Val Glu Ser Pro Tyr Thr Leu Ile Asp Ser Leu
            690                 695                 700

Val Leu Met Pro Tyr Cys Lys Ser Leu Asp Ile Phe Thr Val Gly Gly
705                 710                 715                 720

Ser Gly Asp Gly Val Val Thr Asn Ser Ala Trp Glu Thr Phe Gln Arg
                725                 730                 735

Tyr Arg Cys Leu Glu Asn Ser Arg Ser Val Val Lys Thr Pro Met Thr
                740                 745                 750

Asp Val Cys Arg Asn Ile Ile Phe Ser Ile Ser Ala Leu Leu His Gln
                755                 760                 765

Thr Gly Leu Ala Cys Glu Cys Asp Pro Gln Gly Ser Leu Ser Ser Val
770                 775                 780

Cys Asp Pro Asn Gly Gln Cys Gln Cys Arg Pro Asn Val Val Gly
785                 790                 795                 800

Arg Thr Cys Asn Arg Cys Ala Pro Gly Thr Phe Gly Phe Gly Pro Ser
                805                 810                 815

Gly Cys Lys Pro Cys Glu Cys His Leu Gln Gly Ser Val Asn Ala Phe
                820                 825                 830

Cys Asn Pro Val Thr Gly Gln Cys His Cys Phe Gln Gly Val Tyr Ala
            835                 840                 845

Arg Gln Cys Asp Arg Cys Leu Pro Gly His Trp Gly Phe Pro Ser Cys
            850                 855                 860

Gln Pro Cys Gln Cys Asn Gly His Ala Asp Asp Cys Asp Pro Val Thr
865                 870                 875                 880
```

-continued

```
Gly Glu Cys Leu Asn Cys Gln Asp Tyr Thr Met Gly His Asn Cys Glu
                885                 890                 895
Arg Cys Leu Ala Gly Tyr Tyr Gly Asp Pro Ile Ile Gly Ser Gly Asp
            900                 905                 910
His Cys Arg Pro Cys Pro Cys Pro Asp Gly Pro Asp Ser Gly Arg Gln
            915                 920                 925
Phe Ala Arg Ser Cys Tyr Gln Asp Pro Val Thr Leu Gln Leu Ala Cys
        930                 935                 940
Val Cys Asp Pro Gly Tyr Ile Gly Ser Arg Cys Asp Cys Ala Ser
945                 950                 955                 960
Gly Tyr Phe Gly Asn Pro Ser Glu Val Gly Gly Ser Cys Gln Pro Cys
                965                 970                 975
Gln Cys His Asn Asn Ile Asp Thr Thr Asp Pro Glu Ala Cys Asp Lys
            980                 985                 990
Glu Thr Gly Arg Cys Leu Lys Cys Leu Tyr His Thr Glu Gly Glu His
            995                 1000                1005
Cys Gln Phe Cys Arg Phe Gly Tyr Tyr Gly Asp Ala Leu Gln Gln
    1010                1015                1020
Asp Cys Arg Lys Cys Val Cys Asn Tyr Leu Gly Thr Val Gln Glu
    1025                1030                1035
His Cys Asn Gly Ser Asp Cys Gln Cys Asp Lys Ala Thr Gly Gln
    1040                1045                1050
Cys Leu Cys Leu Pro Asn Val Ile Gly Gln Asn Cys Asp Arg Cys
    1055                1060                1065
Ala Pro Asn Thr Trp Gln Leu Ala Ser Gly Thr Gly Cys Asp Pro
    1070                1075                1080
Cys Asn Cys Asn Ala Ala His Ser Phe Gly Pro Ser Cys Asn Glu
    1085                1090                1095
Phe Thr Gly Gln Cys Gln Cys Met Pro Gly Phe Gly Gly Arg Thr
    1100                1105                1110
Cys Ser Glu Cys Gln Glu Leu Phe Trp Gly Asp Pro Asp Val Glu
    1115                1120                1125
Cys Arg Ala Cys Asp Cys Asp Pro Arg Gly Ile Glu Thr Pro Gln
    1130                1135                1140
Cys Asp Gln Ser Thr Gly Gln Cys Val Cys Val Glu Gly Val Glu
    1145                1150                1155
Gly Pro Arg Cys Asp Lys Cys Thr Arg Gly Tyr Ser Gly Val Phe
    1160                1165                1170
Pro Asp Cys Thr Pro Cys His Gln Cys Phe Ala Leu Trp Asp Val
    1175                1180                1185
Ile Ile Ala Glu Leu Thr Asn Arg Thr His Arg Phe Leu Glu Lys
    1190                1195                1200
Ala Lys Ala Leu Lys Ile Ser Gly Val Ile Gly Pro Tyr Arg Glu
    1205                1210                1215
Thr Val Asp Ser Val Glu Arg Lys Val Ser Glu Ile Lys Asp Ile
    1220                1225                1230
Leu Ala Gln Ser Pro Ala Ala Glu Pro Leu Lys Asn Ile Gly Asn
    1235                1240                1245
Leu Phe Glu Glu Ala Glu Lys Leu Ile Lys Asp Val Thr Glu Met
    1250                1255                1260
Met Ala Gln Val Glu Val Lys Leu Ser Asp Thr Thr Ser Gln Ser
    1265                1270                1275
```

-continued

Asn Ser Thr Ala Lys Glu Leu Asp Ser Leu Gln Thr Glu Ala Glu
    1280            1285            1290

Ser Leu Asp Asn Thr Val Lys Glu Leu Ala Glu Gln Leu Glu Phe
    1295            1300            1305

Ile Lys Asn Ser Asp Ile Arg Gly Ala Leu Asp Ser Ile Thr Lys
    1310            1315            1320

Tyr Phe Gln Met Ser Leu Glu Ala Glu Glu Arg Val Asn Ala Ser
    1325            1330            1335

Thr Thr Glu Pro Asn Ser Thr Val Glu Gln Ser Ala Leu Met Arg
    1340            1345            1350

Asp Arg Val Glu Asp Val Met Met Glu Arg Glu Ser Gln Phe Lys
    1355            1360            1365

Glu Lys Gln Glu Glu Gln Ala Arg Leu Leu Asp Glu Leu Ala Gly
    1370            1375            1380

Lys Leu Gln Ser Leu Asp Leu Ser Ala Ala Ala Glu Met Thr Cys
    1385            1390            1395

Gly Thr Pro Pro Gly Ala Ser Cys Ser Glu Thr Glu Cys Gly Gly
    1400            1405            1410

Pro Asn Cys Arg Thr Asp Glu Gly Glu Arg Lys Cys Gly Gly Pro
    1415            1420            1425

Gly Cys Gly Gly Leu Val Thr Val Ala His Asn Ala Trp Gln Lys
    1430            1435            1440

Ala Met Asp Leu Asp Gln Asp Val Leu Ser Ala Leu Ala Glu Val
    1445            1450            1455

Glu Gln Leu Ser Lys Met Val Ser Glu Ala Lys Leu Arg Ala Asp
    1460            1465            1470

Glu Ala Lys Gln Ser Ala Glu Asp Ile Leu Leu Lys Thr Asn Ala
    1475            1480            1485

Thr Lys Glu Lys Met Asp Lys Ser Asn Glu Glu Leu Arg Asn Leu
    1490            1495            1500

Ile Lys Gln Ile Arg Asn Phe Leu Thr Gln Asp Ser Ala Asp Leu
    1505            1510            1515

Asp Ser Ile Glu Ala Val Ala Asn Glu Val Leu Lys Met Glu Met
    1520            1525            1530

Pro Ser Thr Pro Gln Gln Leu Gln Asn Leu Thr Glu Asp Ile Arg
    1535            1540            1545

Glu Arg Val Glu Ser Leu Ser Gln Val Glu Val Ile Leu Gln His
    1550            1555            1560

Ser Ala Ala Asp Ile Ala Arg Ala Glu Met Leu Leu Glu Glu Ala
    1565            1570            1575

Lys Arg Ala Ser Lys Ser Ala Thr Asp Val Lys Val Thr Ala Asp
    1580            1585            1590

Met Val Lys Glu Ala Leu Glu Glu Ala Glu Lys Ala Gln Val Ala
    1595            1600            1605

Ala Glu Lys Ala Ile Lys Gln Ala Asp Glu Asp Ile Gln Gly Thr
    1610            1615            1620

Gln Asn Leu Leu Thr Ser Ile Glu Ser Glu Thr Ala Ala Ser Glu
    1625            1630            1635

Glu Thr Leu Phe Asn Ala Ser Gln Arg Ile Ser Glu Leu Glu Arg
    1640            1645            1650

Asn Val Glu Glu Leu Lys Arg Lys Ala Ala Gln Asn Ser Gly Glu
    1655            1660            1665

Ala Glu Tyr Ile Glu Lys Val Val Tyr Thr Val Lys Gln Ser Ala

```
              1670                1675                1680

Glu  Asp  Val  Lys  Lys  Thr  Leu  Asp  Gly  Glu  Leu  Asp  Glu  Lys  Tyr
     1685                1690                1695

Lys  Lys  Val  Glu  Asn  Leu  Ile  Ala  Lys  Lys  Thr  Glu  Glu  Ser  Ala
1700                1705                1710

Asp  Ala  Arg  Arg  Lys  Ala  Glu  Met  Leu  Gln  Asn  Glu  Ala  Lys  Thr
     1715                1720                1725

Leu  Leu  Ala  Gln  Ala  Asn  Ser  Lys  Leu  Gln  Leu  Leu  Lys  Asp  Leu
     1730                1735                1740

Glu  Arg  Lys  Tyr  Glu  Asp  Asn  Gln  Arg  Tyr  Leu  Glu  Asp  Lys  Ala
     1745                1750                1755

Gln  Glu  Leu  Ala  Arg  Leu  Glu  Gly  Glu  Val  Arg  Ser  Leu  Leu  Lys
     1760                1765                1770

Asp  Ile  Ser  Gln  Lys  Val  Ala  Val  Tyr  Ser  Thr  Cys  Leu
     1775                1780                1785

<210> SEQ ID NO 62
<211> LENGTH: 1609
<212> TYPE: PRT
<213> ORGANISM: Homo sapiens

<400> SEQUENCE: 62

Met  Arg  Gly  Ser  His  Arg  Ala  Ala  Pro  Ala  Leu  Arg  Pro  Arg  Gly  Arg
1                 5                  10                 15

Leu  Trp  Pro  Val  Leu  Ala  Val  Leu  Ala  Ala  Ala  Ala  Ala  Gly  Cys
          20                  25                 30

Ala  Gln  Ala  Ala  Met  Asp  Glu  Cys  Thr  Asp  Glu  Gly  Gly  Arg  Pro  Gln
          35                  40                 45

Arg  Cys  Met  Pro  Glu  Phe  Val  Asn  Ala  Ala  Phe  Asn  Val  Thr  Val  Val
50                    55                  60

Ala  Thr  Asn  Thr  Cys  Gly  Thr  Pro  Pro  Glu  Glu  Tyr  Cys  Val  Gln  Thr
65                    70                  75                 80

Gly  Val  Thr  Gly  Val  Thr  Lys  Ser  Cys  His  Leu  Cys  Asp  Ala  Gly  Gln
                 85                  90                 95

Pro  His  Leu  Gln  His  Gly  Ala  Ala  Phe  Leu  Thr  Asp  Tyr  Asn  Asn  Gln
                 100                 105                110

Ala  Asp  Thr  Thr  Trp  Trp  Gln  Ser  Gln  Thr  Met  Leu  Ala  Gly  Val  Gln
          115                 120                125

Tyr  Pro  Ser  Ser  Ile  Asn  Leu  Thr  Leu  His  Leu  Gly  Lys  Ala  Phe  Asp
          130                 135                140

Ile  Thr  Tyr  Val  Arg  Leu  Lys  Phe  His  Thr  Ser  Arg  Pro  Glu  Ser  Phe
145                   150                 155                160

Ala  Ile  Tyr  Lys  Arg  Thr  Arg  Glu  Asp  Gly  Pro  Trp  Ile  Pro  Tyr  Gln
                 165                 170                175

Tyr  Tyr  Ser  Gly  Ser  Cys  Glu  Asn  Thr  Tyr  Ser  Lys  Ala  Asn  Arg  Gly
                 180                 185                190

Phe  Ile  Arg  Thr  Gly  Gly  Asp  Glu  Gln  Gln  Ala  Leu  Cys  Thr  Asp  Glu
          195                 200                205

Phe  Ser  Asp  Ile  Ser  Pro  Leu  Thr  Gly  Gly  Asn  Val  Ala  Phe  Ser  Thr
          210                 215                220

Leu  Glu  Gly  Arg  Pro  Ser  Ala  Tyr  Asn  Phe  Asp  Asn  Ser  Pro  Val  Leu
225                   230                 235                240

Gln  Glu  Trp  Val  Thr  Ala  Thr  Asp  Ile  Arg  Val  Thr  Leu  Asn  Arg  Leu
                 245                 250                255
```

-continued

Asn Thr Phe Gly Asp Glu Val Phe Asn Asp Pro Lys Val Leu Lys Ser
          260                 265                 270

Tyr Tyr Tyr Ala Ile Ser Asp Phe Ala Val Gly Gly Arg Cys Lys Cys
          275                 280                 285

Asn Gly His Ala Ser Glu Cys Met Lys Asn Glu Phe Asp Lys Leu Val
          290                 295                 300

Cys Asn Cys Lys His Asn Thr Tyr Gly Val Asp Cys Glu Lys Cys Leu
305                 310                 315                 320

Pro Phe Phe Asn Asp Arg Pro Trp Arg Arg Ala Thr Ala Glu Ser Ala
                  325                 330                 335

Ser Glu Cys Leu Pro Cys Asp Cys Asn Gly Arg Ser Gln Glu Cys Tyr
              340                 345                 350

Phe Asp Pro Glu Leu Tyr Arg Ser Thr Gly His Gly Gly His Cys Thr
              355                 360                 365

Asn Cys Gln Asp Asn Thr Asp Gly Ala His Cys Glu Arg Cys Arg Glu
          370                 375                 380

Asn Phe Phe Arg Leu Gly Asn Asn Glu Ala Cys Ser Ser Cys His Cys
385                 390                 395                 400

Ser Pro Val Gly Ser Leu Ser Thr Gln Cys Asp Ser Tyr Gly Arg Cys
                  405                 410                 415

Ser Cys Lys Pro Gly Val Met Gly Asp Lys Cys Asp Arg Cys Gln Pro
              420                 425                 430

Gly Phe His Ser Leu Thr Glu Ala Gly Cys Arg Pro Cys Ser Cys Asp
              435                 440                 445

Pro Ser Gly Ser Ile Asp Glu Cys Asn Ile Glu Thr Gly Arg Cys Val
450                 455                 460

Cys Lys Asp Asn Val Glu Gly Phe Asn Cys Glu Arg Cys Lys Pro Gly
465                 470                 475                 480

Phe Phe Asn Leu Glu Ser Ser Asn Pro Arg Gly Cys Thr Pro Cys Phe
              485                 490                 495

Cys Phe Gly His Ser Ser Val Cys Thr Asn Ala Val Gly Tyr Ser Val
              500                 505                 510

Tyr Ser Ile Ser Ser Thr Phe Gln Ile Asp Glu Asp Gly Trp Arg Ala
              515                 520                 525

Glu Gln Arg Asp Gly Ser Glu Ala Ser Leu Glu Trp Ser Ser Glu Arg
          530                 535                 540

Gln Asp Ile Ala Val Ile Ser Asp Ser Tyr Phe Pro Arg Tyr Phe Ile
545                 550                 555                 560

Ala Pro Ala Lys Phe Leu Gly Lys Gln Val Leu Ser Tyr Gly Gln Asn
                  565                 570                 575

Leu Ser Phe Ser Phe Arg Val Asp Arg Arg Asp Thr Arg Leu Ser Ala
              580                 585                 590

Glu Asp Leu Val Leu Glu Gly Ala Gly Leu Arg Val Ser Val Pro Leu
          595                 600                 605

Ile Ala Gln Gly Asn Ser Tyr Pro Ser Glu Thr Thr Val Lys Tyr Val
          610                 615                 620

Phe Arg Leu His Glu Ala Thr Asp Tyr Pro Trp Arg Pro Ala Leu Thr
625                 630                 635                 640

Pro Phe Glu Phe Gln Lys Leu Leu Asn Asn Leu Thr Ser Ile Lys Ile
                  645                 650                 655

Arg Gly Thr Tyr Ser Glu Arg Ser Ala Gly Tyr Leu Asp Asp Val Thr
              660                 665                 670

Leu Ala Ser Ala Arg Pro Gly Pro Gly Val Pro Ala Thr Trp Val Glu

-continued

|     |     |     |     |     | 675 |     |     |     | 680 |     |     |     |     | 685 |     |     |     |
|---|---|---|---|---|---|---|---|---|---|---|---|---|---|---|---|---|---|

Ser Cys Thr Cys Pro Val Gly Tyr Gly Gly Gln Phe Cys Glu Met Cys
690                     695                 700

Leu Ser Gly Tyr Arg Arg Glu Thr Pro Asn Leu Gly Pro Tyr Ser Pro
705                 710                 715                 720

Cys Val Leu Cys Ala Cys Asn Gly His Ser Glu Thr Cys Asp Pro Glu
            725                 730                 735

Thr Gly Val Cys Asn Cys Arg Asp Asn Thr Ala Gly Pro His Cys Glu
        740                 745                 750

Lys Cys Ser Asp Gly Tyr Tyr Gly Asp Ser Thr Ala Gly Thr Ser Ser
        755                 760                 765

Asp Cys Gln Pro Cys Pro Cys Pro Gly Gly Ser Ser Cys Ala Val Val
    770                 775                 780

Pro Lys Thr Lys Glu Val Val Cys Thr Asn Cys Pro Thr Gly Thr Thr
785                 790                 795                 800

Gly Lys Arg Cys Glu Leu Cys Asp Asp Gly Tyr Phe Gly Asp Pro Leu
            805                 810                 815

Gly Arg Asn Gly Pro Val Arg Leu Cys Arg Leu Cys Gln Cys Ser Asp
        820                 825                 830

Asn Ile Asp Pro Asn Ala Val Gly Asn Cys Asn Arg Leu Thr Gly Glu
        835                 840                 845

Cys Leu Lys Cys Ile Tyr Asn Thr Ala Gly Phe Tyr Cys Asp Arg Cys
    850                 855                 860

Lys Asp Gly Phe Phe Gly Asn Pro Leu Ala Pro Asn Pro Ala Asp Lys
865                 870                 875                 880

Cys Lys Ala Cys Asn Cys Asn Leu Tyr Gly Thr Met Lys Gln Gln Ser
            885                 890                 895

Ser Cys Asn Pro Val Thr Gly Gln Cys Glu Cys Leu Pro His Val Thr
        900                 905                 910

Gly Gln Asp Cys Gly Ala Cys Asp Pro Gly Phe Tyr Asn Leu Gln Ser
        915                 920                 925

Gly Gln Gly Cys Glu Arg Cys Asp Cys His Ala Leu Gly Ser Thr Asn
    930                 935                 940

Gly Gln Cys Asp Ile Arg Thr Gly Gln Cys Glu Cys Gln Pro Gly Ile
945                 950                 955                 960

Thr Gly Gln His Cys Glu Arg Cys Glu Val Asn His Phe Gly Phe Gly
            965                 970                 975

Pro Glu Gly Cys Lys Pro Cys Asp Cys His Pro Glu Gly Ser Leu Ser
        980                 985                 990

Leu Gln Cys Lys Asp Asp Gly Arg Cys Glu Cys Arg Glu Gly Phe Val
        995                 1000                1005

Gly Asn Arg Cys Asp Gln Cys Glu Glu Asn Tyr Phe Tyr Asn Arg
    1010                1015                1020

Ser Trp Pro Gly Cys Gln Glu Cys Pro Ala Cys Tyr Arg Leu Val
    1025                1030                1035

Lys Asp Lys Val Ala Asp His Arg Val Lys Leu Gln Glu Leu Glu
    1040                1045                1050

Ser Leu Ile Ala Asn Leu Gly Thr Gly Asp Glu Met Val Thr Asp
    1055                1060                1065

Gln Ala Phe Glu Asp Arg Leu Lys Glu Ala Glu Arg Glu Val Met
    1070                1075                1080

Asp Leu Leu Arg Glu Ala Gln Asp Val Lys Asp Val Asp Gln Asn
    1085                1090                1095

```
Leu Met Asp Arg Leu Gln Arg Val Asn Asn Thr Leu Ser Ser Gln
    1100                1105                1110

Ile Ser Arg Leu Gln Asn Ile Arg Asn Thr Ile Glu Glu Thr Gly
    1115                1120                1125

Asn Leu Ala Glu Gln Ala Arg Ala His Val Glu Asn Thr Glu Arg
    1130                1135                1140

Leu Ile Glu Ile Ala Ser Arg Glu Leu Glu Lys Ala Lys Val Ala
    1145                1150                1155

Ala Ala Asn Val Ser Val Thr Gln Pro Glu Ser Thr Gly Asp Pro
    1160                1165                1170

Asn Asn Met Thr Leu Leu Ala Glu Glu Ala Arg Lys Leu Ala Glu
    1175                1180                1185

Arg His Lys Gln Glu Ala Asp Asp Ile Val Arg Val Ala Lys Thr
    1190                1195                1200

Ala Asn Asp Thr Ser Thr Glu Ala Tyr Asn Leu Leu Leu Arg Thr
    1205                1210                1215

Leu Ala Gly Glu Asn Gln Thr Ala Phe Glu Ile Glu Glu Leu Asn
    1220                1225                1230

Arg Lys Tyr Glu Gln Ala Lys Asn Ile Ser Gln Asp Leu Glu Lys
    1235                1240                1245

Gln Ala Ala Arg Val His Glu Glu Ala Lys Arg Ala Gly Asp Lys
    1250                1255                1260

Ala Val Glu Ile Tyr Ala Ser Val Ala Gln Leu Ser Pro Leu Asp
    1265                1270                1275

Ser Glu Thr Leu Glu Asn Glu Ala Asn Asn Ile Lys Met Glu Ala
    1280                1285                1290

Glu Asn Leu Glu Gln Leu Ile Asp Gln Lys Leu Lys Asp Tyr Glu
    1295                1300                1305

Asp Leu Arg Glu Asp Met Arg Gly Lys Glu Leu Glu Val Lys Asn
    1310                1315                1320

Leu Leu Glu Lys Gly Lys Thr Glu Gln Gln Thr Ala Asp Gln Leu
    1325                1330                1335

Leu Ala Arg Ala Asp Ala Ala Lys Ala Leu Ala Glu Glu Ala Ala
    1340                1345                1350

Lys Lys Gly Arg Asp Thr Leu Gln Glu Ala Asn Asp Ile Leu Asn
    1355                1360                1365

Asn Leu Lys Asp Phe Asp Arg Arg Val Asn Asp Asn Lys Thr Ala
    1370                1375                1380

Ala Glu Glu Ala Leu Arg Lys Ile Pro Ala Ile Asn Gln Thr Ile
    1385                1390                1395

Thr Glu Ala Asn Glu Lys Thr Arg Glu Ala Gln Gln Ala Leu Gly
    1400                1405                1410

Ser Ala Ala Ala Asp Ala Thr Glu Ala Lys Asn Lys Ala His Glu
    1415                1420                1425

Ala Glu Arg Ile Ala Ser Ala Val Gln Lys Asn Ala Thr Ser Thr
    1430                1435                1440

Lys Ala Glu Ala Glu Arg Thr Phe Ala Glu Val Thr Asp Leu Asp
    1445                1450                1455

Asn Glu Val Asn Asn Met Leu Lys Gln Leu Gln Glu Ala Glu Lys
    1460                1465                1470

Glu Leu Lys Arg Lys Gln Asp Asp Ala Asp Gln Asp Met Met Met
    1475                1480                1485
```

```
Ala Gly Met Ala Ser Gln Ala Ala Gln Glu Ala Glu Ile Asn Ala
    1490                1495                1500

Arg Lys Ala Lys Asn Ser Val Thr Ser Leu Leu Ser Ile Ile Asn
1505                1510                1515

Asp Leu Leu Glu Gln Leu Gly Gln Leu Asp Thr Val Asp Leu Asn
    1520                1525                1530

Lys Leu Asn Glu Ile Glu Gly Thr Leu Asn Lys Ala Lys Asp Glu
1535                1540                1545

Met Lys Val Ser Asp Leu Asp Arg Lys Val Ser Asp Leu Glu Asn
    1550                1555                1560

Glu Ala Lys Lys Gln Glu Ala Ala Ile Met Asp Tyr Asn Arg Asp
1565                1570                1575

Ile Glu Glu Ile Met Lys Asp Ile Arg Asn Leu Glu Asp Ile Arg
    1580                1585                1590

Lys Thr Leu Pro Ser Gly Cys Phe Asn Thr Pro Ser Ile Glu Lys
1595                1600                1605

Pro

<210> SEQ ID NO 63
<211> LENGTH: 2386
<212> TYPE: PRT
<213> ORGANISM: Homo sapiens

<400> SEQUENCE: 63

Met Leu Arg Gly Pro Gly Pro Gly Leu Leu Leu Leu Ala Val Gln Cys
1               5                   10                  15

Leu Gly Thr Ala Val Pro Ser Thr Gly Ala Ser Lys Ser Lys Arg Gln
                20                  25                  30

Ala Gln Gln Met Val Gln Pro Gln Ser Pro Val Ala Val Ser Gln Ser
            35                  40                  45

Lys Pro Gly Cys Tyr Asp Asn Gly Lys His Tyr Gln Ile Asn Gln Gln
        50                  55                  60

Trp Glu Arg Thr Tyr Leu Gly Asn Ala Leu Val Cys Thr Cys Tyr Gly
65                  70                  75                  80

Gly Ser Arg Gly Phe Asn Cys Glu Ser Lys Pro Glu Ala Glu Glu Thr
                85                  90                  95

Cys Phe Asp Lys Tyr Thr Gly Asn Thr Tyr Arg Val Gly Asp Thr Tyr
            100                 105                 110

Glu Arg Pro Lys Asp Ser Met Ile Trp Asp Cys Thr Cys Ile Gly Ala
        115                 120                 125

Gly Arg Gly Arg Ile Ser Cys Thr Ile Ala Asn Arg Cys His Glu Gly
    130                 135                 140

Gly Gln Ser Tyr Lys Ile Gly Asp Thr Trp Arg Arg Pro His Glu Thr
145                 150                 155                 160

Gly Gly Tyr Met Leu Glu Cys Val Cys Leu Gly Asn Gly Lys Gly Glu
                165                 170                 175

Trp Thr Cys Lys Pro Ile Ala Glu Lys Cys Phe Asp His Ala Ala Gly
            180                 185                 190

Thr Ser Tyr Val Val Gly Glu Thr Trp Glu Lys Pro Tyr Gln Gly Trp
        195                 200                 205

Met Met Val Asp Cys Thr Cys Leu Gly Glu Gly Ser Gly Arg Ile Thr
    210                 215                 220

Cys Thr Ser Arg Asn Arg Cys Asn Asp Gln Asp Thr Arg Thr Ser Tyr
225                 230                 235                 240
```

-continued

Arg Ile Gly Asp Thr Trp Ser Lys Lys Asp Asn Arg Gly Asn Leu Leu
            245                 250                 255

Gln Cys Ile Cys Thr Gly Asn Gly Arg Gly Glu Trp Lys Cys Glu Arg
            260                 265                 270

His Thr Ser Val Gln Thr Thr Ser Ser Gly Ser Gly Pro Phe Thr Asp
            275                 280                 285

Val Arg Ala Ala Val Tyr Gln Pro Gln Pro His Pro Gln Pro Pro Pro
            290                 295                 300

Tyr Gly His Cys Val Thr Asp Ser Gly Val Val Tyr Ser Val Gly Met
305                 310                 315                 320

Gln Trp Leu Lys Thr Gln Gly Asn Lys Gln Met Leu Cys Thr Cys Leu
            325                 330                 335

Gly Asn Gly Val Ser Cys Gln Glu Thr Ala Val Thr Gln Thr Tyr Gly
            340                 345                 350

Gly Asn Ser Asn Gly Glu Pro Cys Val Leu Pro Phe Thr Tyr Asn Gly
            355                 360                 365

Arg Thr Phe Tyr Ser Cys Thr Thr Glu Gly Arg Gln Asp Gly His Leu
            370                 375                 380

Trp Cys Ser Thr Thr Ser Asn Tyr Glu Gln Asp Gln Lys Tyr Ser Phe
385                 390                 395                 400

Cys Thr Asp His Thr Val Leu Val Gln Thr Arg Gly Gly Asn Ser Asn
            405                 410                 415

Gly Ala Leu Cys His Phe Pro Phe Leu Tyr Asn Asn His Asn Tyr Thr
            420                 425                 430

Asp Cys Thr Ser Glu Gly Arg Arg Asp Asn Met Lys Trp Cys Gly Thr
            435                 440                 445

Thr Gln Asn Tyr Asp Ala Asp Gln Lys Phe Gly Phe Cys Pro Met Ala
            450                 455                 460

Ala His Glu Glu Ile Cys Thr Thr Asn Glu Gly Val Met Tyr Arg Ile
465                 470                 475                 480

Gly Asp Gln Trp Asp Lys Gln His Asp Met Gly His Met Met Arg Cys
            485                 490                 495

Thr Cys Val Gly Asn Gly Arg Gly Glu Trp Thr Cys Ile Ala Tyr Ser
            500                 505                 510

Gln Leu Arg Asp Gln Cys Ile Val Asp Asp Ile Thr Tyr Asn Val Asn
            515                 520                 525

Asp Thr Phe His Lys Arg His Glu Glu Gly His Met Leu Asn Cys Thr
            530                 535                 540

Cys Phe Gly Gln Gly Arg Gly Arg Trp Lys Cys Asp Pro Val Asp Gln
545                 550                 555                 560

Cys Gln Asp Ser Glu Thr Gly Thr Phe Tyr Gln Ile Gly Asp Ser Trp
            565                 570                 575

Glu Lys Tyr Val His Gly Val Arg Tyr Gln Cys Tyr Cys Tyr Gly Arg
            580                 585                 590

Gly Ile Gly Glu Trp His Cys Gln Pro Leu Gln Thr Tyr Pro Ser Ser
            595                 600                 605

Ser Gly Pro Val Glu Val Phe Ile Thr Glu Thr Pro Ser Gln Pro Asn
            610                 615                 620

Ser His Pro Ile Gln Trp Asn Ala Pro Gln Pro Ser His Ile Ser Lys
625                 630                 635                 640

Tyr Ile Leu Arg Trp Arg Pro Lys Asn Ser Val Gly Arg Trp Lys Glu
            645                 650                 655

Ala Thr Ile Pro Gly His Leu Asn Ser Tyr Thr Ile Lys Gly Leu Lys

-continued

```
                660                 665                 670
Pro Gly Val Val Tyr Glu Gly Gln Leu Ile Ser Ile Gln Gln Tyr Gly
            675                 680                 685

His Gln Glu Val Thr Arg Phe Asp Phe Thr Thr Ser Thr Ser Thr
    690                 695                 700

Pro Val Thr Ser Asn Thr Val Thr Gly Glu Thr Thr Pro Phe Ser Pro
705                 710                 715                 720

Leu Val Ala Thr Ser Glu Ser Val Thr Glu Ile Thr Ala Ser Ser Phe
                725                 730                 735

Val Val Ser Trp Val Ser Ala Ser Asp Thr Val Ser Gly Phe Arg Val
            740                 745                 750

Glu Tyr Glu Leu Ser Glu Glu Gly Asp Glu Pro Gln Tyr Leu Asp Leu
        755                 760                 765

Pro Ser Thr Ala Thr Ser Val Asn Ile Pro Asp Leu Leu Pro Gly Arg
    770                 775                 780

Lys Tyr Ile Val Asn Val Tyr Gln Ile Ser Glu Asp Gly Glu Gln Ser
785                 790                 795                 800

Leu Ile Leu Ser Thr Ser Gln Thr Thr Ala Pro Asp Ala Pro Pro Asp
                805                 810                 815

Thr Thr Val Asp Gln Val Asp Asp Thr Ser Ile Val Val Arg Trp Ser
            820                 825                 830

Arg Pro Gln Ala Pro Ile Thr Gly Tyr Arg Ile Val Tyr Ser Pro Ser
        835                 840                 845

Val Glu Gly Ser Ser Thr Glu Leu Asn Leu Pro Glu Thr Ala Asn Ser
    850                 855                 860

Val Thr Leu Ser Asp Leu Gln Pro Gly Val Gln Tyr Asn Ile Thr Ile
865                 870                 875                 880

Tyr Ala Val Glu Glu Asn Gln Glu Ser Thr Pro Val Val Ile Gln Gln
                885                 890                 895

Glu Thr Thr Gly Thr Pro Arg Ser Asp Thr Val Pro Ser Pro Arg Asp
            900                 905                 910

Leu Gln Phe Val Glu Val Thr Asp Val Lys Val Thr Ile Met Trp Thr
        915                 920                 925

Pro Pro Glu Ser Ala Val Thr Gly Tyr Arg Val Asp Val Ile Pro Val
    930                 935                 940

Asn Leu Pro Gly Glu His Gly Gln Arg Leu Pro Ile Ser Arg Asn Thr
945                 950                 955                 960

Phe Ala Glu Val Thr Gly Leu Ser Pro Gly Val Thr Tyr Tyr Phe Lys
                965                 970                 975

Val Phe Ala Val Ser His Gly Arg Glu Ser Lys Pro Leu Thr Ala Gln
            980                 985                 990

Gln Thr Thr Lys Leu Asp Ala Pro Thr Asn Leu Gln Phe Val Asn Glu
        995                 1000                1005

Thr Asp Ser Thr Val Leu Val Arg Trp Thr Pro Pro Arg Ala Gln
    1010                1015                1020

Ile Thr Gly Tyr Arg Leu Thr Val Gly Leu Thr Arg Arg Gly Gln
    1025                1030                1035

Pro Arg Gln Tyr Asn Val Gly Pro Ser Val Ser Lys Tyr Pro Leu
    1040                1045                1050

Arg Asn Leu Gln Pro Ala Ser Glu Tyr Thr Val Ser Leu Val Ala
    1055                1060                1065

Ile Lys Gly Asn Gln Glu Ser Pro Lys Ala Thr Gly Val Phe Thr
    1070                1075                1080
```

```
Thr Leu Gln Pro Gly Ser Ser Ile Pro Pro Tyr Asn Thr Glu Val
    1085            1090            1095

Thr Glu Thr Thr Ile Val Ile Thr Trp Thr Pro Ala Pro Arg Ile
    1100            1105            1110

Gly Phe Lys Leu Gly Val Arg Pro Ser Gln Gly Gly Glu Ala Pro
    1115            1120            1125

Arg Glu Val Thr Ser Asp Ser Gly Ser Ile Val Val Ser Gly Leu
    1130            1135            1140

Thr Pro Gly Val Glu Tyr Val Tyr Thr Ile Gln Val Leu Arg Asp
    1145            1150            1155

Gly Gln Glu Arg Asp Ala Pro Ile Val Asn Lys Val Val Thr Pro
    1160            1165            1170

Leu Ser Pro Pro Thr Asn Leu His Leu Glu Ala Asn Pro Asp Thr
    1175            1180            1185

Gly Val Leu Thr Val Ser Trp Glu Arg Ser Thr Thr Pro Asp Ile
    1190            1195            1200

Thr Gly Tyr Arg Ile Thr Thr Thr Pro Thr Asn Gly Gln Gln Gly
    1205            1210            1215

Asn Ser Leu Glu Glu Val Val His Ala Asp Gln Ser Ser Cys Thr
    1220            1225            1230

Phe Asp Asn Leu Ser Pro Gly Leu Glu Tyr Asn Val Ser Val Tyr
    1235            1240            1245

Thr Val Lys Asp Asp Lys Glu Ser Val Pro Ile Ser Asp Thr Ile
    1250            1255            1260

Ile Pro Ala Val Pro Pro Thr Asp Leu Arg Phe Thr Asn Ile
    1265            1270            1275

Gly Pro Asp Thr Met Arg Val Thr Trp Ala Pro Pro Pro Ser Ile
    1280            1285            1290

Asp Leu Thr Asn Phe Leu Val Arg Tyr Ser Pro Val Lys Asn Glu
    1295            1300            1305

Glu Asp Val Ala Glu Leu Ser Ile Ser Pro Ser Asp Asn Ala Val
    1310            1315            1320

Val Leu Thr Asn Leu Leu Pro Gly Thr Glu Tyr Val Val Ser Val
    1325            1330            1335

Ser Ser Val Tyr Glu Gln His Glu Ser Thr Pro Leu Arg Gly Arg
    1340            1345            1350

Gln Lys Thr Gly Leu Asp Ser Pro Thr Gly Ile Asp Phe Ser Asp
    1355            1360            1365

Ile Thr Ala Asn Ser Phe Thr Val His Trp Ile Ala Pro Arg Ala
    1370            1375            1380

Thr Ile Thr Gly Tyr Arg Ile Arg His His Pro Glu His Phe Ser
    1385            1390            1395

Gly Arg Pro Arg Glu Asp Arg Val Pro His Ser Arg Asn Ser Ile
    1400            1405            1410

Thr Leu Thr Asn Leu Thr Pro Gly Thr Glu Tyr Val Val Ser Ile
    1415            1420            1425

Val Ala Leu Asn Gly Arg Glu Glu Ser Pro Leu Leu Ile Gly Gln
    1430            1435            1440

Gln Ser Thr Val Ser Asp Val Pro Arg Asp Leu Glu Val Val Ala
    1445            1450            1455

Ala Thr Pro Thr Ser Leu Leu Ile Ser Trp Asp Ala Pro Ala Val
    1460            1465            1470
```

```
Thr Val Arg Tyr Tyr Arg Ile Thr Tyr Gly Glu Thr Gly Gly Asn
1475                1480                1485

Ser Pro Val Gln Glu Phe Thr Val Pro Gly Ser Lys Ser Thr Ala
1490                1495                1500

Thr Ile Ser Gly Leu Lys Pro Gly Val Asp Tyr Thr Ile Thr Val
1505                1510                1515

Tyr Ala Val Thr Gly Arg Gly Asp Ser Pro Ala Ser Ser Lys Pro
1520                1525                1530

Ile Ser Ile Asn Tyr Arg Thr Glu Ile Asp Lys Pro Ser Gln Met
1535                1540                1545

Gln Val Thr Asp Val Gln Asp Asn Ser Ile Ser Val Lys Trp Leu
1550                1555                1560

Pro Ser Ser Ser Pro Val Thr Gly Tyr Arg Val Thr Thr Thr Pro
1565                1570                1575

Lys Asn Gly Pro Gly Pro Thr Lys Thr Lys Thr Ala Gly Pro Asp
1580                1585                1590

Gln Thr Glu Met Thr Ile Glu Gly Leu Gln Pro Thr Val Glu Tyr
1595                1600                1605

Val Val Ser Val Tyr Ala Gln Asn Pro Ser Gly Glu Ser Gln Pro
1610                1615                1620

Leu Val Gln Thr Ala Val Thr Asn Ile Asp Arg Pro Lys Gly Leu
1625                1630                1635

Ala Phe Thr Asp Val Asp Val Asp Ser Ile Lys Ile Ala Trp Glu
1640                1645                1650

Ser Pro Gln Gly Gln Val Ser Arg Tyr Arg Val Thr Tyr Ser Ser
1655                1660                1665

Pro Glu Asp Gly Ile His Glu Leu Phe Pro Ala Pro Asp Gly Glu
1670                1675                1680

Glu Asp Thr Ala Glu Leu Gln Gly Leu Arg Pro Gly Ser Glu Tyr
1685                1690                1695

Thr Val Ser Val Val Ala Leu His Asp Asp Met Glu Ser Gln Pro
1700                1705                1710

Leu Ile Gly Thr Gln Ser Thr Ala Ile Pro Ala Pro Thr Asp Leu
1715                1720                1725

Lys Phe Thr Gln Val Thr Pro Thr Ser Leu Ser Ala Gln Trp Thr
1730                1735                1740

Pro Pro Asn Val Gln Leu Thr Gly Tyr Arg Val Arg Val Thr Pro
1745                1750                1755

Lys Glu Lys Thr Gly Pro Met Lys Glu Ile Asn Leu Ala Pro Asp
1760                1765                1770

Ser Ser Ser Val Val Val Ser Gly Leu Met Val Ala Thr Lys Tyr
1775                1780                1785

Glu Val Ser Val Tyr Ala Leu Lys Asp Thr Leu Thr Ser Arg Pro
1790                1795                1800

Ala Gln Gly Val Val Thr Thr Leu Glu Asn Val Ser Pro Pro Arg
1805                1810                1815

Arg Ala Arg Val Thr Asp Ala Thr Glu Thr Thr Ile Thr Ile Ser
1820                1825                1830

Trp Arg Thr Lys Thr Glu Thr Ile Thr Gly Phe Gln Val Asp Ala
1835                1840                1845

Val Pro Ala Asn Gly Gln Thr Pro Ile Gln Arg Thr Ile Lys Pro
1850                1855                1860

Asp Val Arg Ser Tyr Thr Ile Thr Gly Leu Gln Pro Gly Thr Asp
```

-continued

```
            1865                1870                1875
Tyr Lys Ile Tyr Leu Tyr Thr Leu Asn Asp Asn Ala Arg Ser Ser
            1880                1885                1890
Pro Val Val Ile Asp Ala Ser Thr Ala Ile Asp Ala Pro Ser Asn
            1895                1900                1905
Leu Arg Phe Leu Ala Thr Thr Pro Asn Ser Leu Leu Val Ser Trp
            1910                1915                1920
Gln Pro Pro Arg Ala Arg Ile Thr Gly Tyr Ile Ile Lys Tyr Glu
            1925                1930                1935
Lys Pro Gly Ser Pro Pro Arg Glu Val Val Pro Arg Pro Arg Pro
            1940                1945                1950
Gly Val Thr Glu Ala Thr Ile Thr Gly Leu Glu Pro Gly Thr Glu
            1955                1960                1965
Tyr Thr Ile Tyr Val Ile Ala Leu Lys Asn Asn Gln Lys Ser Glu
            1970                1975                1980
Pro Leu Ile Gly Arg Lys Lys Thr Asp Glu Leu Pro Gln Leu Val
            1985                1990                1995
Thr Leu Pro His Pro Asn Leu His Gly Pro Glu Ile Leu Asp Val
            2000                2005                2010
Pro Ser Thr Val Gln Lys Thr Pro Phe Val Thr His Pro Gly Tyr
            2015                2020                2025
Asp Thr Gly Asn Gly Ile Gln Leu Pro Gly Thr Ser Gly Gln Gln
            2030                2035                2040
Pro Ser Val Gly Gln Gln Met Ile Phe Glu Glu His Gly Phe Arg
            2045                2050                2055
Arg Thr Thr Pro Pro Thr Thr Ala Thr Pro Ile Arg His Arg Pro
            2060                2065                2070
Arg Pro Tyr Pro Pro Asn Val Gly Glu Glu Ile Gln Ile Gly His
            2075                2080                2085
Ile Pro Arg Glu Asp Val Asp Tyr His Leu Tyr Pro His Gly Pro
            2090                2095                2100
Gly Leu Asn Pro Asn Ala Ser Thr Gly Gln Glu Ala Leu Ser Gln
            2105                2110                2115
Thr Thr Ile Ser Trp Ala Pro Phe Gln Asp Thr Ser Glu Tyr Ile
            2120                2125                2130
Ile Ser Cys His Pro Val Gly Thr Asp Glu Glu Pro Leu Gln Phe
            2135                2140                2145
Arg Val Pro Gly Thr Ser Ser Ala Thr Leu Thr Gly Leu Thr
            2150                2155                2160
Arg Gly Ala Thr Tyr Asn Val Ile Val Glu Ala Leu Lys Asp Gln
            2165                2170                2175
Gln Arg His Lys Val Arg Glu Val Val Thr Val Gly Asn Ser
            2180                2185                2190
Val Asn Glu Gly Leu Asn Gln Pro Thr Asp Asp Ser Cys Phe Asp
            2195                2200                2205
Pro Tyr Thr Val Ser His Tyr Ala Val Gly Asp Glu Trp Glu Arg
            2210                2215                2220
Met Ser Glu Ser Gly Phe Lys Leu Leu Cys Gln Cys Leu Gly Phe
            2225                2230                2235
Gly Ser Gly His Phe Arg Cys Asp Ser Ser Arg Trp Cys His Asp
            2240                2245                2250
Asn Gly Val Asn Tyr Lys Ile Gly Glu Lys Trp Asp Arg Gln Gly
            2255                2260                2265
```

```
Glu Asn Gly Gln Met Met Ser Cys Thr Cys Leu Gly Asn Gly Lys
    2270            2275                2280

Gly Glu Phe Lys Cys Asp Pro His Glu Ala Thr Cys Tyr Asp Asp
    2285            2290                2295

Gly Lys Thr Tyr His Val Gly Glu Gln Trp Gln Lys Glu Tyr Leu
    2300            2305                2310

Gly Ala Ile Cys Ser Cys Thr Cys Phe Gly Gly Gln Arg Gly Trp
    2315            2320                2325

Arg Cys Asp Asn Cys Arg Arg Pro Gly Gly Glu Pro Ser Pro Glu
    2330            2335                2340

Gly Thr Thr Gly Gln Ser Tyr Asn Gln Tyr Ser Gln Arg Tyr His
    2345            2350                2355

Gln Arg Thr Asn Thr Asn Val Asn Cys Pro Ile Glu Cys Phe Met
    2360            2365                2370

Pro Leu Asp Val Gln Ala Asp Arg Glu Asp Ser Arg Glu
    2375            2380                2385

<210> SEQ ID NO 64
<211> LENGTH: 786
<212> TYPE: PRT
<213> ORGANISM: Homo sapiens

<400> SEQUENCE: 64

Met Ala Gly Leu Thr Ala Ala Pro Arg Pro Gly Val Leu Leu Leu
1               5                   10                  15

Leu Leu Ser Ile Leu His Pro Ser Arg Pro Gly Gly Val Pro Gly Ala
                20                  25                  30

Ile Pro Gly Gly Val Pro Gly Gly Val Phe Tyr Pro Gly Ala Gly Leu
            35                  40                  45

Gly Ala Leu Gly Gly Gly Ala Leu Gly Pro Gly Gly Lys Pro Leu Lys
        50                  55                  60

Pro Val Pro Gly Gly Leu Ala Gly Ala Gly Leu Gly Ala Gly Leu Gly
65                  70                  75                  80

Ala Phe Pro Ala Val Thr Phe Pro Gly Ala Leu Val Pro Gly Gly Val
                85                  90                  95

Ala Asp Ala Ala Ala Ala Tyr Lys Ala Ala Lys Ala Gly Ala Gly Leu
            100                 105                 110

Gly Gly Val Pro Gly Val Gly Gly Leu Gly Val Ser Ala Gly Ala Val
        115                 120                 125

Val Pro Gln Pro Gly Ala Gly Val Lys Pro Gly Lys Val Pro Gly Val
    130                 135                 140

Gly Leu Pro Gly Val Tyr Pro Gly Gly Val Leu Pro Gly Ala Arg Phe
145                 150                 155                 160

Pro Gly Val Gly Val Leu Pro Gly Val Pro Thr Gly Ala Gly Val Lys
                165                 170                 175

Pro Lys Ala Pro Gly Val Gly Gly Ala Phe Ala Gly Ile Pro Gly Val
            180                 185                 190

Gly Pro Phe Gly Gly Pro Gln Pro Gly Val Pro Leu Gly Tyr Pro Ile
        195                 200                 205

Lys Ala Pro Lys Leu Pro Gly Gly Tyr Gly Leu Pro Tyr Thr Thr Gly
    210                 215                 220

Lys Leu Pro Tyr Gly Tyr Gly Pro Gly Gly Val Ala Gly Ala Ala Gly
225                 230                 235                 240

Lys Ala Gly Tyr Pro Thr Gly Thr Gly Val Gly Pro Gln Ala Ala Ala
```

```
                       245                 250                 255
Ala Ala Ala Ala Lys Ala Ala Lys Phe Gly Ala Gly Ala Ala Gly
                260                 265                 270

Val Leu Pro Gly Val Gly Gly Ala Gly Val Pro Gly Val Pro Gly Ala
            275                 280                 285

Ile Pro Gly Ile Gly Gly Ile Ala Gly Val Gly Thr Pro Ala Ala Ala
        290                 295                 300

Ala Ala Ala Ala Ala Ala Ala Lys Ala Ala Lys Tyr Gly Ala Ala Ala
305                 310                 315                 320

Gly Leu Val Pro Gly Pro Gly Phe Gly Pro Gly Val Val Gly Val
                325                 330                 335

Pro Gly Ala Gly Val Pro Gly Val Gly Val Pro Gly Ala Gly Ile Pro
                340                 345                 350

Val Val Pro Gly Ala Gly Ile Pro Gly Ala Ala Val Pro Gly Val Val
                355                 360                 365

Ser Pro Glu Ala Ala Ala Lys Ala Ala Ala Lys Ala Ala Lys Tyr Gly
        370                 375                 380

Ala Arg Pro Gly Val Gly Val Gly Gly Ile Pro Thr Tyr Gly Val Gly
385                 390                 395                 400

Ala Gly Gly Phe Pro Gly Phe Gly Val Gly Val Gly Ile Pro Gly
                405                 410                 415

Val Ala Gly Val Pro Gly Val Gly Val Pro Gly Val Gly Gly Val
            420                 425                 430

Pro Gly Val Gly Ile Ser Pro Glu Ala Gln Ala Ala Ala Ala Lys
                435                 440                 445

Ala Ala Lys Tyr Gly Ala Ala Gly Ala Gly Val Leu Gly Gly Leu Val
        450                 455                 460

Pro Gly Pro Gln Ala Ala Val Pro Gly Val Pro Gly Thr Gly Gly Val
465                 470                 475                 480

Pro Gly Val Gly Thr Pro Ala Ala Ala Ala Lys Ala Ala Ala Lys
                485                 490                 495

Ala Ala Gln Phe Gly Leu Val Pro Gly Val Gly Val Ala Pro Gly Val
                500                 505                 510

Gly Val Ala Pro Gly Val Gly Val Ala Pro Gly Val Gly Leu Ala Pro
            515                 520                 525

Gly Val Gly Val Ala Pro Gly Val Gly Val Ala Pro Gly Val Gly Val
            530                 535                 540

Ala Pro Gly Ile Gly Pro Gly Gly Val Ala Ala Ala Lys Ser Ala
545                 550                 555                 560

Ala Lys Val Ala Ala Lys Ala Gln Leu Arg Ala Ala Ala Gly Leu Gly
                565                 570                 575

Ala Gly Ile Pro Gly Leu Gly Val Val Gly Val Pro Gly Leu Gly
            580                 585                 590

Val Gly Ala Gly Val Pro Gly Leu Gly Val Ala Gly Val Pro Gly
            595                 600                 605

Phe Gly Ala Gly Ala Asp Glu Gly Val Arg Arg Ser Leu Ser Pro Glu
        610                 615                 620

Leu Arg Glu Gly Asp Pro Ser Ser Ser Gln His Leu Pro Ser Thr Pro
625                 630                 635                 640

Ser Ser Pro Arg Val Pro Gly Ala Leu Ala Ala Ala Lys Ala Ala Lys
                645                 650                 655

Tyr Gly Ala Ala Val Pro Gly Val Leu Gly Gly Leu Gly Ala Leu Gly
                660                 665                 670
```

```
Gly Val Gly Ile Pro Gly Gly Val Gly Ala Gly Pro Ala Ala Ala
            675                 680                 685

Ala Ala Ala Ala Lys Ala Ala Ala Lys Ala Ala Gln Phe Gly Leu Val
        690                 695                 700

Gly Ala Ala Gly Leu Gly Gly Leu Gly Val Gly Gly Leu Gly Val Pro
705                 710                 715                 720

Gly Val Gly Gly Leu Gly Gly Ile Pro Pro Ala Ala Ala Lys Ala
            725                 730                 735

Ala Lys Tyr Gly Ala Ala Gly Leu Gly Gly Val Leu Gly Gly Ala Gly
        740                 745                 750

Gln Phe Pro Leu Gly Gly Val Ala Ala Arg Pro Gly Phe Gly Leu Ser
            755                 760                 765

Pro Ile Phe Pro Gly Gly Ala Cys Leu Gly Lys Ala Cys Gly Arg Lys
770                 775                 780

Arg Lys
785

<210> SEQ ID NO 65
<211> LENGTH: 314
<212> TYPE: PRT
<213> ORGANISM: Homo sapiens

<400> SEQUENCE: 65

Met Arg Ile Ala Val Ile Cys Phe Cys Leu Leu Gly Ile Thr Cys Ala
1               5                   10                  15

Ile Pro Val Lys Gln Ala Asp Ser Gly Ser Ser Glu Glu Lys Gln Leu
            20                  25                  30

Tyr Asn Lys Tyr Pro Asp Ala Val Ala Thr Trp Leu Asn Pro Asp Pro
        35                  40                  45

Ser Gln Lys Gln Asn Leu Leu Ala Pro Gln Asn Ala Val Ser Ser Glu
    50                  55                  60

Glu Thr Asn Asp Phe Lys Gln Glu Thr Leu Pro Ser Lys Ser Asn Glu
65                  70                  75                  80

Ser His Asp His Met Asp Asp Met Asp Asp Glu Asp Asp Asp Asp His
                85                  90                  95

Val Asp Ser Gln Asp Ser Ile Asp Ser Asn Asp Ser Asp Asp Val Asp
            100                 105                 110

Asp Thr Asp Asp Ser His Gln Ser Asp Glu Ser His His Ser Asp Glu
        115                 120                 125

Ser Asp Glu Leu Val Thr Asp Phe Pro Thr Asp Leu Pro Ala Thr Glu
    130                 135                 140

Val Phe Thr Pro Val Val Pro Thr Val Asp Thr Tyr Asp Gly Arg Gly
145                 150                 155                 160

Asp Ser Val Val Tyr Gly Leu Arg Ser Lys Ser Lys Lys Phe Arg Arg
                165                 170                 175

Pro Asp Ile Gln Tyr Pro Asp Ala Thr Asp Glu Asp Ile Thr Ser His
            180                 185                 190

Met Glu Ser Glu Glu Leu Asn Gly Ala Tyr Lys Ala Ile Pro Val Ala
        195                 200                 205

Gln Asp Leu Asn Ala Pro Ser Asp Trp Asp Ser Arg Gly Lys Asp Ser
    210                 215                 220

Tyr Glu Thr Ser Gln Leu Asp Asp Gln Ser Ala Glu Thr His Ser His
225                 230                 235                 240

Lys Gln Ser Arg Leu Tyr Lys Arg Lys Ala Asn Asp Glu Ser Asn Glu
```

-continued

```
                245                 250                 255
His Ser Asp Val Ile Asp Ser Gln Glu Leu Ser Lys Val Ser Arg Glu
            260                 265                 270

Phe His Ser His Glu Phe His Ser His Glu Asp Met Leu Val Val Asp
        275                 280                 285

Pro Lys Ser Lys Glu Glu Asp Lys His Leu Lys Phe Arg Ile Ser His
    290                 295                 300

Glu Leu Asp Ser Ala Ser Ser Glu Val Asn
305                 310
```